United States Patent
Yamakawa et al.

(10) Patent No.: US 7,164,024 B2
(45) Date of Patent: Jan. 16, 2007

(54) BENZIMIDAZOLONE DERIVATIVES

(75) Inventors: Takeru Yamakawa, Tsukuba (JP); Yoshio Ogino, Tsukuba (JP); Yufu Sagara, Tsukuba (JP); Kenji Matsuda, Tsukuba (JP); Akira Naya, Tsukuba (JP); Toshifumi Kimura, Tsukuba (JP); Norikazu Otake, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 176 days.

(21) Appl. No.: 10/475,447

(22) PCT Filed: Apr. 19, 2002

(86) PCT No.: PCT/JP02/03958

§ 371 (c)(1),
(2), (4) Date: Oct. 20, 2003

(87) PCT Pub. No.: WO02/085890

PCT Pub. Date: Oct. 31, 2002

(65) Prior Publication Data

US 2004/0147506 A1    Jul. 29, 2004

(30) Foreign Application Priority Data

Apr. 20, 2001  (JP) ............................. 2001-122057

(51) Int. Cl.
*A61K 31/44* (2006.01)
(52) U.S. Cl. ..................... 546/137; 514/305
(58) Field of Classification Search ................ 546/199, 546/192, 193, 223; 514/322, 329
See application file for complete search history.

(56) References Cited

U.S. PATENT DOCUMENTS 6,326,372 B1    12/2001    Evans et al. ................. 514/258

FOREIGN PATENT DOCUMENTS

| GB | 2355263 | 4/2001 |
|---|---|---|
| WO | 96/13262 | 5/1996 |
| WO | 97/16192 | 5/1997 |
| WO | 97/24324 | 7/1997 |
| WO | 97/40035 | 10/1997 |
| WO | 99/32481 | 7/1999 |

OTHER PUBLICATIONS

Kedar, Can We Prevent Parkinson's and Alzheimer's Disease?, J. Postgrad Med 2003; 49:236-245.*
Chapple et al, Muscarinic receptor subtypes and management of the overactive bladder, Urology 60 (Supplement 5A), Nov. 2002, 82-88.*
Eglen et al, Muscarinic receptor ligands and their therapeutic potential, PMID: 10419852.*
Nishi, T et al, 'combined NK1 and NK2 tachykinin receptor antagonists: synthesis and structure-activity relationships of novel oxazolidine analogs' CA 131:67645 (1999).*
Forbes, IT et al, 'Preparation of N-ind(az)olylsulfonyl-2-piperidinoethylpyrrolidines and analogs as 5-HT7 receptor agonists' CA 137:169522 (2002).*
Olianas et al, PD 102807, a novel muscarinic M4 receptor antagonist, discriminates between striatal and cortial muscarinic receptors coupled to cyclic AMP, Life Sciences, 65(20) 2233-2240 (1999).*
J. Med. Chem., 39(7), (1996), p. 1514-1520.
Roufos, I., et al.; J. Med. Chem., vol. 39, pp. 1514-1520 (1996).

* cited by examiner

*Primary Examiner*—Amelia A. Owens
(74) *Attorney, Agent, or Firm*—Wenderoth, Lind & Ponack, L.L.P.

(57) ABSTRACT

This invention relates to benzimidazolone derivatives, represented by compounds of a general formula [I]

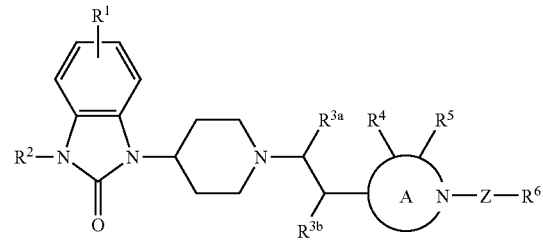

[in which $R^1$ and $R^2$ stand for, e.g., hydrogen atoms; $R^{3a}$, $R^{3b}$, $R^4$, $R^5$ stand for, e.g., hydrogen atoms and alkyl groups; $R^6$ stands for e.g., aryl or heteroaryl groups; A ring stands for 5- to 8-membered aliphatic heterocyclic ring containing one nitrogen atom; and Z stands for carbonyl group or sulfonyl group].

The benzimidazolone derivatives of the invention exhibit antagonism to muscarinic acetylcholine receptors, and are useful as treating agent and/or prophylactic of Parkinson's disease, drug-induced parkinsonism, dystonia, akinesia, pancreatitis, bilestone/cholecystitis, biliary dyskinesia, achalasia, pain, itch, cholinergic urticaria, irritable bowel syndrome, vomiting, nausea, dizziness, Meniere's disease, motion sickness and urinary disturbance.

12 Claims, No Drawings

BENZIMIDAZOLONE DERIVATIVES

TECHNICAL FIELD

This invention relates to substituted benzimidazolone derivatives which are useful in the field of pharmaceuticals. More specifically, the invention relates to substituted benzimidazolone derivatives exhibiting selective antagonist activities against muscarinic acetylcholine receptor $M_1$ and/or $M_4$ subtypes, which are useful as drug for the treatment and/or prevention of Parkinson's disease, drug-induced parkinsonism, dystonia, akinesia, pancreatitis, bilestone/cholecystitis, biliary dyskinesia, achalasia, pain, itch, cholinergic urticaria, irritable bowel syndrome, vomiting, nausea, dizziness, Meniere's disease, motion sickness such as space sickness, sea sickness and car sickness and urinary disturbance.

BACKGROUND ART

Muscarinic receptors have at least five subtypes ($M_1$ receptor, $M_2$ receptor, $M_3$ receptor, $M_4$ receptor and $M_5$ receptor) which are present in tissues or internal organs at different distribution levels. Non-selective muscarinic receptor antagonists represented by atropine and scopolamine, exhibit blocking actions of approximately the same level to these subtypes. These antagonists are effective for treating or preventing dyskinesia such as Parkinson's disease, drug-induced parkinsonism, dystonia and akinesia; diseases of digestive system such as pancreatitis, bilestone/cholecystitis, biliary dyskinesia and achalasia; pain, itch, cholinergic urticaria, irritable bowel syndrome, vomiting, nausea, dizziness, Meniere's disease, motion sickness such as space sickness, sea sickness and car sickness and urinary disturbance, but on the other hand induce such side effects as tachycardia, ocular hypertension, dry mouth, suppression of perspiration, mydriasis and constipation, which frequently prevent their use in the doses sufficient to exhibit their efficacies [cf. *Basic and Clinical Pharmacology*, 4th ed., (Appleton & Lange), pp. 83–92 (1989); *Drug News & Perspective*, Vol. 5, No. 6, pp. 345–352 (1992); *The Merck Manual*, 16th ed., pp. 1282–1283, P.1499 (1992)].

Recent research works indicate these side effects link to either one or both of $M_2$ receptor and $M_3$ receptor. That is, the side effect like tachycardia is considered to be mainly attributable to $M_2$ receptor blockade, while dry mouth, suppression of perspiration, mydriasis and constipation are considered to be caused mainly by $M_3$ receptor blockade [cf. *Journal of Pharmacology & Experimental Therapeutics*, Vol. 292, No. 3, pp. 877–885 (2000); *Proceedings of the National Academy of Sciences of the United States of America*, Vol. 97, No. 17, pp. 9579–9584 (2000)].

On the other hand, concerning dyskinesia such as Parkinson's disease, drug-induced parkinsonism, dystonia or akinesia, the involvemet of $M_4$ receptors is suggested. [cf. *Proceedings of the National Academy of Sciences of the United States of America*, Vol. 96, No. 18, pp. 10483–10488 (1999)].

$M_4$ receptor is also suggested to take part in various physiological actions such as gallbladder contraction, relaxation of bladder smooth muscles and pain [cf. *Pharmacological Research*, Vol. 39, No. 5, pp. 389–395 (1999); *Journal of Pharmacology & Experimental Therapeutics*, Vol. 283, No. 2, pp. 750–756 (1997); *Journal of Autonomic Pharmacology*, Vol. 18, No. 4, pp. 195–204 (1998); *Journal of Pharmacology & Experimental Therapeutics*, Vol. 282, No. 1, pp. 430–439 (1997)].

Furthermore, participation of $M_1$ receptor or $M_4$ receptor in vomiting, nausea, dizziness, Meniere's disease and motion sickness is suggested by the data shown in the following papers [cf. *Neurochemistry International*, Vol. 25, No. 5, pp. 455–464 (1994); *Neuropharmacology*, Vol. 27, No. 9, pp. 949–956 (1988)].

Considering the foregoing, substances which exhibit selective antagonistic activities at $M_1$ or $M_4$ receptors and weak blocking effect on $M_2$ and $M_3$ receptors can be expected to have therapeutic effects on such diseases as Parkinson's disease, drug-induced parkinsonism, dystonia, akinesia, pancreatitis, bilestone/cholecystitis, biliary dyskinesia, achalasia, pain, itch, cholinergic urticaria, irritable bowel syndrome, vomiting, nausea, dizziness, Meniere's disease, motion sickness such as space sickness, sea sickness and car sickness and urinary disturbance, without inducing such side effects as tachycardia, dry mouth, suppression of perspiration, mydriasis or constipation.

Compounds resembling compounds of the present invention in structure are disclosed, e.g., in International Publications WO 96/13262, WO 97/16192, WO 97/40035 and WO 99/32481, all of which share 1-(piperidin-4-yl)-1,3-dihydro-2H-benzimidazol-2-one skeleton, with the compounds of the present invention. Nevertheless those compounds which are disclosed in WO 97/16192, WO 97/40035 or WO 99/32481 have different kinds of functional groups substituting at 1-position of the piperidine ring in said skeletal structure, from those in the present invention. On the other hand, WO 96/13262 claims compounds with a broad scope of substituents at 1-position of the piperidine ring, which encompass a part of the compounds of the present invention, but the publication contains no specific disclosure about the compounds with a spacer between the piperidine ring and the nitrogen-containing alicyclic heterocyclic group, which is characteristic of the present invention.

Moreover, WO 99/32481 or WO 97/40035 contain no disclosure that their compounds particularly inhibit $M_1$ or $M_4$ receptors with high selectivity. While those compounds described in WO 97/16192 and WO 96/13262 are said to exhibit inhibitory activity against muscarinic $M_1$, $M_2$ and $M_4$ receptors but only weak inhibitory action against $M_3$ receptor, specific compounds or their inhibitory activity are not disclosed at all. Nor there is any disclosure about the compounds' having selective inhibitory action against $M_1$ and $M_4$ receptors.

DISCLOSURE OF THE INVENTION

An objective of the present invention is to provide compounds which exhibit selective antagonism at muscarinic receptors $M_1$ subtype and/or $M_4$ subtype, in particular, $M_4$ subtype, which are useful as drugs, and their production processes.

A further objective of the present invention is to provide muscarinic receptor antagonists and drugs for treating or preventing diseases or symptoms associated with muscarinic receptors (in particular, $M_1$ or $M_4$ receptors).

With the view to solve the above problems, we have engaged in concentrative studies to discover: among a series of compounds having 1-(piperidin-4-yl)-1,3-dihydro-2H-benzimidazol-2-one and nitrogen-containing heterocyclic group, a special type of benzimidazolone derivatives whose chemical structures are characterized by the presence of an ethylene group as a spacer between the two groups possess selective antagonism at $M_1$ and/or $M_4$ subtypes, in particular, $M_4$ subtype, of muscarinic receptors. We furthermore discovered that these compounds are useful for the prevention and/or treatment of Parkinson's disease, drug-induced parkinsonism, dystonia, akinesia, pancreatitis, bilestone/cholecystitis, biliary dyskinesia, achalasia, pain, itch, cholinergic urticaria, irritable bowel syndrome, vomiting, nausea, dizziness, Meniere's disease, motion sickness such as space sickness, sea sickness and car sickness and urinary disturbance. Based on these discoveries, we have come to complete the present invention.

Accordingly, therefore, the present invention relates to:
1. benzimidazolone derivatives represented by a general formula [I]

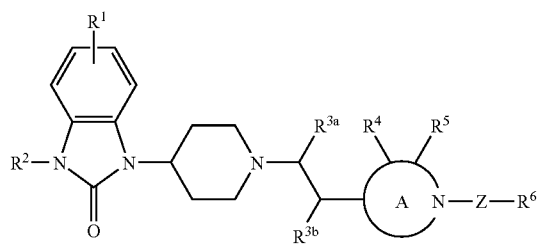

[in which A ring

(hereafter this group is referred to as "A ring") stands for a 5- to 8-membered aliphatic heterocyclic ring containing one nitrogen atom; $R^1$ binds to the benzene ring, standing for hydrogen, halogen, lower alkyl or lower alkoxy; $R^2$ stands for hydrogen or optionally phenyl-substituted lower alkyl; $R^{3a}$ and $R^{3b}$ stand for hydrogen or $R^3$, $R^{3a}$ standing for hydrogen when $R^{3b}$ stands for $R^3$ and $R^{3a}$ standing for $R^3$ when $R^{3b}$ stands for hydrogen; $R^3$ stands for hydrogen, halogen, hydroxyl, lower alkyl or lower alkenyl, or $R^3$ (i.e., $R^{3a}$ or $R^{3b}$) and $R^4$ together form a 3- to 6-membered carbocyclic ring with the carbon atoms to which they bind; $R^4$ and $R^5$ which are the same or different and bind to optional carbon atoms constituting said heterocyclic ring, stand for hydrogen, halogen, hydroxyl, lower alkyl or lower alkenyl, or $R^4$ and $R^5$ together form methylene group with the carbon atoms to which they bind, or $R^3$ (i.e., $R^{3a}$ and $R^{3b}$) and $R^4$ together form a 3- to 6-membered carbocyclic ring with the carbon atoms to which they bind, or $R^4$ and $R^5$ together form a 3- to 6-membered carbocyclic ring together with the carbon atoms to which they bind; $R^6$ stands for aryl or heteroaryl which may have one, two or more substituents selected from the group consisting of halogen, cyano, nitro, lower alkyl, lower alkenyl, lower alkynyl, lower cycloalkyl, halogenated lower alkyl, lower alkylamino, di-lower alkylamino, lower alkylthio, lower alkylsulfonyl, optionally fluorine-substituted lower alkoxy, lower acyl, lower acylamino, lower alkoxycarbonyl, carbamoyl, lower alkylcarbamoyl, di-lower alkylcarbamoyl, sulfamoyl, lower alkylsulfamoyl, di-lower alkylsulfamoyl, carbamoyloxy, lower alkylcarbamoyloxy, di-lower alkylcarbamoyloxy, lower alkoxycarbonylamino, sulfamoylamino, (lower alkylsulfamoyl)amino, (di-lower alkylsulfamoyl)amino, (lower alkylsulfamoyl)(lower alkyl)amino, (di-lower alkylsulfamoyl) (lower alkyl)amino, (lower alkylsulfonyl)amino, carbamoylamino, (lower alkylcarbamoyl)amino, (di-lower alkylcarbamoyl)amino and phenoxy; and Z stands for carbonyl (—CO—) or sulfonyl (—SO$_2$—)] or salts thereof:

2. benzimidazolone derivatives or salts thereof as described in Item 1, in which the benzimidazolone derivatives represented by the general formula [I] are those of a general formula [I-a]

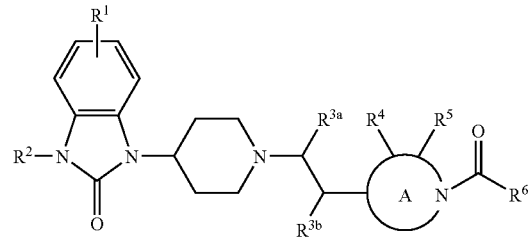

[in which $R^1$, $R^2$, $R^{3a}$, $R^{3b}$, $R^4$, $R^5$, $R^6$ and A ring are same as those in Item 1]:

3. benzimidazolone derivatives or salts thereof as described in Item 1, in which the benzimidazolone derivatives represented by the general formula [I] are those of a general formula [I-b]

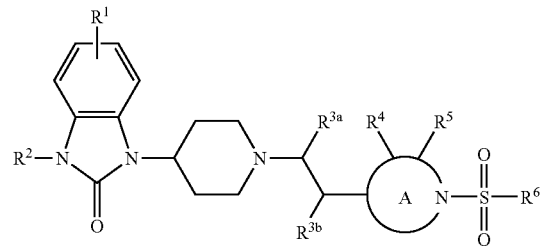

[in which $R^1$, $R^2$, $R^{3a}$, $R^{3b}$, $R^4$, $R^5$, $R^6$ and A ring are same as those in Item 1]:

4. benzimidazolone derivatives or salts thereof as described in Item 1, in which the A ring is one selected from the group consisting of pyrrolidine ring, piperidine ring, perhydroazepine ring, heptamethylenimine ring and 1,2,5,6-tetrahydropyridine ring:

5. benzimidazolone derivatives or salts thereof as described in Item 1, in which $R^6$ is a group selected from the group consisting of phenyl, 1-naphthyl, 2-naphthyl, 2-tolyl, 3-tolyl, 4-tolyl, 2-chlorophenyl, 3-chlorophenyl, 4-chlorophenyl, 3,4-dichlorophenyl, 3,5-dichlorophenyl, 3-bromophenyl, 2-fluoro-4-chlorophenyl, 3-iodophenyl, 4-iodophenyl, 2-(trifluoromethyl)phenyl, 3-(trifluoromethyl)phenyl, 2-(dimethylamino)phenyl, 3-(dimethylamino)phenyl, 2-cyanophenyl, 3-cyanophenyl, 2-(acetamido)phenyl, 3-(acetamido)phenyl, 3-(chloromethyl)phenyl, 2-methoxyphenyl, 3-methoxyphenyl, 2-(phenoxy)phenyl, 3-(phenoxy)phenyl, pyrazinyl, 2-pyridyl, 3-pyridyl, 4-pyridyl, 5-chloro-3-pyridyl, 5-bromo-3-pyridyl, 5-cyano-3-pyridyl, 2-chloro-3-pyridyl, 6-chloro-3-pyridyl, 2,3-dichloropyridin-5-yl, 5-methyl-3-pyridyl, 2-methoxypyridyl, 2-phenoxypyridyl, 2-(methylthio)pyridyl, 2-methylpyridin-5-yl, 3-bromopyridin-5-yl, 2,6- dimethoxypyridyl, 2-(propylthio)pyridyl, 2-thienyl, 3-thienyl, 2-quinolyl and 3-quinolyl:

6. benzimidazolone derivatives or salts thereof as described in Item 1, in which the benzimidazolone derivative represented by the general formula [I] is 1-[1-[2-(1-benzoylpiperidin-4-yl)ethyl]piperidin-4-yl]-1,3-dihydro-2H-benzimidazol-2-one, 1-[1-[2-[1-(4-chlorophenylsulfonyl)piperidin-4-yl]ethyl]piperidin-4-yl]-1,3-dihydro-2H-benzimidazol-2-one, 1-[1-[2-[1-[4-(trifluoromethoxy)phenylsulfonyl]piperidin-4-yl]ethyl]-piperidin-4-yl]-1,3-dihydro-2H-benzimidazol-2-one, 1-[1-[2-[1-(pyrazinylcarbonyl)piperidin-4-yl]ethyl]piperidin-4-yl]-1,3-dihydro-2H-benzimidazol-2-one, 1-[1-[2-[1,2,5,6-tetrahydro-1-(pyrazinylcarbonyl)-4-pyridyl]ethyl]-piperidin-4-yl]-1,3-dihydro-2H-benzimidazol-2-one, 1-[1-[2-[1-(pyrazinylcarbonyl)-3-methylene-piperidin-4-yl]ethyl]-piperidin-4-yl]-1,3-dihydro-2H-benzimidazol-2-one, (S*)-1-[1-[2-[1-(pyrazinylcarbonyl)perhydroazepin-4-yl]ethyl]-piperidin-4-yl]-1,3-dihydro-2H-benzimidazol-2-one, (R*)-1-[1-[2-[1-(pyrazinylcarbonyl)perhydroazepin-4-yl]ethyl]-piperidin-4-yl]-1,3-dihydro-2H-benzimidazol-2-one, (S*)-1-[1-[2-[1-(3-pyridylcarbonyl)perhydroazepin-4-yl]ethyl]-piperidin-4-yl]-1,3-dihydro-2H-benzimidazol-2-one, (R*)-1-[1-[2-[1-(3-pyridylcarbonyl)perhydroazepin-4-yl]ethyl]-piperidin-4-yl]-1,3-dihydro-2H-benzimidazol-2-one, 1-[1-[2-[1-(pyrazinylcarbonyl)piperidin-4-yl]propyl]piperidin-4-yl]-1,3-dihydro-2H-benzimidazol-2-one, 1-[1-[2-[1-(3-pyridylcarbonyl)piperidin-4-yl]propyl]piperidin-4-yl]-1,3-dihydro-2H-benzimidazol-2-one, 1-[1-[2-[1-(3-chlorobenzoyl)piperidin-4-yl]propyl]piperidin-4-yl]-1,3-dihydro-2H-benzimidazol-2-one, 1-[1-[2-[1-(3-pyridylcarbonyl)piperidin-4-yl]-1-methylethyl]piperidin-4-yl]-1,3-dihydro-2H-benzimidazol-2-one, 1-[1-[2-hydroxy-2-[4-hydroxy-1-(3-pyridylcarbonyl)piperidin-4-yl]-ethyl]piperidin-4-yl]-1,3-dihydro-2H-benzimidazol-2-one, 1-[1-[2-[1-(2-chlorobenzoyl)piperidin-4-yl]ethyl]-piperidin-4-yl]-1,3-dihydro-2H-benzimidazol-2-one, 1-[1-[2-[1-(3-chlorobenzoyl)piperidin-4-yl]ethyl]-piperidin-4-yl]-1,3-dihydro-2H-benzimidazol-2-one, 1-[1-[2-[1-(3-bromobenzoyl)piperidin-4-yl]ethyl]-piperidin-4-yl]-1,3-dihydro-2H-benzimidazol-2-one, 1-[1-[2-[1-(3-iodobenzoyl)piperidin-4-yl]ethyl]-piperidin-4-yl]-1,3-dihydro-2H-benzimidazol-2-one, 1-[1-[2-[1-(3,5-dichlorobenzoyl)piperidin-4-yl]ethyl]-piperidin-4-yl]-1,3-dihydro-2H-benzimidazol-2-one, 1-[1-[2-[1-(3,4-dichlorobenzoyl)piperidin-4-yl]ethyl]-piperidin-4-yl]-1,3-dihydro-2H-benzimidazol-2-one, 1-[1-[2-[1-(3-pyridylcarbonyl)piperidin-4-yl]ethyl]-piperidin-4-yl]-1,3-dihydro-2H-benzimidazol-2-one, 1-[1-[2-[1-[(5-chloro-3-pyridyl)carbonyl]piperidin-4-yl]ethyl]-piperidin-4-yl]-1,3-dihydro-2H-benzimidazol-2-one, 1-[1-[2-[1-[(4,5-dichloro-3-pyridyl)carbonyl]piperidin-4-yl]ethyl]-piperidin-4-yl]-1,3-dihydro-2H-benzimidazol-2-one, 1-[1-[2-[1-[(5-bromo-3-pyridyl)carbonyl]piperidin-4-yl]ethyl]-piperidin-4-yl]-1,3-dihydro-2H-benzimidazol-2-one, 1-[1-[2-[1-(2-thenoyl)piperidin-4-yl]ethyl]-piperidin-4-yl]-1,3-dihydro-2H-benzimidazol-2-one, 1-[1-[2-[1-(3-pyridylcarbonyl)piperidin-4-yl]ethyl]-piperidin-4-yl]-5-fluoro-1,3-dihydro-2H-benzimidazol-2-one, 1-[1-[2-(1-pyrazinylcarbonylpiperidin-4-yl)ethyl]-piperidin-4-yl]-5-fluoro-1,3-dihydro-2H-benzimidazol-2-one, 1-[1-[2-[1-[(5,6-dichloro-3-pyridyl)carbonyl]-piperidin-4-yl]ethyl]-piperidin-4-yl]-1,3-dihydro-2H-benzimidazol-2-one, 1-[1-[2-[1-[(2-propylthio-3-pyridyl)carbonyl]piperidin-4-yl]ethyl]-piperidin-4-yl]-1,3-dihydro-2H-benzimidazol-2-one, 1-[1-[2-[4-fluoro-1-(pyrazinylcarbonyl)piperidin-4-yl]propyl]piperidin-4-yl]-1,3-dihydro-2H-benzimidazol-2-one, 1-[1-[2-[4-fluoro-1-(3-pyridylcarbonyl)piperidin-4-yl]propyl]piperidin-4-yl]-1,3-dihydro-2H-benzimidazol-2-one, 1-[1-[(1α,5α,7β)-3-(pyrazinylcarbonyl)-3-azabicyclo[3.3.0]octan-7-yl]-piperidin-4-yl]-1,3-dihydro-2H-benzimidazol-2-one, 1-[1-[(1α,5α,7α)-3-(pyrazinylcarbonyl)-3-azabicyclo[3.3.0]octan-7-yl]-piperidin-4-yl]-1,3-dihydro-2H-benzimidazol-2-one, 1-[1-[(1α, 5α, 7β)-3-(3-pyridylcarbonyl)-3-azabicyclo[3.3.0]octan-7-yl]-piperidin-4-yl]-1,3-dihydro-2H-benzimidazol-2-one, 1-[1-[(1α,5α,7α)-3-(3-pyridylcarbonyl)-3-azabicyclo[3.3.0]octan-7-yl]-piperidin-4-yl]-1,3-dihydro-2H-benzimidazol-2-one, 1-[1-[(1α,7α,9β)-4-(pyrazinylcarbonyl)-4-azabicyclo[5.3.0]nonan-9-yl]-piperidin-4-yl]-1,3-dihydro-2H-benzimidazol-2-one, 1-[1-[2-[7-(3-pyridylcarbonyl)-7-azaspiro[3.5]nonan-2-yl]ethyl]-piperidin-4-yl]-1,3-dihydro-2H-benzimidazol-2-one, 1-[1-[2-[7-(pyrazinylcarbonyl)-7-azaspiro[3.5]nonan-2-yl]ethyl]-piperidin-4-yl]-1,3-dihydro-2H-benzimidazol-2-one, or 1-[1-[[6-(3-pyridylcarbonyl)-6-azaspiro[2.5]octan-1-yl]methyl]-piperidin-4-yl]-1,3-dihydro-2H-benzimidazol-2-one:

7. a method for producing benzimidazolone derivatives represented by the general formula [I]

[I]

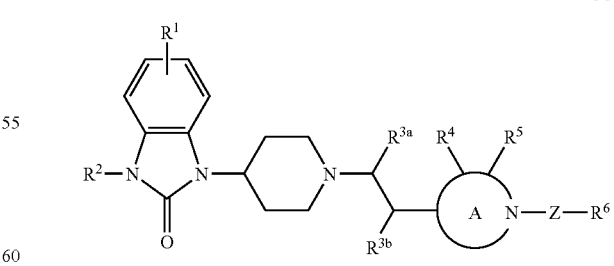

[in which $R^1$, $R^2$, $R^{3a}$, $R^{3b}$, $R^4$, $R^5$, $R^6$, Z and A ring are same as described in Item 1]

or salts thereof, which comprises a) a step of reacting a compound represented by a general formula [II]

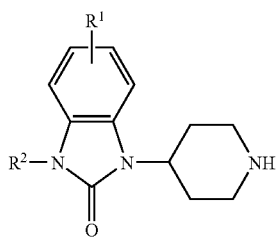

[in which R¹ and R² are same as earlier defined] with a compound represented by a general formula [III]

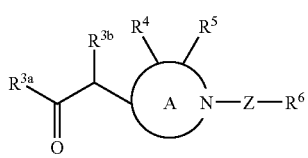

[in which $R^{3a}$, $R^{3b}$, $R^4$, $R^5$, $R^6$, Z and A ring are same as earlier defined]
to form a compound represented by a general formula [IV]

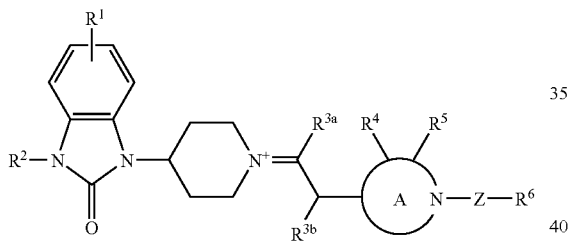

[in which $R^1$, $R^2$, $R^{3a}$, $R^{3b}$, $R^4$, $R^5$, $R^6$, Z and A ring are same as earlier defined] and b) a step of reducing (reducing the nitrogen-carbon double bond) the compound of the general formula [IV] as obtained in the step a):

8. a method for producing benzimidazolone derivatives represented by the general formula [I]

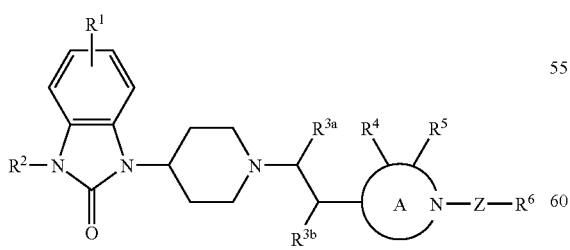

[in which $R^1$, $R^2$, $R^{3a}$, $R^{3b}$, $R^4$, $R^5$, $R^6$, Z and A ring are same as described in Item 1]
or salts thereof, which comprises a step of reacting a compound represented by the general formula [II]

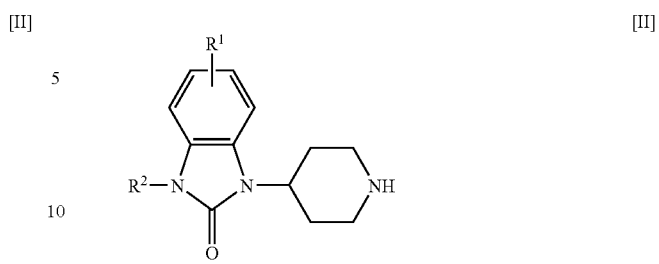

[in which R¹ and R² are same as earlier defined] with a compound represented by the general formula [III]

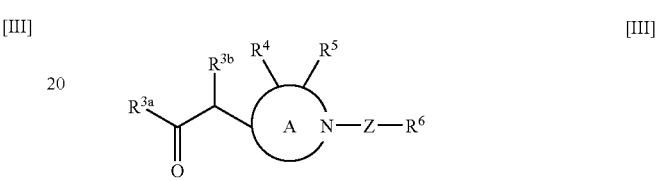

[in which $R^{3a}$, $R^{3b}$, $R^4$, $R^5$, $R^6$, Z and A ring are same as earlier defined]
in the presence of a reagent (reducing agent) which is selected from a group consisting of sodium borohydride, sodium cyanoborohydride, zinc cyanoborohydride and sodium triacetoxyborohydride:

9. a method for producing benzimidazolone derivatives represented by the general formula [I]

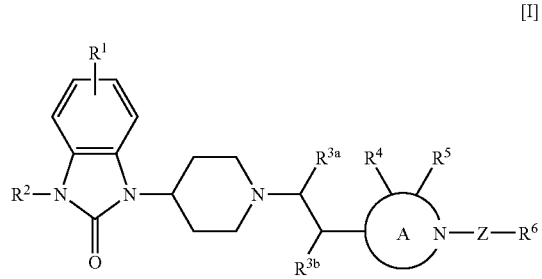

[in which $R^1$, $R^2$, $R^{3a}$, $R^{3b}$, $R^4$, $R^5$, $R^6$, Z and A ring are same as described in Item 1]
or salts thereof, which comprises
a step of reacting a compound represented by a general formula [II]

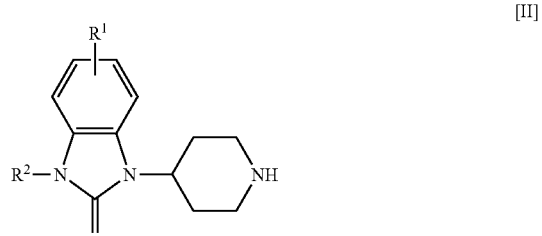

[in which R¹ and R² are same as earlier defined] with a compound represented by a general formula [V]

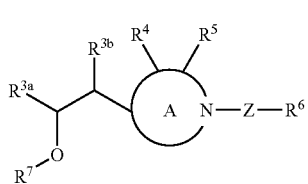

[in which $R^{3a}$, $R^{3b}$, $R^4$, $R^5$, $R^6$, Z and A ring are same as earlier defined; $R^7$ stands for methylsulfonyl, phenylsulfonyl or p-tolylsulfonyl]

preferably in the presence of a base:

10. a method for producing benzimidazolone derivatives represented by the general formula [I-a]

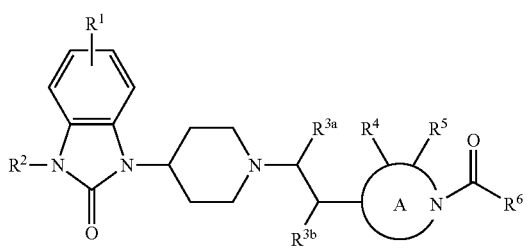

[in which $R^1$, $R^2$, $R^{3a}$, $R^{3b}$, $R^4$, $R^5$ and A ring are same as earlier defined]

or salts thereof which comprises a step of subjecting a compound of a general formula [VI]

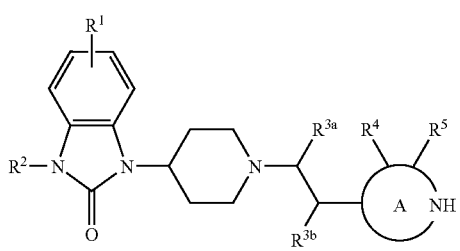

[in which $R^1$, $R^2$, $R^{3a}$, $R^{3b}$, $R^4$, $R^5$ and A ring are same as earlier defined]

and a carboxylic acid represented by a general formula [VII-a]

$R^6$—COOH  [VII-a]

[in which $R^6$ is same as earlier defined]

or an activated derivative thereof, to a reaction (amidation reaction):

11. a method for producing benzimidazolone derivatives represented by the general formula [I-b]

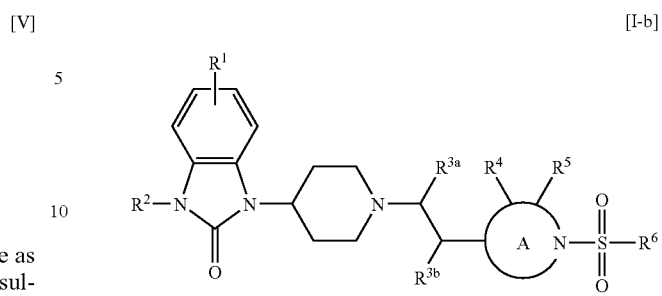

[in which $R^1$, $R^2$, $R^{3a}$, $R^{3b}$, $R^4$, $R^5$, $R^6$ and A ring are same as earlier defined]

or salts thereof, which comprises a step of subjecting a compound represented by the general formula [VI]

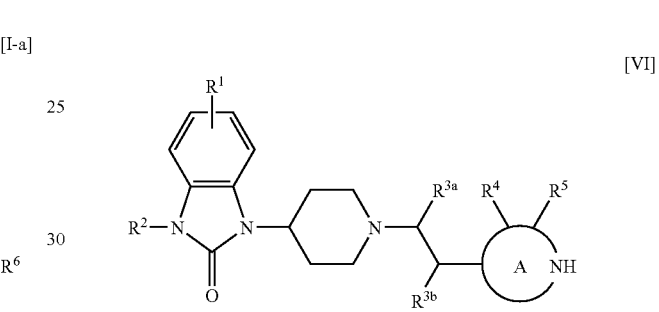

[in which $R^1$, $R^2$, $R^{3a}$, $R^{3b}$, $R^4$, $R^5$ and A ring are same as earlier defined]

to a reaction with a sulfonic acid of a general formula [VII-b]

[in which $R^6$ is same as earlier defined]

or an activated derivative thereof, in the presence or absence of a base:

12. pharmaceutical compositions containing benzimidazolone derivatives represented by the general formula [I]

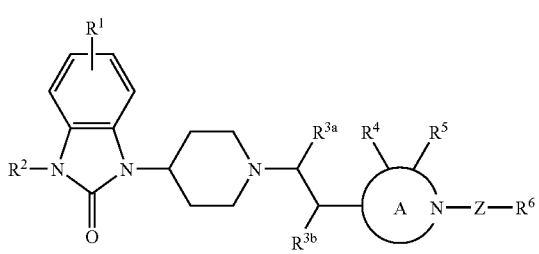

[in which $R^1$, $R^2$, $R^{3a}$, $R^{3b}$, $R^4$, $R^5$, $R^6$, Z and A ring are same as defined in Item 1]

or salts thereof, and pharmaceutically acceptable adjuvants:

13. muscarinic receptor antagonists which contain benzimidazolone derivatives represented by the general formula [I]

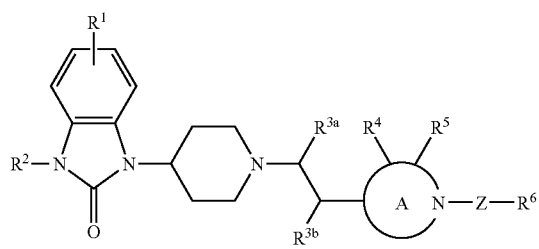

[in which $R^1$, $R^2$, $R^{3a}$, $R^{3b}$, $R^4$, $R^5$, $R^6$, Z and A ring are same as defined in Item 1]

or salts thereof as the active ingredients: and 14. drugs for the treatment and/or prevention of Parkinson's disease, drug-induced parkinsonism, dystonia, akinesia, pancreatitis, bilestone/cholecystitis, biliary dyskinesia and achalasia, pain, itch, cholinergic urticaria, irritable bowel syndrome, vomiting, nausea, dizziness, Meniere's disease, motion sickness such as space sickness, sea sickness and car sickness and urinary disturbance, which contain benzimidazolone derivatives represented by the general formula [I]

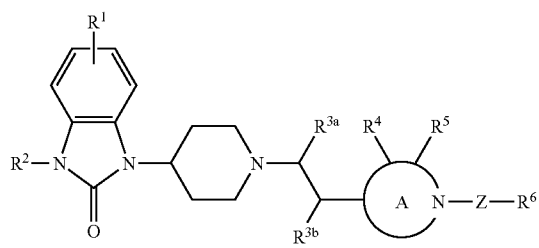

[in which $R^1$, $R^2$, $R^{3a}$, $R^{3b}$, $R^4$, $R^5$, $R^6$, Z and A ring are same as defined in Item 1]

or salts thereof as the active ingredients.

The invention relates further to:

15. benzimidazolone derivatives or salts thereof which are described in any one of Items 1–3, in which both $R^{3a}$ and $R^{3b}$ are hydrogen atoms, or either one of $R^{3a}$ and $R^{3b}$ is hydrogen atom and the other is methyl group;

16. benzimidazolone derivatives or salts thereof which are described in any one of Items 1–3, in which $R^6$ is a group selected from the group consisting of phenyl, 3-chlorophenyl, 4-chlorophenyl, 4-(trifluoromethoxy)phenyl, pyrazinyl and 3-pyridyl;

17. a method for producing benzimidazolone derivatives represented by the general formula [I] or salts thereof, which comprises a step of reacting a compound of a general formula [XIII]

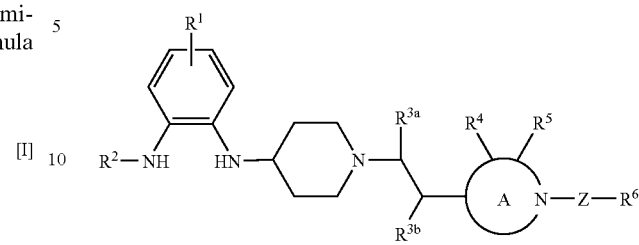

[in which $R^1$, $R^2$, $R^{3a}$, $R^{3b}$, $R^4$, $R^5$, $R^6$, Z and A ring are same as earlier defined]

with a compound selected from the group consisting of carbonyldiimidazole, triphosgene, diphosgene, methyl chloroformate, ethyl chloroformate, phenyl chloroformate, dimethyl carbonate, diethyl carbonate, S,S-dimethyl dithiocarbonate, S,S-diethyl dithiocarbonate and urea, preferably in the presence of a base;

18. a method for producing benzimidazolone derivatives represented by the general formula [I] or salts thereof, which comprises a step of reducing (reducing nitrogen-carbon double bond) compounds represented by the general formula [IV]

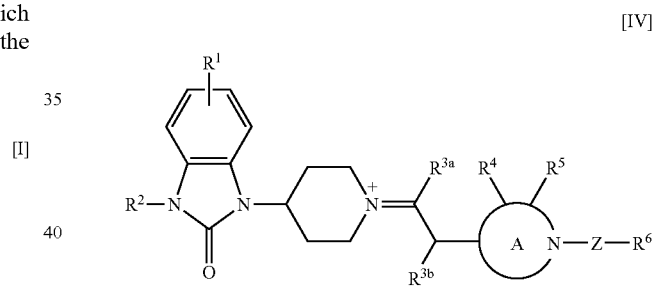

[in which $R^1$, $R^2$, $R^{3a}$, $R^{3b}$, $R^4$, $R^5$, $R^6$, Z and A ring are same as earlier defined];

19. a method for producing benzimidazolone derivatives represented by the general formula [I] or salts thereof, which comprises a) a step of reacting a compound of the general formula [II]

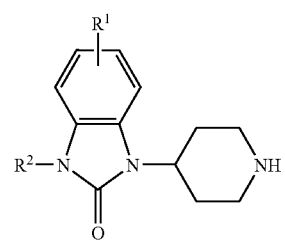

[in which $R^1$ and $R^2$ are same as earlier defined]

with a compound of a general formula [VIII]

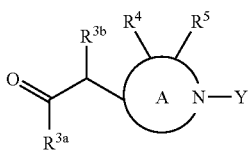

[VIII]

[in which $R^{3a}$, $R^{3b}$, $R^4$, $R^5$ and A ring are same as earlier defined, and Y stands for an amino-protective group] to form a compound of a general formula [IX]

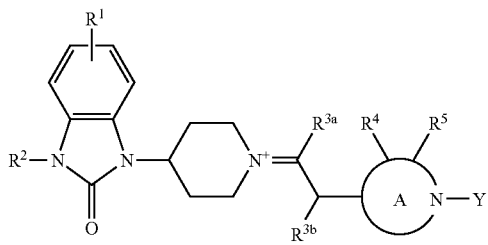

[IX]

[in which $R^1$, $R^2$, $R^{3a}$, $R^{3b}$, $R^4$, $R^5$, Y and A ring are same as earlier defined]

b) a step of reducing the nitrogen-carbon double bond in the compound of the general formula [IX] which is obtained in the above step a), to form a compound of a general formula [X]

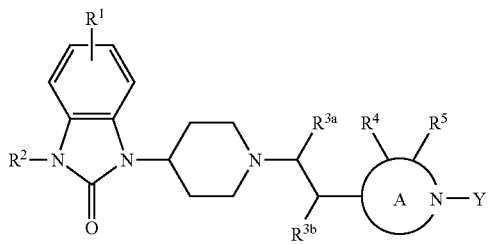

[X]

in which $R^1$, $R^2$, $R^{3a}$, $R^{3b}$, $R^4$, $R^5$, Y and A ring are same as earlier defined]

c) a step of removing the protective group Y in the compound of the general formula [X] which is obtained in the preceding step b) to form a compound of the general formula [VI]

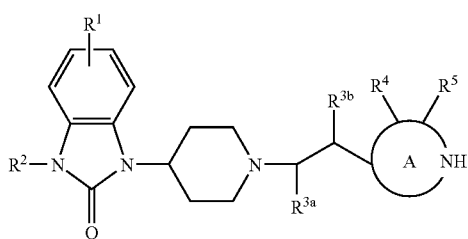

[VI]

[in which $R^1$, $R^2$, $R^{3a}$, $R^{3b}$, $R^4$, $R^5$ and A ring are same as earlier defined] and d) a step of subjecting the compound of the general formula [VI] which is obtained in the preceding step c) and a carboxylic acid or sulfonic acid represented by a general formula [VII]

$R^6$-Z-OH  [VII]

[in which $R^6$ and Z are same as earlier defined] or their activated derivatives to a reaction (amidation reaction);

20. a method for producing benzimidazolone derivatives represented by the general formula [I] or salts thereof, which comprises subjecting a compound of the general formula [II]

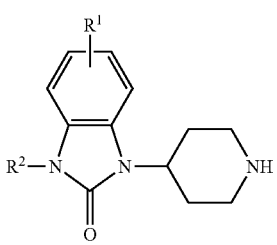

[II]

[in which $R^1$ and $R^2$ are same as earlier defined] and a compound of the general formula [XII]

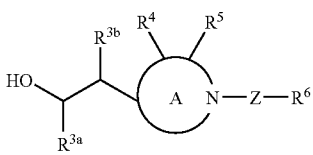

[XII]

[in which $R^{3a}$, $R^{3b}$, $R^4$, $R^5$, $R^6$, Z and A ring are same as earlier defined]
to condensation reaction in the presence of dialkyl azodicarboxylate and an organophosphorus compound such as triarylphosphine or trialkylphosphine;

21. Use of benzimidazolone derivatives represented by the general formula [I] or salts thereof for formulating pharmaceutical compositions adapted for treating and/or preventing Parkinson's disease, drug-induced parkinsonism, dystonia, akinesia, pancreatitis, bilestone/cholecystitis, biliary dyskinesia, achalasia, pain, itch, cholinergic urticaria, irritable bowel syndrome, vomiting, nausea, dizziness, Meniere's disease, motion sickness and urinary disturbance; and 22. methods of treatment and/or prophylaxis of Parkinson's disease, drug-induced parkinsonism, dystonia, akinesia, pancreatitis, bilestone/cholecystitis, biliary dyskinesia, achalasia, pain, itch, cholinergic urticaria, irritable bowel syndrome, vomiting, nausea, dizziness, Meniere's disease, motion sickness and urinary disturbance, which methods are characterized by administering to patients benzimidazolone derivatives represented by the general formula [I] or salts thereof.

Hereinafter the symbols and terms used in this specification are explained.

As "halogen", fluorine, chlorine, bromine and iodine are named, for example.

As "lower alkyl", $C_1$–$C_6$ linear or branched alkyl can be named for example, specific examples including methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

As "lower alkyl which is optionally substituted with phenyl", those lower alkyl groups as above-named, in which hydrogen atoms at optional positions are substituted with phenyl can be named for example, specific examples including benzyl, phenethyl and 3-phenylpropyl, in addition to the above-named specific examples.

As "lower alkenyl", for example, $C_2$–$C_6$ linear or branched alkenyl can be named, specific examples including vinyl, 1-propenyl, allyl, isopropenyl, 3-butenyl, 2-butenyl, 1-butenyl, 1-methylallyl, 1-methyl-1-propenyl, 1-ethylvinyl, 2-methylallyl, 2-methyl-1-propenyl, 3-methyl-2-butenyl and 4-pentenyl.

As "lower alkynyl", $C_2$–$C_6$ linear or branched alkynyl can be named for example, specific examples including ethynyl, 1-propynyl, 2-propynyl, 1-methyl-2-propynyl, 1-butynyl, 2-butynyl, 1-methyl-2-butynyl, 1-pentynyl and 1-hexynyl.

As "lower cycloalkyl", for example, $C_3$–$C_6$ cycloalkyl can be named, specific examples including cyclopropyl, cyclobutyl, cyclopentyl and cyclohexyl.

As "halogenated lower alkyl", those earlier named lower alkyl groups in which substitutable, optional hydrogen atom(s) are substituted with one, two or more, preferably 1–3, halogen atoms, can be named for example, specific examples including chloromethyl, dichloromethyl, trichloromethyl, fluoromethyl, difluoromethyl, trifluoromethyl, 2-chloroethyl, 2,2-dichloroethyl, 2-fluoroethyl, 1,2-difluoroethyl, 2,2-difluoroethyl and 2,2,2-trifluoroethyl.

As "lower alkylamino", for example, amino which is mono-substituted with said lower alkyl can be named, specific examples including methylamino, ethylamino, propylamino, isopropylamino, butylamino, sec-butylamino and tert-butylamino.

As "di-lower alkylamino", for example, amino which is di-substituted with said lower alkyl can be named, specific examples including dimethylamino, diethylamino, ethylmethylamino, dipropylamino, methylpropylamino and di-isopropylamino.

As "lower alkylthio", groups in which sulfur atom binds to said lower alkyl can be named for example, specific examples including methylthio, ethylthio, propylthio, isopropylthio, butylthio, sec-butylthio and tert-butylthio.

As "lower alkylsulfonyl", sulfonyl substituted with said lower alkyl can be named for example, specific examples including methylsulfonyl, ethylsulfonyl, propylsulfonyl, isopropylsulfonyl, butylsulfonyl, sec-butylsulfonyl and tert-butylsulfonyl.

As "lower alkoxy", groups in which oxygen binds to said lower alkyl, i.e., $C_1$–$C_6$ alkoxy groups, can be named for example, specific example including methoxy, ethoxy, propoxy, isopropoxy, butoxy, isobutoxy, tert-butoxy and pentyloxy.

As "optionally fluorine-substituted lower alkoxy", above alkoxy groups whose substitutable, optional site(s) may be substituted with one, two or more, preferably 1–3, fluorine atoms can be named for example, specific examples including, in addition to the above-named alkoxy groups, fluoromethoxy, difluoromethoxy, trifluoromethoxy, 2,2-difluoroethoxy and 2,2,2-trifluoroethoxy.

As "lower acyl", $C_1$–$C_6$ alkanoyl can be named for example, specific examples including formyl, acetyl, propionyl, butyryl, isobutyryl, valeryl, isovaleryl and pivaloyl.

As "lower acylamino", amino which is substituted with above lower acyl can be named for example, specific examples including formamido, acetamido, propionylamino, butyrylamino, isobutyrylamino, valerylamino, isovalerylamino and pivaloylamino.

As "lower alkoxycarbonyl", carbonyl which is substituted with said lower alkoxy, i.e., $C_2$–$C_7$ alkoxycarbonyl, can be named for example, specific examples including methoxycarbonyl, ethoxycarbonyl, propoxycarbonyl, isopropoxycarbonyl, butoxycarbonyl, isobutoxycarbonyl, tert-butoxycarbonyl and pentoxycarbonyl.

As "lower alkylcarbamoyl", carbamoyl which is mono-substituted with said lower alkyl can be named for example, specific examples including methylcarbamoyl, ethylcarbamoyl, propylcarbamoyl, isopropylcarbamoyl, butylcarbamoyl, sec-butylcarbamoyl and tert-butylcarbamoyl.

As "di-lower alkylcarbamoyl", carbamoyl which is di-substituted with said lower alkyl can be named for example, specific examples including dimethylcarbamoyl, diethylcarbamoyl, ethylmethylcarbamoyl, dipropylcarbamoyl, methylpropylcarbamoyl and diisopropylcarbamoyl.

As "lower alkylsulfamoyl", sulfamoyl which is substituted with said lower alkyl can be named for example, specific examples including methylsulfamoyl, ethylsulfamoyl, propylsulfamoyl, isopropylsulfamoyl, butylsulfamoyl, sec-butylsulfamoyl and tert-butylsulfamoyl.

As "di-lower alkylsulfamoyl", sulfonyl binding to said di-lower alkylamino can be named for example, specific examples including dimethylsulfamoyl, diethylsulfamoyl, ethylmethylsulfamoyl, dipropylsulfamoyl, methylpropylsulfamoyl and diisopropylsulfamoyl.

As "lower alkylcarbamoyloxy", oxygen binding to said lower alkylcarbamoyl can be named for example, specific examples including methylcarbamoyloxy, ethylcarbamoyloxy, propylcarbamoyloxy, isopropylcarbamoyloxy, butylcarbamoyloxy, sec-butylcarbamoyloxy and tert-butylcarbamoyloxy.

As "di-lower alkylcarbamoyloxy", oxygen binding to said di-lower alkylcarbamoyloxy can be named for example, specific examples including dimethylcarbamoyloxy, diethylcarbamoyloxy, ethylmethylcarbamoyloxy, dipropylcarbamoyloxy, methylpropylcarbamoyloxy and diisopropylcarbamoyloxy.

As "lower alkoxycarbonylamino", amino which is mono-substituted with said lower alkoxycarbonyl can be named for example, specific examples including methoxycarbonylamino, ethoxycarbonylamino, propoxycarbonylamino, isopropoxycarbonylamino, butoxycarbonylamino, isobutoxycarbonylamino, tert-butoxycarbonylamino and pentoxycarbonylamino.

As "(lower alkylsulfamoyl)amino", amino which is mono-substituted with said lower alkylsulfamoyl can be named for example, specific examples including (methylsulfamoyl)amino, (ethylsulfamoyl)amino, (propylsulfamoyl)amino, (isopropylsulfamoyl)amino, (butylsulfamoyl)amino, (sec-butylsulfamoyl)amino and (tert-butylsulfamoyl)amino.

As "(di-lower alkylsulfamoyl)amino", amino which is substituted with said di-lower alkylsulfamoyl can be named for example, specific examples including (dimethylsulfamoyl)amino, (diethylsulfamoyl)amino, (ethylmethylsulfamoyl)amino, (dipropylsulfamoyl)amino, (methylpropylsulfamoyl)amino and (diisopropylsulfamoyl)amino.

As "(lower alkylsulfamoyl)(lower alkyl)amino", amino which is substituted with said lower alkylsulfamoyl and said lower alkyl can be named for example, specific examples including (methylsulfamoyl)methylamino and (ethylsulfamoyl)methylamino.

As "(di-lower alkylsulfamoyl)(lower alkyl)amino", amino which is substituted with said di-lower alkylsulfamoyl and said lower alkyl can be named for example, specific examples including (dimethylsulfamoyl)methylamino and (diethylsulfamoyl)methylamino.

As "(lower alkylsulfonyl)amino", amino which is mono-substituted with said lower alkylsulfonyl can be named for example, specific examples including methylsulfonylamino, ethylsulfonylamino, propylsulfonylamino, isopropylsulfonylamino, butylsulfonylamino, sec-butylsulfonylamino and tert-butylsulfonylamino.

As "(lower alkylcarbamoyl)amino", amino which is mono-substituted with said lower alkylcarbamoyl can be named for example, specific examples including (methylcarbamoyl)amino, (ethylcarbamoyl)amino, (propylcarbamoyl)amino, (isopropylcarbamoyl)amino, (butylcarbamoyl)amino, (sec-butylcarbamoyl)amino and (tert-butylcarbamoyl)amino.

As "(di-lower alkylcarbamoyl)amino", amino which is mono-substituted with said di-lower alkylcarbamoyl can be named for example, specific examples including (dimethylcarbamoyl)amino, (diethylcarbamoyl)amino, (ethylmethylcarbamoyl)amino, (dipropylcarbamoyl)amino, (methylpropylcarb amoyl)amino and (diisopropylcarbamoyl)amino.

Said "salts" of the benzimidazolone derivatives represented by the general formula [I] signify those customary ones which are pharmaceutically acceptable, and as examples acid addition salts at basic heterocyclic groups can be named. As such acid addition salts, inorganic acid salts such as hydrochloride, hydrobromide, hydroiodide, sulfate, nitrate, phosphate and perchlorate; organic acid salts such as maleate, fumarate, tartarate, citrate, ascorbate, benzoate and trifluoroacetate; and sulfonates such as methanesulfonate, isethionate, benzenesulfonate and p-toluenesulfonate and the like can be named.

Benzimidazolone Derivatives Represented by the General Formula [I]

For disclosing the benzimidazolone derivatives represented by the general formula [I] of the present invention still more specifically, each of those various symbols used in the general formula [I] is explained in further details, citing specific examples.

The benzimidazolone derivatives represented by the general formula [I] in occasions have stereoisomers such as optical isomers, diastereomers or geometrical isomers, depending on the form of the substituents therein. The benzimidazolone derivatives represented by the general formula [I] of the present invention cover all of those stereoisomers and their mixtures.

Furthermore, where $R^2$ is hydrogen, tautomers represented by a formula [I'] to the benzimidazolone derivatives of the general formula [I] can be present, which tautomers or salts thereof also are covered by the present invention:

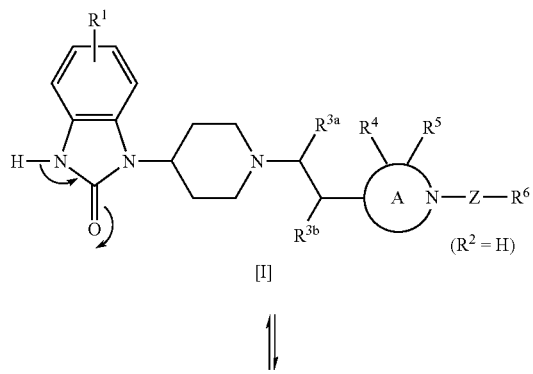

[I]

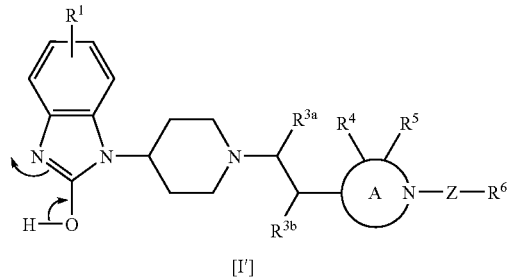

[I']

In the present specification, nomination and other explanation of compounds of the present invention are given, referring to the position numbers on the 2-benzimidazolone skeleton in the compounds of the present invention as in the following formula [a]:

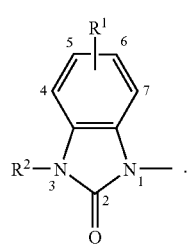

[a]

In the benzimidazolone derivatives represented by the general formula [I], $R^1$ is, for example, hydrogen, halogen, lower alkyl or lower alkoxy: more specifically, examples of halogen being fluorine, chlorine, bromine and iodine; examples of lower alkyl being methyl, ethyl, propyl and isopropyl; and examples of lower alkoxy being methoxy, ethoxy, propoxy and isopropoxy. Of these, hydrogen, fluorine, chlorine and bromine are recommendable.

The substitution site of $R^1$ may be any of 4-, 5-, 6- and 7-positions on the benzene ring in the benzimidazolone skeleton.

In the benzimidazolone derivatives represented by the general formula [I], $R^2$ is, for example, hydrogen or optionally phenyl-substituted lower alkyl. More specifically, besides hydrogen, methyl, ethyl, propyl, benzyl and 2-phenylethyl can be named for example. Preferred $R^2$ is hydrogen.

As examples of such benzimidazolone skeleton [a] containing $R^1$ and $R^2$, specifically
1,3-dihydro-2H-(benzimidazol-2-one),
4-methyl-1,3-dihydro-2H-(benzimidazol-2-one),
4-ethyl-1,3-dihydro-2H-(benzimidazol-2-one),
4-propyl-1,3-dihydro-2H-(benzimidazol-2-one),
4-methoxy-1,3-dihydro-2H-(benzimidazol-2-one),
4-ethoxy-1,3-dihydro-2H-(benzimidazol-2-one),
4-fluoro-1,3-dihydro-2H-(benzimidazol-2-one),
4-chloro-1,3-dihydro-2H-(benzimidazol-2-one),
5-methyl-1,3-dihydro-2H-(benzimidazol-2-one),
5-ethyl-1,3-dihydro-2H-(benzimidazol-2-one),
5-propyl-1,3-dihydro-2H-(benzimidazol-2-one),
5-methoxy-1,3-dihydro-2H-(benzimidazol-2-one),
5-ethoxy-1,3-dihydro-2H-(benzimidazol-2-one),
5-bromo-1,3-dihydro-2H-(benzimidazol-2-one),
5-chloro-1,3-dihydro-2H-(benzimidazol-2-one),
5-fluoro-1,3-dihydro-2H-(benzimidazol-2-one),
6-methyl-1,3-dihydro-2H-(benzimidazol-2-one), 6-ethyl-1,3-dihydro-2H-(benzimidazol-2-one),
6-propyl-1,3-dihydro-2H-(benzimidazol-2-one),
6-methoxy-1,3-dihydro-2H-(benzimidazol-2-one),
6-ethoxy-1,3-dihydro-2H-(benzimidazol-2-one),
6-chloro-1,3-dihydro-2H-(benzimidazol-2-one),
6-fluoro-1,3-dihydro-2H-(benzimidazol-2-one),
7-methyl-1,3-dihydro-2H-(benzimidazol-2-one),
7-ethyl-1,3-dihydro-2H-(benzimidazol-2-one),
7-propyl-1,3-dihydro-2H-(benzimidazol-2-one),
7-methoxy-1,3-dihydro-2H-(benzimidazol-2-one),
7-ethoxy-1,3-dihydro-2H-(benzimidazol-2-one),
7-chloro-1,3-dihydro-2H-(benzimidazol-2-one),
7-fluoro-1,3-dihydro-2H-(benzimidazol-2-one),
3-methyl-1,3-dihydro-2H-(benzimidazol-2-one), and
3-benzyl-1,3-dihydro-2H-(benzimidazol-2-one), can be named for example, and of these,
1,3-dihydro-2H-(benzimidazol-2-one),
4-fluoro-1,3-dihydro-2H-(benzimidazol-2-one),
5-fluoro-1,3-dihydro-2H-(benzimidazol-2-one),
6-fluoro-1,3-dihydro-2H-(benzimidazol-2-one),
4-chloro-1,3-dihydro-2H-(benzimidazol-2-one),
5-chloro-1,3-dihydro-2H-(benzimidazol-2-one),
6-chloro-1,3-dihydro-2H-(benzimidazol-2-one), and
5-bromo-1,3-dihydro-2H-(benzimidazol-2-one) are recommendable.

In the benzimidazolone derivatives represented by the general formula [I], A ring

is a 5- to 8-membered aliphatic heterocyclic ring containing one nitrogen atom. More specifically, pyrrolidine ring, piperidine ring, perhydroazepine ring, heptaethylenimine ring, 1,2,3,4-tetrahydropyridine ring and 1,2,5,6-tetrahydropyridine ring can be named for example, among which pyrrolidine ring, piperidine ring, perhydrozepine ring, heptamethylenimine ring and 1,2,5,6-tetrahydropyridine ring are preferred.

In the benzimidazolone derivatives which are represented by the general formula [I], $R^{3a}$ and $R^{3b}$ stand for hydrogen or $R^3$, $R^{3a}$ standing for hydrogen when $R^{3b}$ stands for $R^3$ and $R^{3a}$ standing for $R^3$ when $R^{3b}$ stands for hydrogen; $R^3$ stands for hydrogen, halogen, hydroxyl, lower ($C_1$–$C_6$) alkyl or lower ($C_2$–$C_6$) alkenyl; or $R^3$ and $R^4$ may together form (i.e., $R^3$ and $R^4$ link to each other) to form a 3- to 6-membered carbocyclic ring, together with the carbon atoms to which they bind.

As specific $R^3$, for example, besides hydrogen and hydroxyl, fluorine, bromine, chlorine, iodine, methyl, ethyl, propyl, isopropyl and vinyl may be named, and as the 3- to 6-membered carbocyclic ring formed by $R^3$, $R^4$ and the carbon atoms to which they bind, for example cyclopropane ring, cyclobutane ring, cyclopentane ring and cyclohexane ring can be named.

As preferred $R^3$, hydrogen, fluorine, methyl and ethyl are recommended, and as the ring which $R^3$ and $R^4$ form together with the carbon atoms to which they bind, cyclopropane ring, cyclopentane ring and cyclohexane ring are recommended.

In the benzimidazolone derivatives represented by the general formula [I], $R^4$ and $R^5$ bind to optional carbon atoms constituting the heterocyclic ring, which may be same or different and stand for hydrogen, hydroxyl, halogen, lower (preferably $C_1$–$C_3$) alkyl, lower (preferably $C_2$–$C_3$) alkenyl; or $R^3$ and $R^4$ may together form (i.e., as binding to each other) a 3- to 6-membered carbocyclic ring with the carbon atoms to which they bind; or $R^4$ or $R^5$ may form, together with the carbon atom to which they bind, a methylene group (later given r-15); or $R^4$ and $R^5$ may together form (i.e., as binding to each other) a 3- to 6-membered carbocyclic ring, with the carbon atoms to which they bind.

As specific examples of halogen as $R^4$ and $R^5$, fluorine, bromine, chlorine and iodine can be named; as the lower alkyl, methyl, ethyl, propyl and isopropyl can be named; and as the lower alkenyl, vinyl, 1-propenyl, allyl and isopropenyl can be named.

Where $R^3$ and $R^4$ form a 3- to 6-membered carbocyclic ring together with the carbon atoms to which they bind, as examples of the ring, cyclopropane ring (r-17), cyclobutane ring (r-13), cyclopentane ring (r-6 or r-20) and cyclohexane ring (r-8) can be named.

Where $R^4$ and $R^5$ together form a 3- to 6-membered carbocyclic ring with the carbon atoms to which they bind, as examples of the ring cyclopropane ring (r-19), cyclobutane ring, cyclopentane ring and cyclohexane ring can be named.

Of these embodiments of the substituents, hydrogen, hydroxyl and fluorine are recommended as preferred $R^4$ or $R^5$, and the cases wherein $R^4$ or $R^5$ forms methylene group together with the carbon atom to which it binds are recommended. As the ring which is formed by $R^3$ and $R^4$ together with the carbon atoms to which they bind, cyclopropane ring, cyclopentane ring and cyclohexane ring are recommended. Furthermore, as the ring formed by $R^4$ and $R^1$ together with the carbon atoms to which they bind, cyclopropane ring, cyclopentane ring and cyclohexane ring are recommended.

As preferred combinations of the aliphatic heterocyclic ring groups containing $R^3$, $R^4$ and $R^5$, for example, those having the following structures may be named.

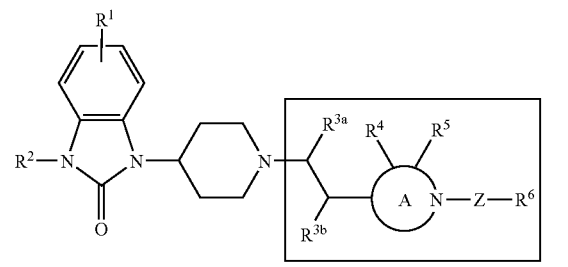

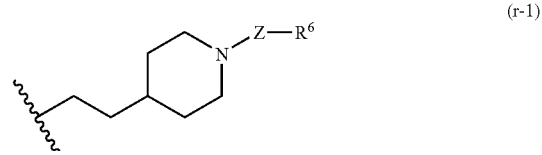
(r-1)

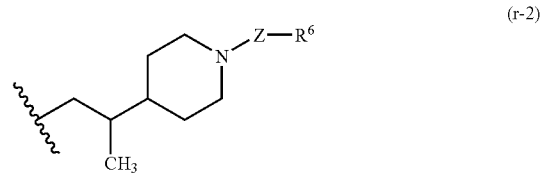
(r-2)

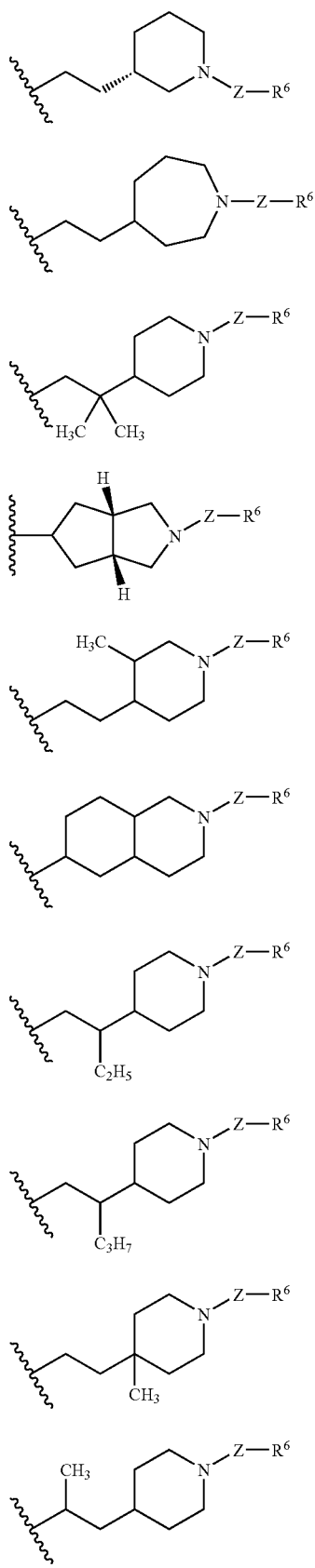
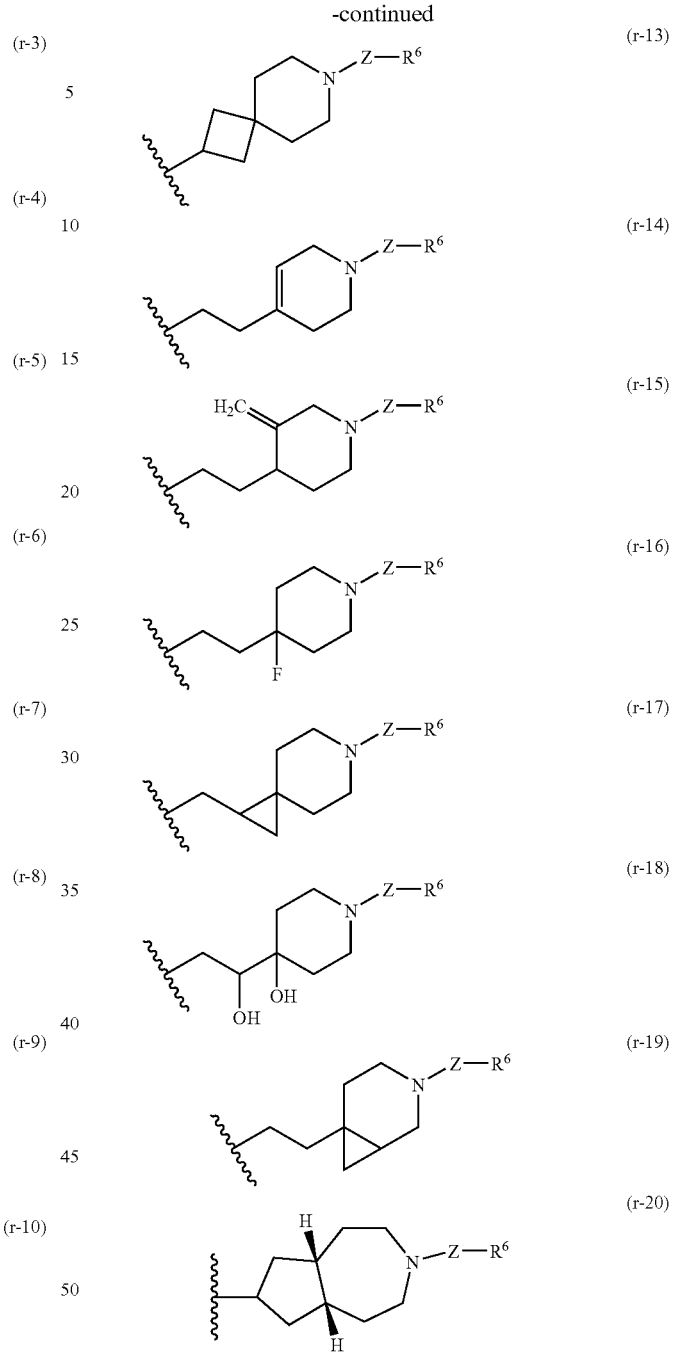

Of the above combinations, structures (r-1), (r-2), (r-4), (r-15) and (r-16) are particularly recommended.

In the benzimidazolone derivatives represented by the general formula [I], $R^6$ stands for aryl or heteroaryl which may have one, two or more, preferably 1 or 2, substituents selected from the group consisting of halogen, cyano, nitro, lower alkyl, lower alkenyl, lower alkynyl, lower cycloalkyl, halogenated lower alkyl, lower alkylamino, di-lower alkylamino, lower alkylthio, lower alkylsulfonyl, optionally fluorine-substituted lower alkoxy, lower acyl, lower acylamino, lower alkoxycarbonyl, carbamoyl, lower alkylcarbamoyl, di-lower alkylcarbamoyl, sulfamoyl, lower alkylsulfamoyl, di-lower alkylsulfamoyl, carbamoyloxy, lower alkylcarbamoyloxy, di-lower alkylcarbamoyloxy, lower alkoxycarbonylamino, sulfamoylamino, (lower alkylsulfamoylamino, (di-lower alkylsulfamoyl)amino, (lower alkylsulfamoyl)(lower alkyl)amino, (di-lower alkylsulfamoyl)(lower alkyl)amino, (lower alkylsulfonyl)amino, carbamoylamino, (lower alkylcarbamoyl)amino, (di-lower alkylcarbamoyl)amino and phenoxy. Where two or more of above substituents bind to aryl or heteroaryl, the substituents may be the same or different.

As the aryl, phenyl, naphthyl and anthryl can be named for example, and as examples of the heteroaryl, 5- or 6-membered monocyclic heteroaryl containing 1, 2 or more, preferably 1–3, same or different heteroatoms selected from the group consisting of oxygen, nitrogen and sulfur atoms; or condensed ring heteroaryl formed by condensation of said monocyclic heteroaryl with said aryl or by mutual condensation of said monocyclic heteroaryl groups which may be same or different, can be named.

As specific examples of the aryl as $R^6$, phenyl, 1-naphthyl, 2-naphthyl and 9-anthryl are named, and as the heteroaryl, 2-pyrrolyl, 3-pyrrolyl, 2-furyl, 3-furyl, 2-thienyl, 3-thienyl, 2-imidazolyl, 4-imidazolyl, 3-pyrazolyl, 4-pyrazolyl, 2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isoxazolyl, 4-isoxazolyl, 5-isoxazolyl, 1,2,4-triazol-3-yl, 1,2,3-triazol-4-yl, 5-tetrazolyl, 1,3,4-oxadiazol-2-yl, 1,3,4-thiadiazol-2-yl, 2-pyridyl, 3-pyridyl, 4-pyridyl, pyrazinyl, 2-pyrimidinyl, 4-pyrimidinyl, 5-pyrimidinyl, 3-pyridazinyl, 4-pyridazinyl, 2-indolyl, 3-indolyl, 4-indolyl, 5-indolyl, benzo[b]furan-2-yl, benzo[b]furan-3-yl, benzo[b]thiphen-2-yl, benzo[b]thiophen-3-yl, 2-benzoimidazolyl, 2-benzoxoxazolyl, 3-benzoisoxazolyl, 2-benzothiazolyl, 3-benzoisothiazolyl, 1H-benzotriazol-4-yl, 1H-indazol-3-yl, 6-purinyl, 8-purinyl, 2-quinolyl, 4-quinolyl, 1-isoquinolyl, 4-isoquinolyl, 1-phthaladinyl, 4-naphthilidinyl, 2-quinoxalinyl, 5-quinoxalinyl, 4-quinzolinyl, 4-cinnolinyl and 4-pteridinyl can be named.

As the halogen which may substitute on the aryl or heteroaryl, for example, fluorine, chlorine, bromine and iodine can be named.

As the lower alkyl which may substitute on the aryl or heteroaryl, for example, methyl, ethyl, propyl, isopropyl, butyl, isobutyl, tert-butyl, pentyl and isopentyl can be named.

As the lower alkenyl which may substitute on the aryl or heteroaryl, for example, vinyl, 1-propenyl, allyl, isopropenyl, 3-butenyl, 2-butenyl, 1-butenyl, 1-methyl-allyl, 1-methyl-1-propenyl, 1-ethyl-1-vinyl, 2-methyl-allyl, 2-methyl-1-propenyl, 3-methyl-2-butenyl and 4-pentenyl can be named.

As the lower alkynyl which may substitute on the aryl or heteroaryl, for example, ethynyl, 1-propynyl, 2-propynyl, 1-methyl-2-propynyl, 1-butynyl, 2-butynyl, 1-methyl-2-butynyl, 1-pentynyl, 3-pentynyl, 4-pentynyl and 1-hexynyl can be named.

As the lower cycloalkyl which may substitute on the aryl or heteroaryl, for example, cyclopropyl, cyclopentyl and cyclohexyl can be named.

The halogenated lower alkyl which may substitute on the aryl or heteroaryl signify lower alkyl substituted with one or more halogen atoms, such as chloromethyl, dichloromethyl, trichloromethyl, fluoromethyl, difluoromethyl, trifluoromethyl, chloroethyl, dichloroethyl, 1,2-difluoroethyl, 2,2-difluoroethyl and 2,2,2-trifluoroethyl.

As the lower alkylamino which may substitute on the aryl or heteroaryl, for example, methylamino, ethylamino, propylamino, isopropylamino, butylamino, sec-butylamino and tert-butylamino can be named.

As the di-lower alkylamino which may substitute on the aryl or heteroaryl, for example, dimethylamino, diethylamino, ethylmethylamino, dipropylamino, methylpropylamino and diisopropylamino can be named.

As the lower alkylthio which may substitute on the aryl or heteroaryl, for example, methylthio, ethylthio and propylthio can be named.

As the lower alkylsulfonyl which may substitute on the aryl or heteroaryl, for example, methylsulfonyl, ethylsulfonyl and propylsulfonyl can be named.

As the optionally fluorine-substituted lower alkoxy which may substitute on aryl or heteroaryl, for example, methoxy, ethoxy, propoxy, fluoromethoxy, trifluoromethoxy, 2,2-difluoroethoxy and 2,2,2-trifluoroethoxy can be named.

As the lower acyl which may substitute on the aryl or heteroaryl, for example, formyl, acetyl, propionyl and butyryl can be named.

As the lower acylamino which may substitute on the aryl or heteroaryl, for example, formamido, acetamido and propionylamino can be named.

As the lower alkoxycarbonyl which may substitute on the aryl or heteroaryl, for example, methoxycarbonyl, ethoxycarbonyl and propoxycarbonyl can be named.

As the lower alkylcarbamoyl which may substitute on the aryl or heteroaryl, for example, methylcarbamoyl, ethylcarbamoyl and propylcarbamoyl can be named.

As the di-lower alkylcarbamoyl which may substitute on the aryl or heteroaryl, for example, dimethylcarbamoyl, diethylcarbamoyl and dipropylcarbamoyl can be named.

As the lower alkylsulfamoyl which may substitute on the aryl or heteroaryl, for example, methylsulfamoyl and ethylsulfamoyl may be named.

As the di-lower alkylsulfamoyl which may substitute on the aryl or heteroaryl, for example, dimethylsulfamoyl and diethylsulfamoyl can be named.

As the lower alkylcarbamoyloxy which may substitute on the aryl or heteroaryl, for example, methylcarbamoyloxy can be named.

As the di-lower alkylcarbamoyloxy which may substitute on the aryl or heteroaryl, for example, dimethylcarbamoyloxy can be named.

As the lower alkoxycarbonylamino which may substitute on the aryl or heteroaryl, for example, methoxycarbonylamino and ethoxycarbonylamino can be named.

As the (lower alkylsulfamoyl)amino which may substitute on the aryl or heteroaryl, for example, (methylsulfamoyl)amino and (ethylsulfamoyl)amino can be named.

As the (di-lower alkylsulfamoyl)amino which may substitute on the aryl or heteroaryl, for example, (dimethylsulfamoyl)amino and (diethylsulfamoyl)amino can be named.

As the (lower alkylsulfamoyl)(lower alkyl)amino which may substitute on the aryl or heteroaryl, for example, (methylsulfamoy)methylamino can be named.

As the (di-lower alkylsulfamoyl)(lower alkyl)amino which may substitute on the aryl or heteroaryl, for example, (dimethylsulfamoyl)methylamino can be named.

As the (lower alkylsulfonyl)amino which may substitute on the aryl or heteroaryl, for example, methylsulfonylamino, ethylsulfonylamino and propylsulfonylamino can be named.

As the (lower alkylcarbamoyl)amino which may substitute on the aryl or heteroaryl, for example, (methylcarbamoyl)amino and (ethylcarbamoyl)amino can be named.

As the (di-lower alkylcarbamoyl)amino which may substitute on the aryl or heteroaryl, for example, (dimethylcarbamoyl)amino and (diethylcarbamoyl)amino can be named.

As the aryl or heteroaryl optionally having these various substituents (i.e., $R^6$), specifically the following can be named for example:

halogenated aryl or heteroaryl such as 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2,3-dichlorophenyl, 3,4-dichlorophenyl, 3,5-dichlorophenyl, 4-chloro-2-fluorophenyl, 2-chloro-3-pyridyl, 5-fluoro-3-pyridyl, 5-bromo-3-pyridyl, 5-chloro-3-pyridyl, 6-chloro-3-pyridyl, 6-fluoro-3-pyridyl, 6-bromo-3-pyridyl, 5,6-dichloro-3-pyridyl and 5-chloro-2-pyrazinyl;

cyano-containing aryl or heteroaryl such as 2-cyanophenyl, 3-cyanophenyl, 4-cyanophenyl and 5-cyano-3-pyridyl;

nitro-containing aryl or heteroaryl such as 2-nitrophenyl, 3-nitrophenyl and 4-nitrophenyl;

aryl or heteroaryl having a lower alkyl substituent such as 2-tolyl, 3-tolyl, 4-tolyl, 2-ethylphenyl, 3-ethylphenyl, 4-ethylphenyl, 2-isopropylphenyl, 3-isopropylphenyl, 2-isopropylphenyl, 3-isopropylphenyl, 4-isopropylphenyl, 4-methyl-3-pyridyl, 5-methyl-3-pyridyl and 5-methyl-2-pyrazinyl;

aryl or heteroaryl having a lower alkenyl substituent such as 2-vinylphenyl, 3-vinylphenyl, 4-vinylphenyl and 5-vinyl-3-pyridyl;

aryl or heteroaryl having a lower alkynyl substituent such as 2-ethynylphenyl, 3-ethynylphenyl, 4-ethynylphenyl, 5-ethynyl-3-pyridyl, 2-(1-propynyl)phenyl, 3-(1-propynyl)phenyl, 5-(1-propynyl)-3-pyridyl, 3-(1-butynyl)phenyl, 5-(1-butynyl)-3-pyridyl and 5-(1-hexynyl)-3-pyridyl;

aryl or heteroaryl having a $C_3$–$C_6$ cycloalkyl substituent such as 3-cyclopropylphenyl, 3-cyclohexylphenyl and 5-cyclopropyl-3-pyridyl;

aryl or heteroaryl having a halogenated lower alkyl substituent such as 3-(chloromethyl)phenyl, 4-(chloromethyl)phenyl, 2-(trifluoromethyl)phenyl, 3-(trifluoromethyl)phenyl, 4-(trifluoromethyl)phenyl, 2-chloro-3-(trifluoromethyl)phenyl and 5-(trifluoromethyl)-3-pyridyl;

aryl or heteroaryl having a lower alkylamino substituent, such as 2-(methylamino)phenyl, 3-(methylamino)phenyl, 4-(methylamino)phenyl and 2-(methylamino)-3-pyridyl;

aryl or heteroaryl having a di-lower alkylamino substituent such as 2-(dimethylamino)phenyl, 3-(dimethylamino)phenyl, 4-(dimethylamino)phenyl and 2-(dimethylamino)-3-pyridyl;

aryl or heteroaryl having a lower alkylthio substituent, such as 2-(methylthio)phenyl, 3-(methylthio)phenyl, 4-(methylthio)phenyl, 2-(methylthio)-3-pyridyl and 2-(propylthio)-3-pyridyl;

aryl or heteroaryl having a lower alkylsulfonyl substituent such as 2-(methylsulfonyl)phenyl, 3-(methylsulfonyl)phenyl, 4-(methylsulfonyl)phenyl and 2-(methylsulfonyl)-3-pyridyl;

aryl or heteroaryl having a lower alkoxy substituent which is optionally substituted with fluorine, such as 2-methoxyphenyl, 3-methoxyphenyl, 4-methoxyphenyl, 2-(trifluoromethoxy)phenyl, 3-(trifluoromethoxy)phenyl, 4-(trifluoromethoxy)phenyl, 2-ethoxyphenyl, 3-ethoxyphenyl, 4-ethoxyphenyl, 2-methoxy-3-pyridyl, 2,6-dimethoxy-3-pyridyl and 5-(trifluoromethoxy)-3-pyridyl;

aryl or heteroaryl having a lower acyl substituent such as 2-acetylphenyl, 3-acetylphenyl and 4-acetylphenyl;

aryl or heteroaryl having a lower acylamino substituent such as 2-acetamidophenyl, 3-acetamidophenyl and 4-acetamidophenyl;

aryl or heteroaryl having a lower alkoxycarbonyl substituent such as 2-(methoxycarbonyl)phenyl, 3-(methoxycarbonyl)phenyl, 4-(methoxycarbonyl)phenyl and 5-(methoxycarbonyl)-3-pyridyl;

aryl or heteroaryl having a carbamoyl substituent, such as 2-carbamoylphenyl, 3-carbamoylphenyl, 4-carbamoylphenyl and 2-carbamoyl-3-pyridyl.

aryl or heteroaryl having a lower alkylcarbamoyl substituent such as 2-(methylcarbamoyl)phenyl, 3-(methylcarbamoyl)phenyl, 4-(methylcarbamoyl)phenyl and 2-(methylcarbamoyl)-3-pyridyl;

aryl or heteroaryl having a di-lower alkylcarbamoyl substituent such as 2-(dimethylcarbamoyl)phenyl, 3-(dimethylcarbamoyl)phenyl, 4-(dimethylcarbamoyl)phenyl and 2-(dimethylcarbamoyl)-3-pyridyl;

aryl or heteroaryl having a sulfamoyl group such as 2-sulfamoylphenyl, 3-sulfamoylphenyl, 4-sulfamoylphenyl and 2-sulfamoyl-3-pyridyl;

aryl or heteroaryl having a lower alkylsulfamoyl substituent such as 2-(methylsulfamoyl)phenyl, 3-(methylsulfamoyl)phenyl, 4-(methylsulfamoyl)phenyl and 2-(methylsulfamoyl)-3-pyridyl;

aryl or heteroaryl having a di-lower alkylsulfamoyl substituent such as 2-(dimethylsulfamoyl)phenyl, 3-(dimethylsulfamoyl)phenyl, 4-(dimethylsulfamoyl)-phenyl and 2-(dimethylsulfamoyl)-3-pyridyl;

aryl or heteroaryl having a lower alkylcarbamoyloxy substituent such as 2-(methylcarbamoyloxy)phenyl, 3-(methylcarbamoyloxy)phenyl and 4-(methylcarbamoyloxy)phenyl;

aryl or heteroacryl having a di-lower alkylcarbamoyloxy substituent such as 2-(dimethylcarbamoyloxy)phenyl, 3-(dimethylcarbamoyloxy)phenyl and 4-(dimethylcarbamoyloxy)phenyl;

aryl or heteroaryl having a lower alkoxycarbonylamino substituent such as 2-(methoxycarbonylamino)phenyl, 3-(methoxycarbonylamino)phenyl, 4-(methoxycarbonylamino)phenyl and 2-(methoxycarbonylamino)-3-pyridyl;

aryl or heteroaryl having a lower alkylsulfamoylamino substituent such as 2-(methylsulfamoylamino)phenyl, 3-(methylsulfamoylamino)phenyl, 4-(methylsulfamoylamino)phenyl and 2-(methylsulfamoylamino)-3-pyridyl;

aryl or heteroaryl having a di-lower alkylsulfamoylamino substituent such as 2-(dimethylsulfamoylamino)phenyl, 3-(dimethylsulfamoylamino)phenyl, and 4-(dimethylsulfamoylamino)phenyl;

aryl or heteroaryl having a (lower alkylsulfamoyl)(lower alkyl)amino substituent such as 2-[(methylsulfamoyl)methylamino]phenyl, 3-[(methylsulfamoyl)methylamino]phenyl and 4-[(methylsulfamoyl)methylamino]phenyl;

aryl or heteroaryl having a (di-lower alkylsulfamoyl)(lower alkyl)amino substituent such as 2-[(dimethylsulfamoylmethylamino]phenyl, 3-[(dimethylsulfamoyl)methylamino]phenyl and 4-[(dimethylsulfamoyl)methylamino]phenyl;

aryl or heteroaryl having a lower alkylsulfonylamino substituent, such as 2-(methylsulfonylamino)phenyl, 3-(methylsulfonylamino)phenyl, 4-(methylsulfonylamino)phenyl and 2-(methylsulfonylamino)-3-pyridyl;

aryl or heteroaryl having a lower alkylcarbamoylamino substituent, such as 2-(methylcarbamoylamino)phenyl, 3-(methylcarbamoylamino)phenyl and 4-(methylcarbamoylamino)phenyl;

aryl or heteroaryl having a di-lower alkylcarbamoylamino substituent, such as 2-(dimethylcarbamoylamino)phenyl, 3-(dimethylcarbamoylamino)phenyl and 4-(dimethylcarbamoylamino)phenyl; and aryl or heteroaryl having a phenoxy group, such as 2-phenoxyphenyl, 3-phenoxyphenyl, 4-phenoxyphenyl and 2-phenoxy-3-pyridyl.

Of such examples of $R^6$, phenyl, 1-naphthyl, 2-naphthyl, 2-tolyl, 3-tolyl, 4-tolyl, 2-fluorophenyl, 3-fluorophenyl, 4-fluorophenyl, 2-chlorophenyl,3-chlorophenyl, 4-chlorophenyl, 2,3-dichlorophenyl, 3,4-dichlorophenyl, 3,5-dichlorophenyl, 3-bromophenyl, 4-bromophenyl, 4-chloro-2-fluorophenyl, 3-iodophenyl, 4-iodophenyl, 2-(trifluoromethyl)phenyl, 3-(trifluoromethyl)phenyl, 4-(trifluoromethyl)phenyl, 2-(trifluoromethoxy)phenyl, 3-(trifluoromethoxy)phenyl, 4-(trifluoromethoxy)phenyl, 4-nitrophenyl, 2-(dimethylamino)phenyl, 3-(dimethylamino)phenyl, 2-cyanophenyl, 3-cyanophenyl, 2-(acetamido)phenyl, 3-(acetamido)phenyl, 3-(chloromethyl)phenyl, 2-methoxyphenyl, 3-methoxyphenyl, 2-(phenoxy)phenyl, 3-(phenoxy)phenyl, pyrazinyl, 5-chloro-2-pyrazinyl, 5-methyl-2-pyrazinyl, 2-pyridyl, 3-pyridyl, 4-pyridyl, 2-chloro-3-pyridyl, 5-chloro-3- pyridyl, 6-chloro-3-pyridyl, 6-fluoro-3-pyridyl, 6-bromo-3-pyridyl,chloro-2-pyridyl, 5,6-dichloro-3-pyridyl, 5-fluoro-3-pyridyl, 5-bromo-3-pyridyl, 3–5,6-difluoro-3-pyridyl, 5-cyano-3-pyridyl, 4-methyl-3-pyridyl, 5-methyl-3-pyridyl, 5-(trifluoromethyl)-3-pyridyl, 5-(1-butynyl)-3-pyridyl, 5-(1-hexynyl)-3-pyridyl, 2-methoxy-3-pyridyl, 5-methoxy-3-pyridyl, 2-phenoxy-3-pyridyl, 2-(methylthio)-3-pyridyl, 2-methyl-5-pyridyl, 3-bromo-5-pyridyl, 2,6-dimethoxypyridyl, 2-(propylthio)-3-pyridyl, 2-thienyl, 3-thienyl, 2-quinolyl, 3-quinolyl and 4-quinolyl are preferred.

Inter alia, phenyl, 3-tolyl, 3-chlorophenyl, 4-chlorophenyl, 3-bromophenyl, 3-fluorophenyl, 3-cyanophenyl, 3,5-dichloropheny, 4-(trifluoromethoxy)phenyl, 5-chloro-3-pyridyl, 5-fluoro-3-pyridyl, 5-bromo-3-pyridyl, 5-cyano-3-pyridyl, pyrazinyl and 3-pyridyl are recommended.

As examples of specific compounds which are represented by the general formula [I], those of the following structures can be shown, in which the compounds having asymmetric carbons are mixtures of stereoisomers, unless specified otherwise.

STRUCTURAL EXAMPLE 1

Structural example 1

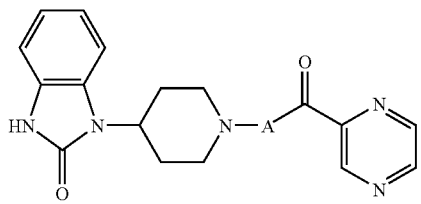

As A:

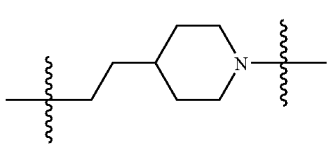

(1)

-continued

Structural example 1

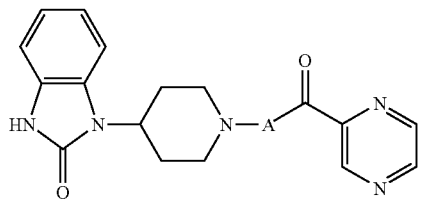

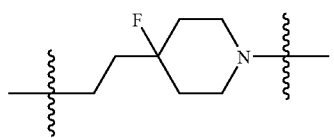

(2)

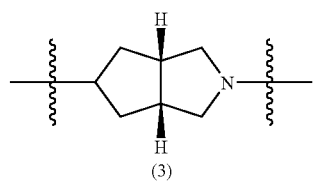

(3)

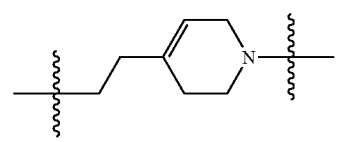

(4)

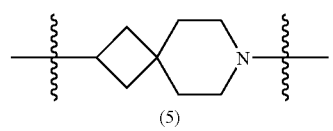

(5)

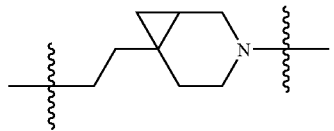

(6)

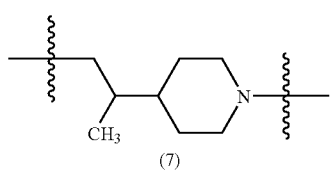

(7)

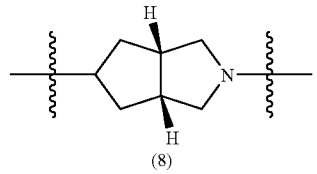

(8)

Structural example 1
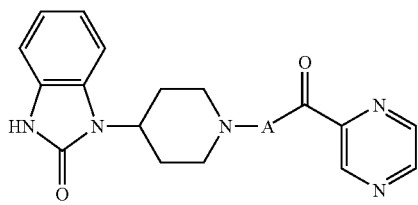
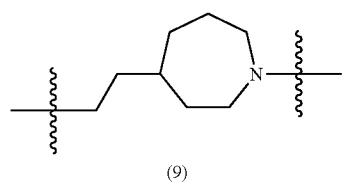
(9)
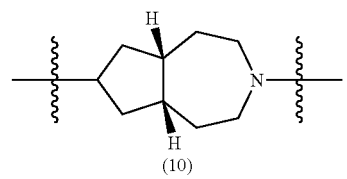
(10)
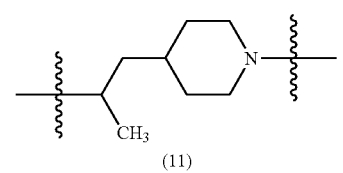
(11)
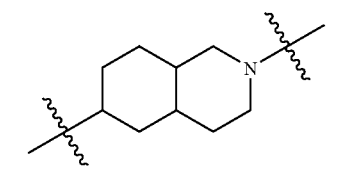
(12)
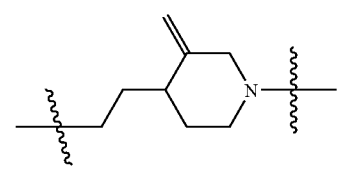
(13)
STRUCTURAL EXAMPLE 2
Structural example 2
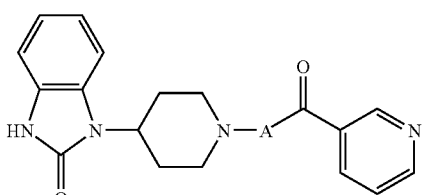
As A:
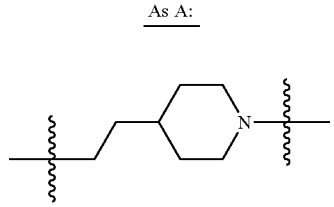
(14)
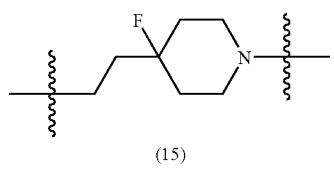
(15)
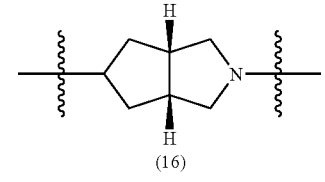
(16)
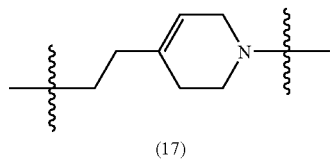
(17)
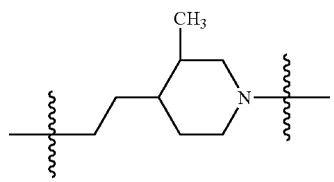
(18)
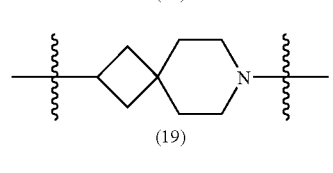
(19)
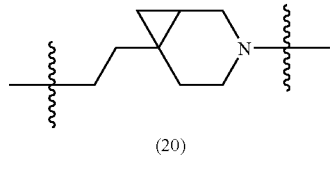
(20)

-continued
Structural example 2
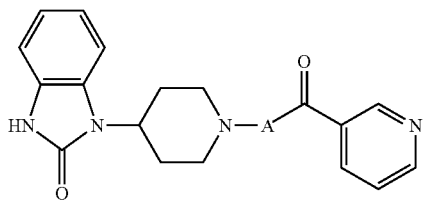
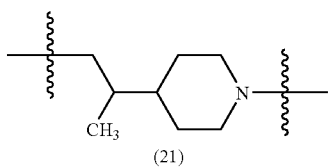
(21)
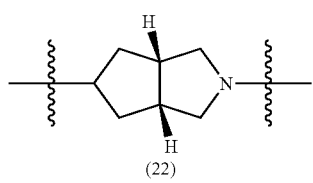
(22)
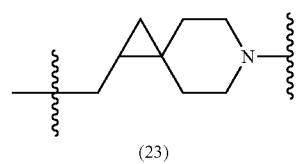
(23)
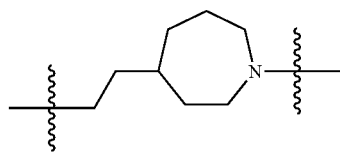
(24)
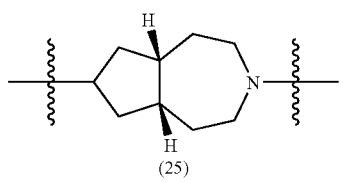
(25)
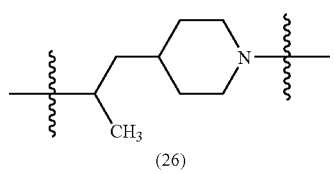
(26)
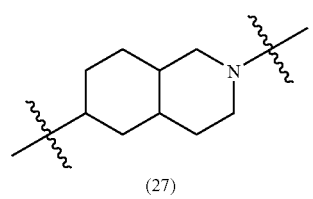
(27)
-continued
Structural example 2
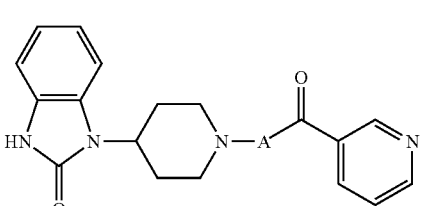
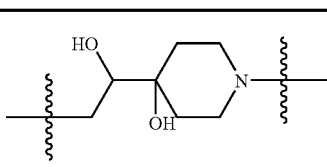
(28)
STRUCTURAL EXAMPLE 3
Structural example 3
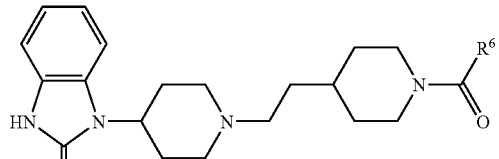
As R⁶:
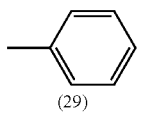
(29)
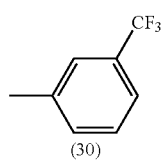
(30)
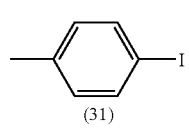
(31)
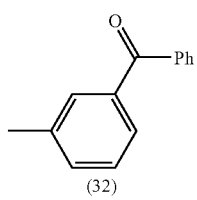
(32)

-continued
Structural example 3
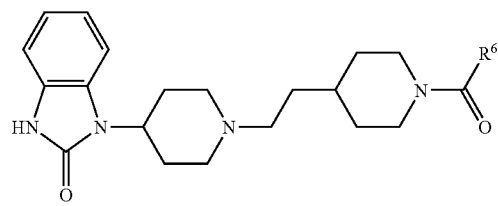
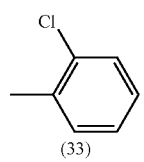
(33)
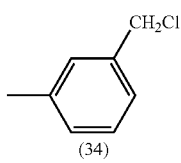
(34)
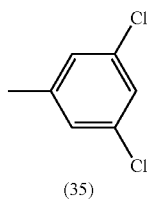
(35)
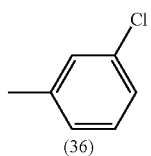
(36)
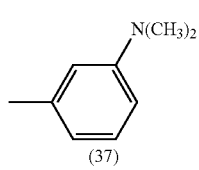
(37)
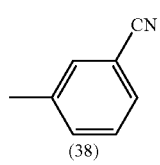
(38)
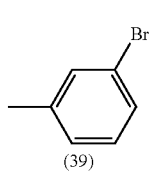
(39)
-continued
Structural example 3
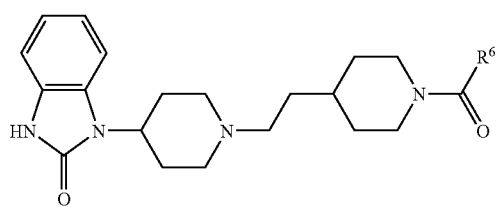
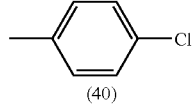
(40)
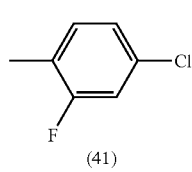
(41)
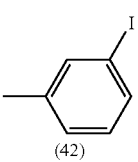
(42)
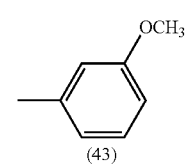
(43)
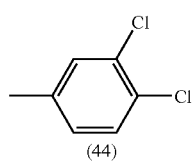
(44)
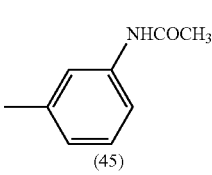
(45)

STRUCTURAL EXAMPLE 4
Structural example 4
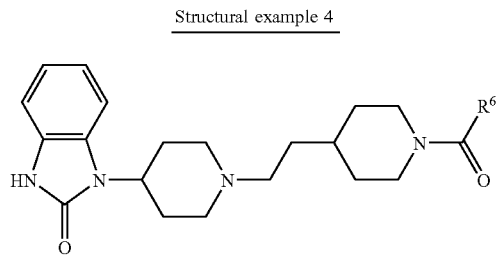
As R⁶:
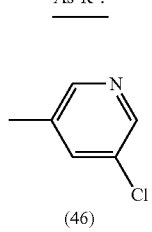
(46)
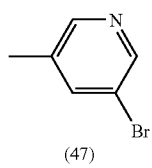
(47)
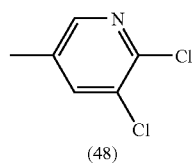
(48)
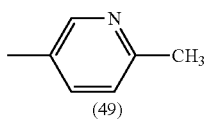
(49)
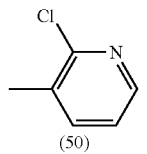
(50)
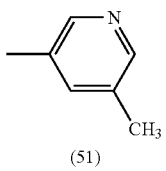
(51)
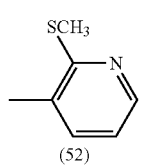
(52)
Structural example 4 -continued
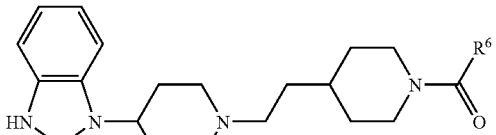
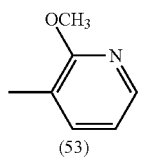
(53)
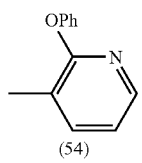
(54)
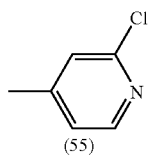
(55)
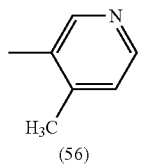
(56)
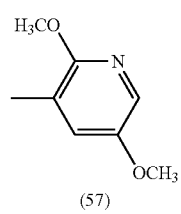
(57)
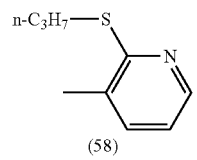
(58)
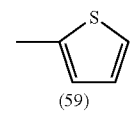
(59)
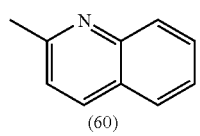
(60)

-continued
Structural example 4
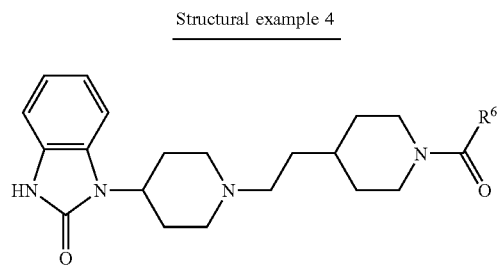
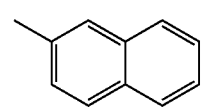
(61)
STRUCTURAL EXAMPLE 5
Structural example 5
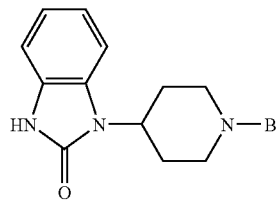
As B:
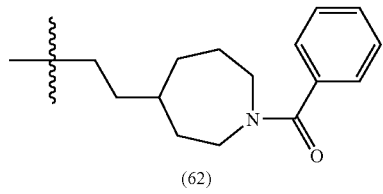
(62)
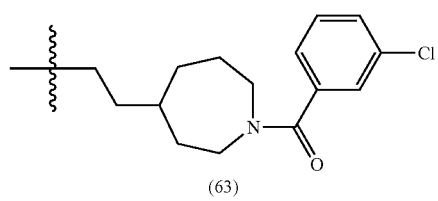
(63)
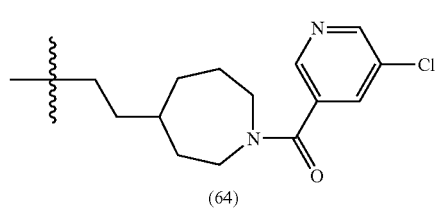
(64)
-continued
Structural example 5
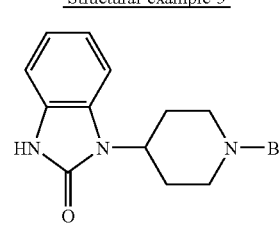
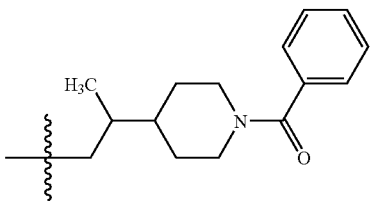
(65)
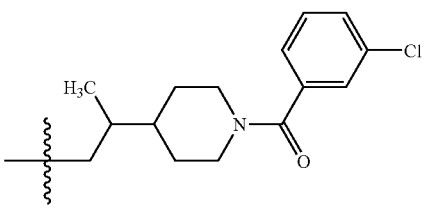
(66)
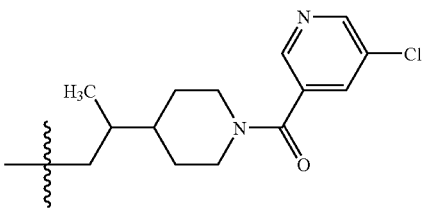
(67)
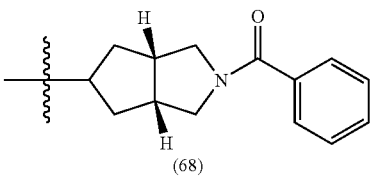
(68)
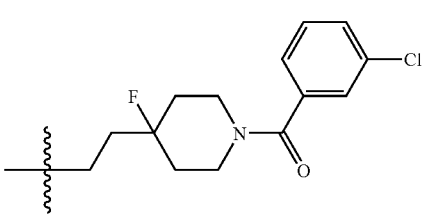
(69)
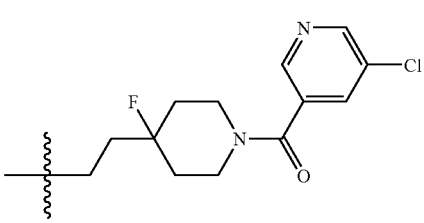
(70)

STRUCTURAL EXAMPLE 6
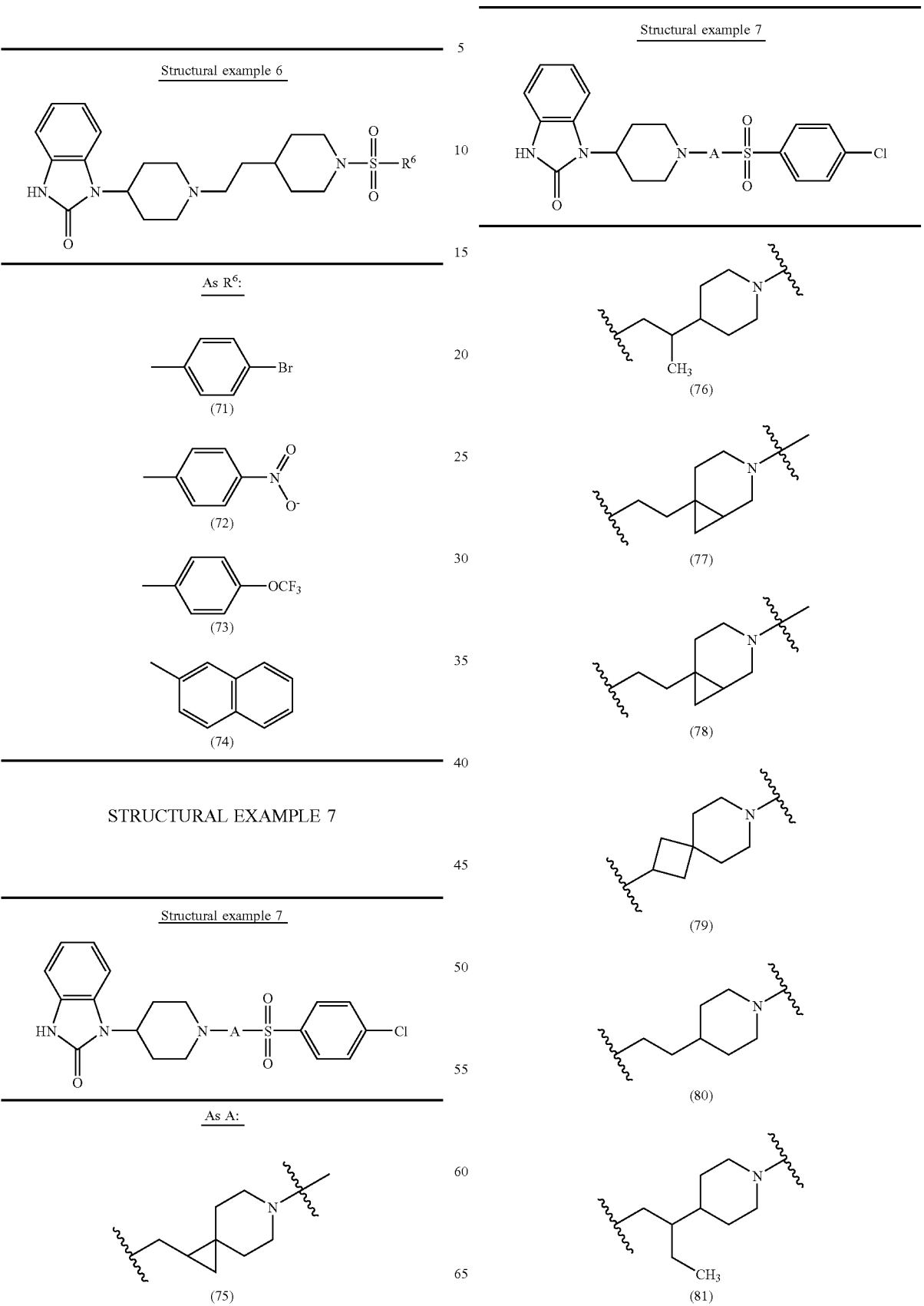

-continued
Structural example 7
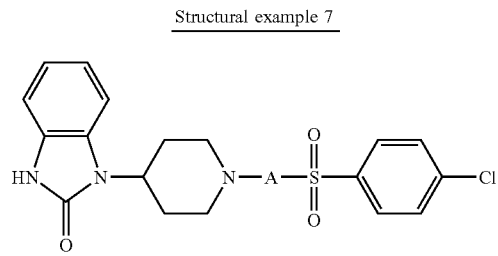
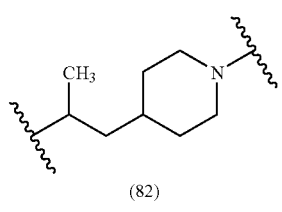
(82)
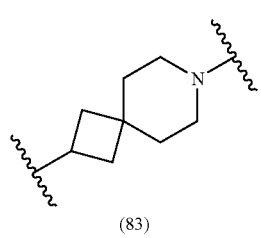
(83)
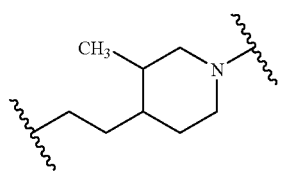
(84)
STRUCTURAL EXAMPLE 8
Structural example 8
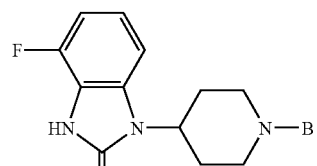
As B:
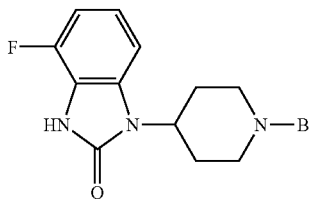
(85)
-continued
Structural example 8
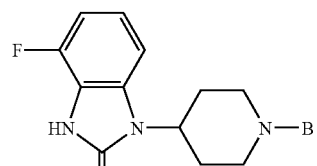
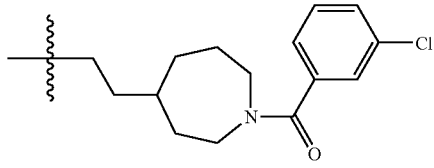
(86)
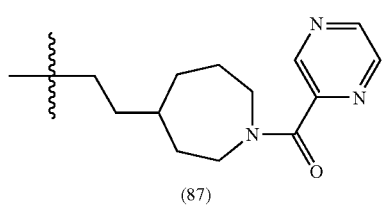
(87)
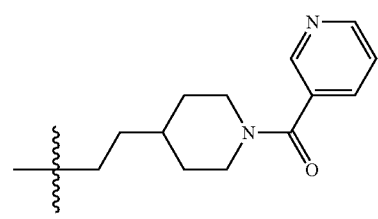
(88)
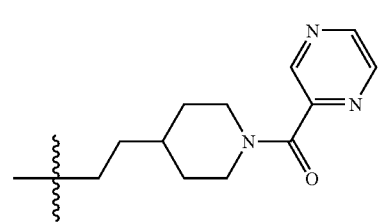
(89)
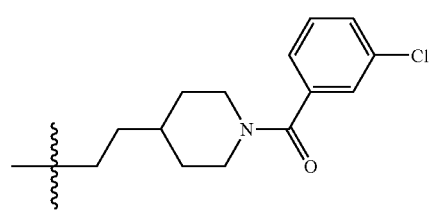
(90)
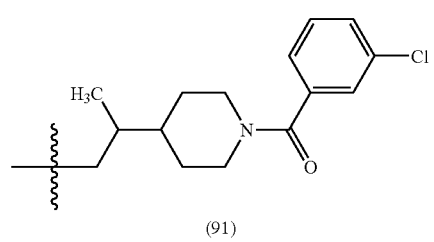
(91)

-continued
Structural example 8
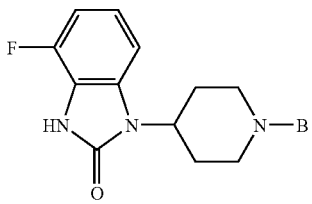
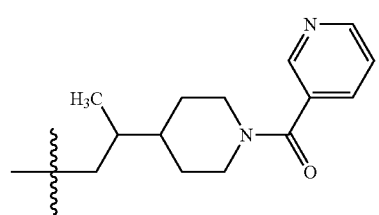
(92)
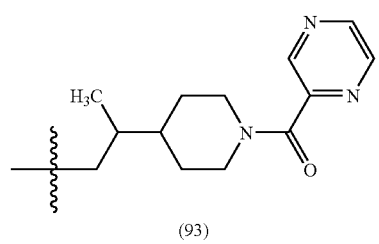
(93)
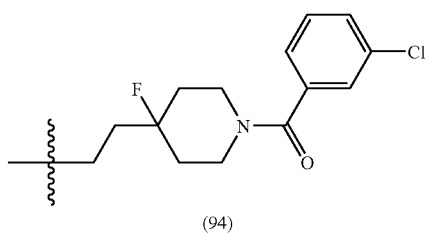
(94)
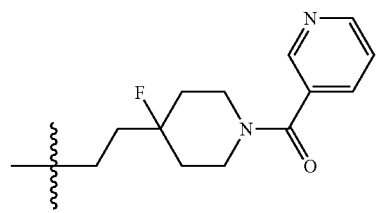
(95)
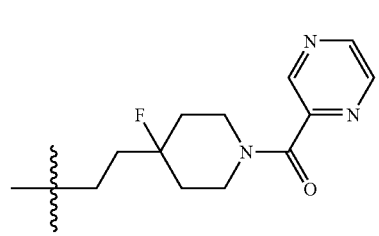
(96)
-continued
Structural example 8
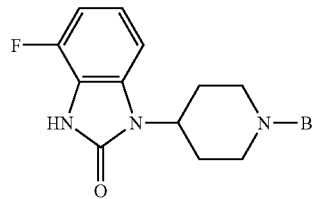
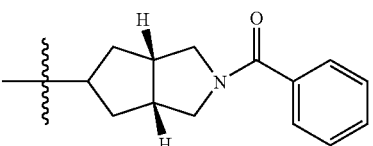
(97)
STRUCTURAL EXAMPLE 9
Structured example 9
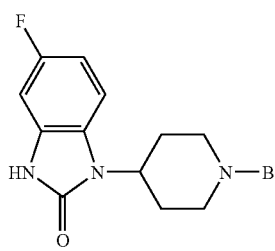
As B:
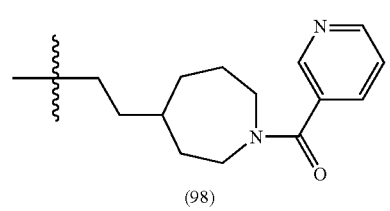
(98)
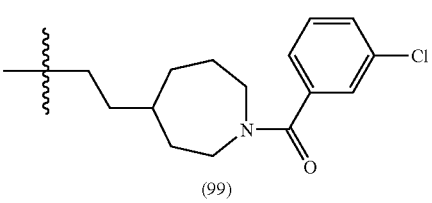
(99)
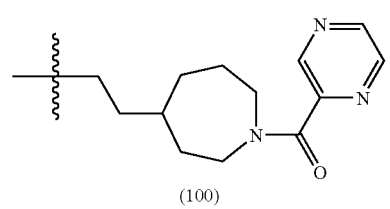
(100)

-continued
Structured example 9
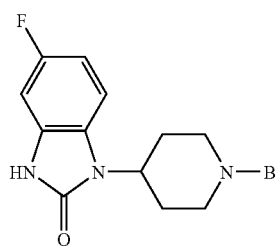
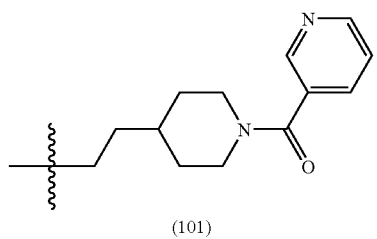
(101)
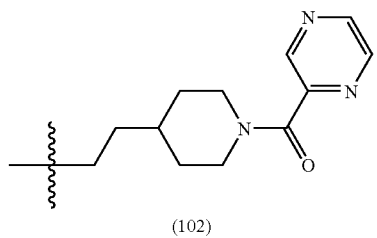
(102)
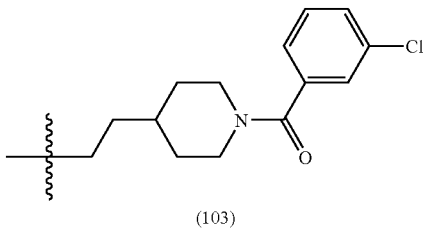
(103)
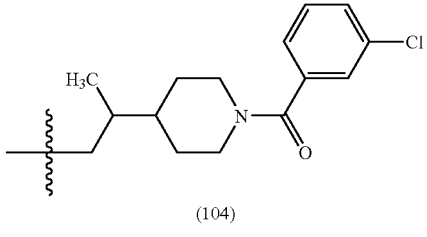
(104)
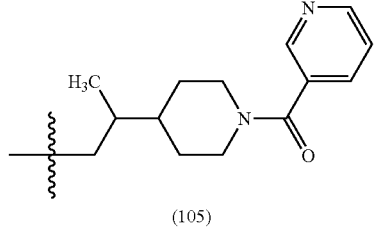
(105)
-continued
Structured example 9
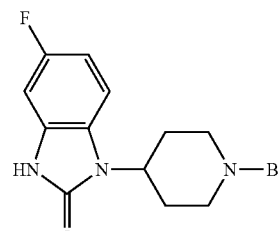
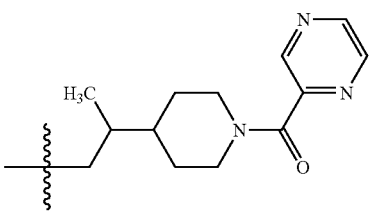
(106)
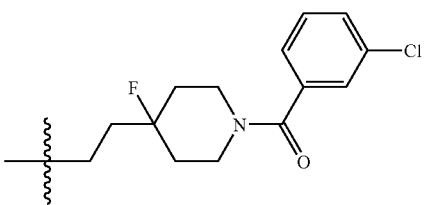
(107)
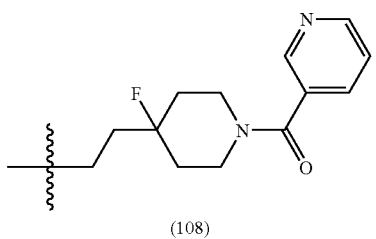
(108)
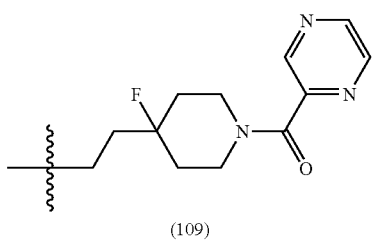
(109)
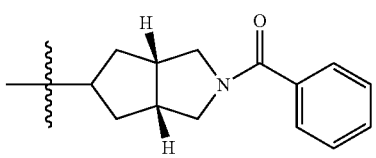
(110)
Of the benzimidazolone derivatives represented by the general formula [I], those preferred are:
1-[1-[2-(1-benzoylpiperidin-4-yl)ethyl]piperidin-4-yl]-1,3-dihydro-2H-benzimidazol-2-one,
1-[1-[2-[1-(4-chlorophenylsulfonyl)piperidin-4-yl]ethyl]piperidin-4-yl]-1,3-dihydro-2H-benzimidazol-2-one, 1-[1-[2-[1-[4-(trifluoromethoxy)phenylsulfonyl]piperidin-4-yl]ethyl]-piperidin-4-yl]-1,3-dihydro-2H-benzimidazol-2-one,
1-[1-[2-[1-(pyrazinylcarbonyl)piperidin-4-yl]ethyl]piperidin-4-yl]-1,3-dihydro-2H-benzimidazol-2-one,
1-[1-[2-[1,2,5,6-tetrahydro-1-(pyrazinylcarbonyl)-4-pyridyl]ethyl]-piperidin-4-yl]-1,3-dihydro-2H-benzimidazol-2-one,
1-[1-[2-[1-(pyrazinylcarbonyl)-3-methylene-piperidin-4-yl]ethyl]-piperidin-4-yl]-1,3-dihydro-2H-benzimidazol-2-one,
(S*)-1-[1-[2-[1-(pyrazinylcarbonyl)perhydroazepin-4-yl]ethyl]-piperidin-4-yl]-1,3-dihydro-2H-benzimidazol-2-one,
(R*)-1-[1-[2-[1-(pyrazinylcarbonyl)perhydroazepin-4-yl]ethyl]-piperidin-4-yl]-1,3-dihydro-2H-benzimidazol-2-one,
(S*)-1-[1-[2-[1-(3-pyridylcarbonyl)perhydroazepin-4-yl]ethyl]-piperidin-4-yl]-1,3-dihydro-2H-benzimidazol-2-one,
(R*)-1-[1-[2-[1-(3-pyridylcarbonyl)perhydroazepin-4-yl]ethyl]-piperidin-4-yl]-1,3-dihydro-2H-benzimidazol-2-one,
1-[1-[2-[1-(pyrazinylcarbonyl)piperidin-4-yl]propyl]piperidin-4-yl]-1,3-dihydro-2H-benzimidazol-2-one,
1-[1-[2-[1-(3-pyridylcarbonyl)piperidin-4-yl]propyl]piperidin-4-yl]-1,3-dihydro-2H-benzimidazol-2-one,
1-[1-[2-[1-(3-chlorobenzoyl)piperidin-4-yl]propyl]piperidin-4-yl]-1,3-dihydro-2H-benzimidazol-2-one,
1-[1-[2-[1-(3-pyridylcarbonyl)piperidin-4-yl]-1-methylethyl]piperidin-4-yl]-1,3-dihydro-2H-benzimidazol-2-one,
1-[1-[2-hydroxy-2-[4-hydroxy-1-(3-pyridylcarbonyl)piperidin-4-yl]-ethyl]piperidin-4-yl]-1,3-dihydro-2H-benzimidazol-2-one,
1-[1-[2-[1-(2-chlorobenzoyl)piperidin-4-yl]ethyl]-piperidin-4-yl]-1,3-dihydro-2H-benzimidazol-2-one,
1-[1-[2-[1-(3-chlorobenzoyl)piperidin-4-yl]ethyl]-piperidin-4-yl]-1,3-dihydro-2H-benzimidazol-2-one,
1-[1-[2-[1-(3-bromobenzoyl)piperidin-4-yl]ethyl]-piperidin-4-yl]-1,3-dihydro-2H-benzimidazol-2-one,
1-[1-[2-[1-(3-iodobenzoyl)piperidin-4-yl]ethyl]-piperidin-4-yl]-1,3-dihydro-2H-benzimidazol-2-one,
1-[1-[2-[1-(3,5-dichlorobenzoyl)piperidin-4-yl]ethyl]-piperidin-4-yl]-1,3- dihydro-2H-benzimidazol-2-one,
1-[1-[2-[1-(3,4-dichlorobenzoyl)piperidin-4-yl]ethyl]-piperidin-4-yl]-1,3-dihydro-2H-benzimidazol-2-one,
1-[1-[2-[1-(3-pyridylcarbonyl)piperidin-4-yl]ethyl]-piperidin-4-yl]-1,3-dihydro-2H-benzimidazol-2-one,
1-[1-[2-[1-[(5-chloro-3-pyridyl)carbonyl]piperidin-4-yl]ethyl]-piperidin-4-yl]-1,3- dihydro-2H-benzimidazol-2-one,
1-[1-[2-[1-[(4,5-dichloro-3-pyridyl)carbonyl]piperidin-4-yl]ethyl]-piperidin-4-yl]-1,3- dihydro-2H-benzimidazol-2-one,
1-[1-[2-[1-[(5-bromo-3-pyridyl)carbonyl]piperidin-4-yl]ethyl]-piperidin-4-yl]-1,3- dihydro-2H-benzimidazol-2-one,
1-[1-[2-[1-(2-thenoyl)piperidin-4-yl]ethyl]-piperidin-4-yl]-1,3-dihydro-2H-benzimidazol-2-one,
1-[1-[2-[1-(3-pyridylcarbonyl)piperidin-4-yl]ethyl]-piperidin-4-yl]-5-fluoro-1,3-dihydro-2H-benzimidazol-2-one,
1-[1-[2-(1-pyrazinylcarbonylpiperidin-4-yl)ethyl]-piperidin-4-yl]-5-fluoro-1,3-dihydro-2H-benzimidazol-2-one,
1-[1-[2-[1-[(5,6-dichloro-3-pyridyl)carbonyl]-piperidin-4-yl]ethyl]-piperidin-4-yl]-1,3-dihydro-2H-benzimidazol-2-one,
1-[1-[2-[1-[(2-propylthio-3-pyridyl)carbonyl]piperidin-4-yl]ethyl]-piperidin-4-yl]-1,3-dihydro-2H-benzimidazol-2-one,
1-[1-[2-[4-fluoro-1-(pyrazinylcarbonyl)piperidin-4-yl]propyl]piperidin-4-yl]-1,3-dihydro-2H-benzimidazol-2-one,
1-[1-[2-[4-fluoro-1-(3-pyridylcarbonyl)piperidin-4-yl]propyl]piperidin-4-yl]-1,3-dihydro-2H-benzimidazol-2-one,
1-[1-[(1α,5α,7β)-3-(pyrazinylcarbonyl)-3-azabicyclo[3.3.0]octan-7-yl]-piperidin-4-yl]-1,3-dihydro-2H-benzimidazol-2-one,
1-[1-[(1α,5α,7α)-3-(pyrazinylcarbonyl)-3-azabicyclo[3.3.0]octan-7-yl]-piperidin-4-yl]-1,3-dihydro-2H-benzimidazol-2-one,
1-[1-[(1α,5α,7β)-3-(3-pyridylcarbonyl)-3-azabicyclo[3.3.0]octan-7-yl]-piperidin-4-yl]-1,3-dihydro-2H-benzimidazol-2-one,
1-[1-[(1α,5α,7α)-3-(3-pyridylcarbonyl)-3-azabicyclo[3.3.0]octan-7-yl]-piperidin-4-yl]-1,3-dihydro-2H-benzimidazol-2-one,
1-[1-[(1α,7α,9β)-4-(pyrazinylcarbonyl)-4-azabicyclo[5.3.0]nonan-9-yl]-piperidin-4-yl]-1,3-dihydro-2H-benzimidazol-2-one,
1-[1-[2-[7-(3-pyridylcarbonyl)-7-azaspiro[3.5]nonan-2-yl]ethyl]-piperidin-4-yl]-1,3-dihydro-2H-benzimidazol-2-one,
1-[1-[2-[7-(pyrazinylcarbonyl)-7-azaspiro[3.5]nonan-2-yl]ethyl]-piperidin-4-yl]-1,3-dihydro-2H-benzimidazol-2-one, and
1-[1-[[6-(3-pyridylcarbonyl)-6-azaspiro[2.5]octan-1-yl]methyl]-piperidin-4-yl]-1,3-dihydro-2H-benzimidazol-2-one.

Production Methods of the Compounds Represented by the General Formula [I]

Compounds of the present invention can be prepared, for example, by the following production methods 1–5.

Production Method 1

Production method 1 comprises a two-stage reaction in which amine is condensed with aldehyde or ketone, and either successively or simultaneously reduced (hereafter it is occasionally referred to as "reductive alkylation"), the scheme being as illustrated by the following formulae.

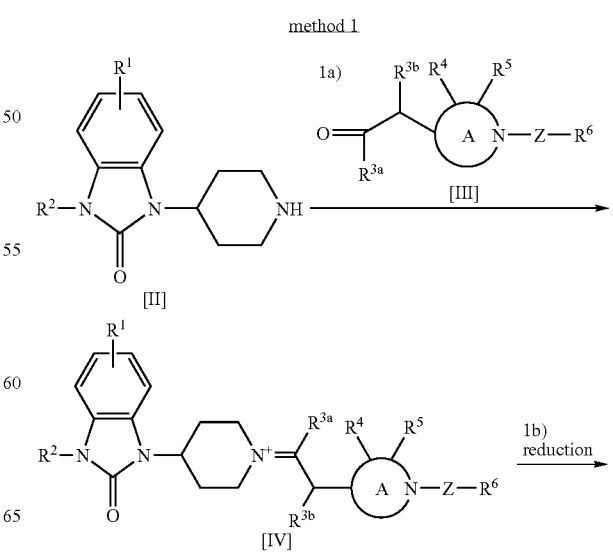

-continued

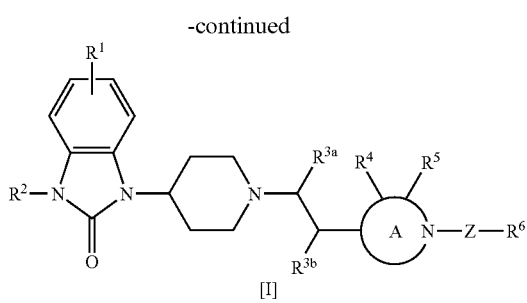

[I]

in which $R^1$, $R^2$, $R^{3a}$, $R^{3b}$, $R^4$, $R^5$, $R^6$, Z and A ring are same as earlier defined.

The process comprises, as specific steps, 1a) a step of reacting (condensing) a compound of the general formula [III] with a compound of the general formula [III], to form a compound of the general formula [IV], and 1b) a step of reducing (reducing the nitrogen-carbon double bond) the compound of the general formula [IV] which is obtained in the step 1a).

This reaction constitutes a method preferred in the cases where $R^{3a}$ and $R^{3b}$ are hydrogen or lower alkyl, or $R^3$ ($R^{3a}$ or $R^{3b}$) and $R^4$ form, together with the carbons to which they bind, a 3- to 6-membered carbocyclic ring.

In the occasion of said reaction, functional group(s) not participating in the reaction, where present, can be protected during the series of the reactions where necessary, and deprotected after the reduction.

As such functional groups, for example, amine, ketone, aldehyde, alcohol and the like can be named. As protective groups of amine, aralkyl such as benzyl, p-methoxybenzyl, 3,4-dimethoxybenzyl, o-nitrobenzyl, p-nitrobenzyl, benzhydryl and trityl; $C_1$–$C_6$ alkanoyl such as formyl, acetyl, propionyl, butyryl and pivaloyl; arylalkanoyl such as benzoyl, phenylacetyl and phenoxyacetyl; lower alkoxycarbonyl such as methoxycarbonyl, ethoxycarbonyl, propoxycarbonyl and tert-butoxycarbonyl; aralkyloxycarbonyl such as benzyloxycarbonyl, p-nitrobenzyloxycarbonyl and phenethyloxycarbonyl; trialkylsilyl such as trimethylsilyl and tert-butyldimethylsilyl; and phthaloyl are named, in particular, tert-butoxycarbonyl and benzyloxycarbonyl being preferred.

Also as protective groups of ketone or aldehyde, acetals and ketals such as ethyleneacetal, trimethyleneacetal, ethyleneketal and trimethyleneketal are named.

As protective groups of alcohol, trialkylsilyl such as trimethylsilyl, tert-butyldimethylsilyl and tert-butyldiphenylsilyl; lower alkoxymethyl such as methoxymethyl and 2-methoxyethoxymethyl; tetrahydropyranyl; trimethylsilylethoxymethyl; aralkyl such as benzyl, p-methoxybenzyl, 2,3-dimethoxybenzyl, o-nitrobenzyl, p-nitrobenzyl and trityl; and acyl such as formyl and acetyl are named, in particular, methoxymethyl, tetrahydropyranyl, trityl, trimethylsilylethoxymethyl, tert-butyldimethylsilyl and acetyl being preferred.

Method for introduction/removal of the protective group(s) differs depending on the kind of the protective group and stability of obtained compound. Whereas, for example, those methods described in literature [cf. *Protective Groups in Organic Synthesis*, T. W. Greene, John Wiley & Sons Co. (1981)] or methods analogous thereto can be followed to conduct the introduction/removal.

Step 1a)

The reaction of step 1a) is conducted by mixing a compound of the general formula [II] with a compound of the general formula [III] in reaction solvent. Where necessary, the reaction can be conducted in the presence of a desiccant such as anhydrous magnesium sulfate, anhydrous sodium sulfate or the like, or using Dean-Stark desiccator.

As the use rates of the compounds of the general formulae [II] and [III], 0.5–5.0 moles, preferably 1.1–2.0 moles, of the compound of the general formula [III] is used per mole of the compound of the general formula [II].

As the reaction solvent, for example, alcohols such as methanol, ethanol, propanol and 2-propanol; ethers such as ethyl ether, tetrahydrofuran and 1,4-dioxane; esters such as ethyl acetate; halogenated hydrocarbons such as methylene chloride, chloroform and 1,2-dichloroethane; aromatic hydrocarbons such as benzene, toluene, chlorobenzene and xylene; aprotic polar solvents such as N,N-dimethylformamide, acetonitrile and hexamethylphosphoric triamide; or mixed solvents of the foregoing can be named.

As the reaction temperature, for example it can be 0–150° C., preferably 10–110° C., and the reaction terminates in 5 minutes–48 hours.

After termination of the step 1a) reaction, the compound of the general formula [IV] may be isolated, purified and then subjected to the step 1b), or the step 1b) can be conducted using the reaction liquid containing the compound of the general formula [IV] which is obtained from the step 1a) reaction as it is, or the step 1a) and step 1b) may be conducted simultaneously.

In particular, compounds of the general formula [IV] may have unstable structures difficult of isolation, depending on the kinds of the substituents ($R^1$–$R^6$). In such a case, it is preferred to conduct the step 1b) without isolation and purification, or to conduct the steps 1a) and 1b) simultaneously.

Step 1b)

By reducing the nitrogen-carbon double bond in the compound of the general formula [IV] as obtained in the step 1a), a benzimidazolone derivative of the general formula [I] is obtained.

As a method of the reduction, for example, reduction using a metal hydride compound or hydrogenation using hydrogen gas in the presence of a metal catalyst can be adopted. As useful metal hydride compound, for example, lithium borohydride, sodium borohydride, zinc cyanoborohydride, sodium cyanoborohydride and sodium triacetoxyborohydride can be named. In particular, where such a reducing agent as sodium borohydride, sodium cyanoborohydride, zinc cyanoborohydride or sodium triacetoxyborohydride, which preferentially reduces imine/enamine, is used, benzimidazolone derivatives represented by the general formula [I] can be obtained in single step, by conducting the reaction of the step 1a) in the presence of such a reducing agent.

Where a metal hydride complex is used as the reducing agent, the use rate of the reducing agent is normally 0.25–30 moles, preferably 1.5–10 moles, per mole of the compound of the general formula [IV] or [II].

Exemplary reaction temperature ranges −20–100° C., preferably 0–50° C., and the reaction terminates normally in 1–24 hours.

In the hydrogenation method by contacting hydrogen gas in the presence of a metal catalyst, known metal catalyst, e.g., palladium-carbon, Raney nickel, palladium hydroxide-carbon and the like can be used. Its use rate is normally 0.01–1000 wt parts, preferably 1.0–50 wt parts, per 100 wt parts of the compound of the general formula [IV].

Exemplary hydrogen pressure in the hydrogenation reaction ranges from ambient pressure to 5 atmospheres; exemplary reaction temperature ranges 0–100° C., preferably 10–50° C.; and the reaction terminates normally in 5 minutes–24 hours.

In said reducing reaction, solvent may be suitably used depending on the kind of reducing agent and form of reaction, examples of useful solvent including alcohols such as methanol, ethanol, isopropyl alcohol and tert-butyl alcohol; ethers such as diethyl ether, diisopropyl ether, dibutyl ether, 1,2-dimethoxyethane, 1,4-dioxane, tetrahydrofuran and diglyme; esters such as ethyl acetate; aliphatic hydrocarbons such as pentane, hexane, heptane and cyclohexane; aromatic hydrocarbons such as benzene and toluene; inert solvent such as water; and mixed solvents of the foregoing.

As compounds of the general formula [II], these which are commercially available can be used. They can furthermore be easily prepared following the methods described in, e.g., International Publication WO 96/13262.

As specific examples of the compound represented by the general formula [II],
1-(piperidin-4-yl)-1,3-dihydro-2H-benzimidazol-2-one,
4-methyl-1-(piperidin-4-yl)-1,3-dihydro-2H-benzimidazol-2-one,
4-ethyl-1-(piperidin-4-yl)-1,3-dihydro-2H-benzimidazol-2-one,
4-propyl-1-(piperidin-4-yl)-1,3-dihydro-2H-benzimidazol-2-one,
4-methoxy-1-(piperidin-4-yl)-1,3-dihydro-2H-benzimidazol-2-one,
4-ethoxy-1-(piperidin-4-yl)-1,3-dihydro-2H-benzimidazol-2-one,
4-fluoro-1-(piperidin-4-yl)-1,3-dihydro-2H-benzimidazol-2-one,
4-chloro-1-(piperidin-4-yl)-1,3-dihydro-2H-benzimidazol-2-one,
5-methyl-1-(piperidin-4-yl)-1,3-dihydro-2H-benzimidazol-2-one,
5-ethyl-1-(piperidin-4-yl)-1,3-dihydro-2H-benzimidazol-2-one,
5-propyl-1-(piperidin-4-yl)-1,3-dihydro-2H-benzimidazol-2-one,
5-methoxy-1-(piperidin-4-yl)-1,3-dihydro-2H-benzimidazol-2-one,
5-ethoxy-1-(piperidin-4-yl)-1,3-dihydro-2H-benzimidazol-2-one,
5-chloro-1-(piperidin-4-yl)-1,3-dihydro-2H-benzimidazol-2-one,
5-fluoro-1-(piperidin-4-yl)-1,3-dihydro-2H-benzimidazol-2-one,
6-methyl-1-(piperidin-4-yl)-1,3-dihydro-2H-benzimidazol-2-one,
6-ethyl-1-(piperidin-4-yl)-1,3-dihydro-2H-benzimidazol-2-one,
6-propyl-1-(piperidin-4-yl)-1,3-dihydro-2H-benzimidazol-2-one,
6-methoxy-1-(piperidin-4-yl)-1,3-dihydro-2H-benzimidazol-2-one,
6-ethoxy-1-(piperidin-4-yl)-1,3-dihydro-2H-benzimidazol-2-one,
6-chloro-1-(piperidin-4-yl)-1,3-dihydro-2H-benzimidazol-2-one,
6-fluoro-1-(piperidin-4-yl)-1,3-dihydro-2H-benzimidazol-2-one,
7-methyl-1-(piperidin-4-yl)-1,3-dihydro-2H-benzimidazol-2-one,
7-ethyl-1-(piperidin-4-y)-1,3-dihydro-2H-benzimidazol-2-one,
7-propyl-1-(piperidin-4-yl)-1,3-dihydro-2H-benzimidazol-2-one,
7-methoxy-1-(piperidin-4-yl)-1,3-dihydro-2H-benzimidazol-2-one,
7-ethoxy-1-(piperidin-4-yl)-1,3-dihydro-2H-benzimidazol-2-one,
7-chloro-1-(piperidin-4-yl)-1,3-dihydro-2H-benzimidazol-2-one,
7-fluoro-1-(piperidin-4-yl)-1,3-dihydro-2H-benzimidazol-2-one,
3-methyl-1-(piperidin-4-yl)-1,3-dihydro-2H-benzimidazol-2-one, and
3-benzyl-1-(piperidin-4-yl)-1,3-dihydro-2H-benzimidazol-2-one can be named.

Compounds represented by the general formula [III] can be prepared, for example, by the following methods.

Production Method of Compounds Represented by the General Formula [III]

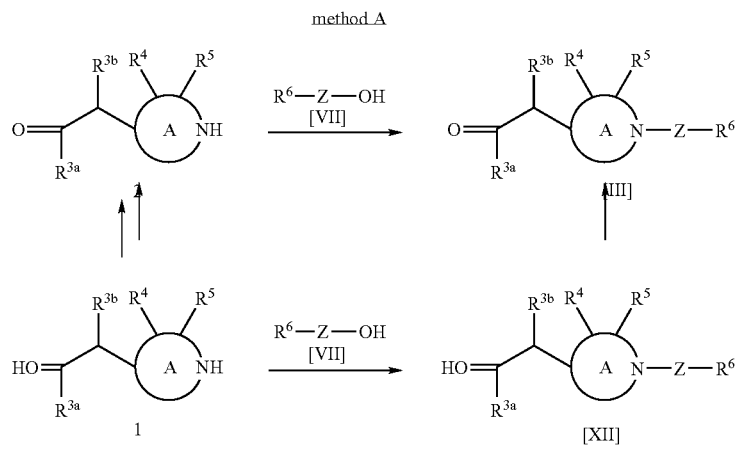

Compound 1 is oxidized to form compound 2. The oxidation is conducted by known methods, using oxidizing agent such as pyridinium chlorochromate, chromium trioxide, pyridinium dichromate, mangagese dioxide, sulfur trioxide-pyridine complex, oxalyl chloride/dimethylsulfoxide and the like. In that occasion, the amine may be protected by a protective group in advance of the oxidation, and later the protective group may be removed. Then the compound 2 is reacted with carboxylic acid or sulfonic acid represented by the general formula [VII] in the manner following the later described step 2d), to form a compound represented by the general formula [III].

It is also possible to react compound 1 with the carboxylic acid or sulfonic acid of the general formula [VII] to form a compound of a general formula [XII], and to form a compound of the general formula [III] by oxidizing thus formed compound of the formula [XII]. As the reaction conditions, those earlier described can be used.

As examples of compound 1, piperidine-4-ethanol, 3-methylene-piperidine-4-ethanol, 1,2,5,6-tetrahydropyridine-4-ethanol, 2-(perhydroazepin-4-yl)ethanol, 2-(piperidin-4-yl)-1-propanol, 1-(piperidin-4-yl)-2-propanol, 3-azabicyclo[3.3.0]octan-7-ol and 7-azaspiro[3,5]nonan-2-ol can be named. Commercial products of these compounds can be used, or they can be prepared by known methods of synthesis or following the methods as described in production examples given later.

Production Method 2

Production method 2 comprises a 4-stage reaction, whose scheme is shown by the following formulae.

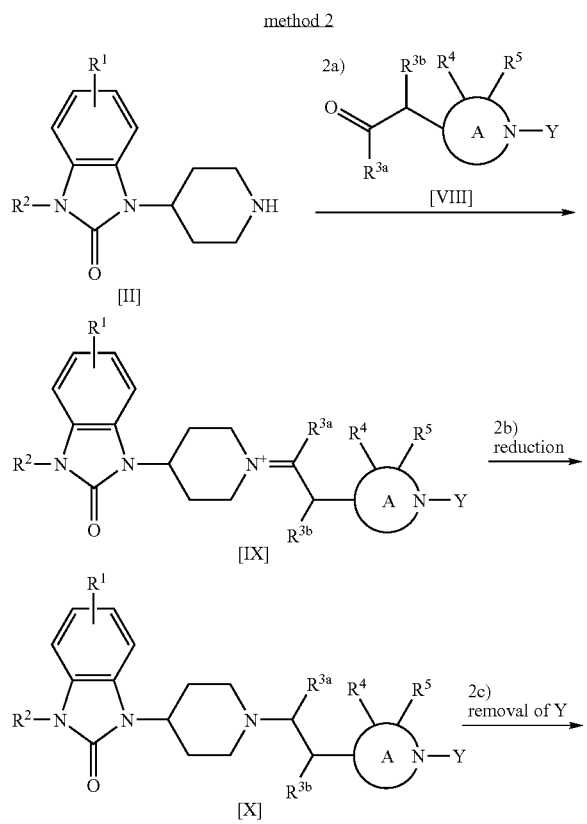

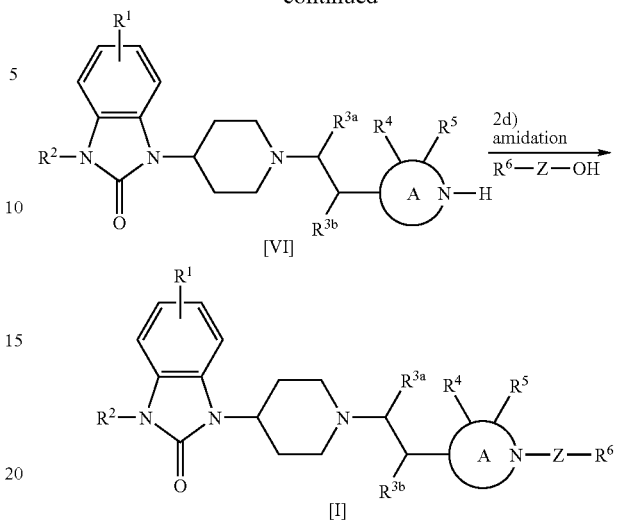

In the above formulae, Y stands for amino-protective group; $R^1$, $R^2$, $R^{3a}$, $R^{3b}$, $R^4$, $R^5$, $R^6$, Z and A ring are same as earlier defined.

As the specific steps:

2a) a step of reacting a compound of the general formula [II] with a compound of the general formula [VIII] to form a compound of the general formula [IX];

2b) a step of reducing the nitrogen-carbon double bond in the compound of the general formula [IX] as obtained in the step 2a) to form a compound of the general formula [X];

2c) a step of removing the protective group Y in the compound of the general formula [X] as obtained in the step 2b) to form a compound of the general formula [VI]; and 2d) a step of reacting (amidating) the compound of the general formula [VI] as obtained in the step 2c) with carboxylic acid or sulfonic acid of the general formula [VII], $R^6$-Z-OH [VII]

or activated derivative thereof to form a compound of the general formula [I].

Said reactions constitute a production method particularly favorable where $R^{3a}$ and $R^{3b}$ are hydrogen or lower alkyl, or $R^3$ ($R^{3a}$ or $R^{3b}$) and $R^4$ together form a 3- to 6-membered carbocyclic ring, in combination with the carbon atoms to which they bind.

In the compounds represented by the general formula [VIII], as the amino-protective group Y, for example, aralkyl such as benzyl, p-methoxybenzyl, 3,4-dimethoxybenzyl, o-nitrobenzyl, p-nitrobenzyl, benzhydryl and trityl; $C_1$–$C_6$ alkanoyl such as formyl; arylalkanoyl such as phenylacetyl and phenoxyacetyl; lower alkoxycarbonyl such as methoxycarbonyl, ethoxycarbonyl, propoxycarbonyl, tert-butoxycarbonyl, trichloroethyloxycarbonyl, trimethylsilylethyloxycarbonyl and 9-fluorenylmethyloxycarbonyl; and aralkyloxycarbonyl such as benzyloxycarbonyl, p-nitrobenzyloxycarbonyl and phenethyloxycarbonyl can be named, among which benzyloxycarbonyl and tert-butoxycarbonyl being particularly recommendable.

Step 2a)

The reaction of a compound of the general formula [II] with a compound of the general formula [VIII] is conducted under the reaction conditions following those for the step 1a) of the production method 1, to form a compound of the general formula [IX].

Step 2b)

The compound of the general formula [IX] as obtained in the step 2a) is reduced as in the step 1b) in the production method 1 to form a compound represented by the general formula [XI].

Step 2c)

The protective group Y in the compound of the general formula [X] as obtained in the step 2b) is removed to provide an amine [VI].

Methods of removing the protective group Y differ depending on the kind of said group and stability of individual object compound [I]. The removal is conducted following those methods, for example, described in literature *[Protective Groups in Organic Synthesis*, T.W. Greene, John Wiley & Sons (1981)] or methods analogous thereto, by solvolysis using acid or base (e.g. hydrolysis using from 0.01 mole to large excess of an acid, preferably trifluoroacetic acid, formic acid, hydrochloric acid or the like; hydrolysis using from equimolar to large excess of a base, preferably potassium hydroxide, calcium hydroxide or the like); chemical reduction using metal hydride complex, or hydrogenolysis (catalytic reduction) using palladium-carbon catalyst, palladium hydroxide, Raney nickel catalyst, and the like.

More specifically, aralkyl such as benzyl, p-methoxybenzyl, 3,4-dimethoxybenzyl, o-nitrobenzyl, p-nitrobenzyl, benzhydryl and trityl are removed by catalytic reduction; $C_1-C_6$ alkanoyl such as formyl and pivaloyl are removed with hydrochloric acid, hydrazine or the like; benzoyl or the like are removed with potassium hydroxide solution; lower alkoxycarbonyl such as methoxycarbonyl, ethoxycarbonyl, propoxycarbonyl and tert-butoxycarbonyl are removed with hydrochloric acid, trifluoroacetic acid and the like; and aralkyloxycarbonyl such as benzyloxycarbonyl, p-nitrobenzyloxycarbonyl and phenethyloxycarbonyl are removed by catalytic reduction.

Step 2d)

This is an amidation reaction of the compound as obtained in the step 2c) with carboxylic acid or sulfonic acid of the general formula [VII]

$R^6$-Z-OH  [VII]

or activated derivative thereof, to form a benzimidazolone derivative represented by the general formula [I]. The carboxylic acid or sulfonic acid represented by the general formula [VII] may be those which are commercially available, or they can be readily prepared by the methods described in *Organic Functional Group Preparations*, 2nd edition, S. R. Sandler, Academic Press (1983), etc.

In this production method, the four stages of the reaction using a compound of the general formula [II] as the starting material can be continuously conducted, or the method may be started from the step 2b), step 2c) or step 2d), using as the starting materials, respectively, a separately synthesized compound of the general formula [IX], a separately synthesized compound of the general formula [X] or a separately synthesized compound of the general formula [VI].

Where the compound of the general formula [VII] is a carboxylic acid, as its activated derivatives, those known per se can be used, for example, anhydride of the carboxylic acid, anhydride mixture of the carboxylic acid with other acid(s), carboxylic acid lower alkyl ester, acyl halide derived from the carboxylic acid, thiol ester of the carboxylic acid (i.e., S-alkyl ester of thiocarboxylic acid) or activated ester of the carboxylic acid.

As the mixed acid anhydride of the carboxylic acid with other acid(s), for example, those of the carboxylic acid and ethyl monocarbonate or isobutyl monocarbonate can be named, and as examples of the carboxylic acid lower alkyl ester, methyl ester, ethyl ester, etc. of the carboxylic acid can be named.

As the carboxylic acid-derived acyl halide, for example, acyl chloride, acyl bromide and the like can be named.

As S-alkyl ester of thiocarboxylic acid, for example, S-methyl ester, S-ethyl ester, S-tert-butyl ester, S-phenyl ester and S-(2-pyridyl) ester of thiocarboxylic acid can be named.

S-alkyl esters of thiocarboxylic acid can be prepared following, for example, those methods as described in *Chem. Lett.*, 1981, p. 133 or *Heterocycles*, Vol. 33, pp. 131–134 (1992), using corresponding carboxylic acids as the starting materials.

As activated esters of carboxylic acid, for example, esters of carboxylic acid with phenols such as 2,4,5-trichlorophenol, pentachlorophenol, pentafluorophenol, 2-nitrophenol and 4-nitrophenol; or with hydroxyl derivatives such as N-hydroxysuccinimide, 1-hydroxybenztriazole, N-hydroxypiperidine, N-hydroxy-5-norbornene-2,3-dicarboxyimide and N-hydroxyphthalimide can be named. These activated esters can be obtained through esterification of carboxylic acid with hydroxyl derivatives, in the presence of condensing agent such as dicyclohexyl carbodiimide, 1-ethyl-3-(3-(dimethylamino)propyl)carbodiimide or the like.

As such activated carboxylic acid derivatives, those which are commercially available can be used, or they can be prepared from the carboxylic acid by known methods (e.g., "Fundamentals and Experiments of Peptide Synthesis" Nobuo IZUMIYA, et al., Maruzen Co., 1983).

As specific examples of the carboxylic acid represented by the general formula [VII], benzoic acid, 2-chlorobenzoic acid, 3-chlorobenzoic acid, 3-bromobenzoic acid, 3-iodobenzoic acid, 3-methoxybenzoic acid, 3-trifluoromethylbenzoic acid, 3-chloromethylbenzoic acid, 3-acetamidobenzoic acid, 3-dimethylaminobenzoic acid, 3-cyanobenzoic acid, 3-benzoylbenzoic acid, 4-chlorobenzoic acid, 4-iodobenzoic acid, 3,4-dichlorobenzoic acid, 3,5-dichlorobenzoic acid, 2-fluoro-4-chlorobenzoic acid, 2-pyridinecarboxylic acid, 3-pyridinecarboxylic acid (nicotinic acid), 2-chloropyridine-3-carboxylic acid, 2-thiomethylpyridine-3-carboxylic acid, 2-thiopropylpyridine-3-carboxylic acid, 2-methoxypyridine-3-carboxylic acid, 5-chloropyridine-3-carboxylic acid, 5-bromopyridine-3-carboxylic acid, 4-methylpyridine-3-carboxylic acid, 5-methylpyridine-3-carboxylic acid, 6-methylpyridine-3-carboxylic acid, 3-pyridinecarboxylic acid, 5,6-dichloropyridine-3-carboxylic acid, 2-phonoxypyridine-3-carboxylic acid, 4-pyridinecarboxylic acid, 2-chloropyridine-4-carboxylic acid, thiophene-2-carboxylic acid, naphthalene-1-carboxylic acid and the like can be named. Of those, preferably 3-pyridinecarboxylic acid and pyrazinecarboxylic acid are recommended.

When the compound represented by the general formula [VII] is sulfonic acid, its activated derivatives heretofore known can be used, e.g., anhydride and lower alkyl ester of the sulfonic acid; sulfonyl halide and sulfonyl azide derived from the sulfonic acid; and the like.

As examples of lower alkyl ester of the sulfonic acid, sulfonic acid methyl ester, sulfonic acid ethyl ester and the like can be named.

As examples of sulfonyl halide derived from the sulfonic acid, sulfonyl chloride, sulfonyl bromide and sulfonyl fluoride can be named.

As specific examples of the sulfonic acid represented by the general formula [VII], benzenesulfonic acid, 4-chlorobenzenesulfonic acid, 4-bromobenzenesulfonic acid, 4-nitrobenzenesulfonic acid, 4-trifluorobenzenesulfonic acid, 4-trifluoromethoxybenzenesulfonic acid, 1-naphthalenesulfonic acid, p-toluenesulfonic acid, xylenesulfonic acid and mesitylenesulfonic acid can be named. Of those, preferably benzenesulfonic acid, 4-chlorobenzenesulfonic acid and 4-trifluoromethoxybenzenesulfonic acid are recommended.

As these activated derivatives, those which are commercially available can be used, or they can be prepared by the methods described in, for example, *Organic Functional Group Preparations,* 2nd ed., S. R. Sandler, Academic Press (1983).

The amidation reaction between the carboxylic acid, sulfonic acid or activated derivatives thereof and the amine represented by the general formula [VI] is conducted under heretofore known reaction conditions.

Amidation of the Carboxylic Acid or Activated Derivatives thereof

Where such a carboxylic acid is used in the amidation reaction, the reaction is preferably carried out in the presence of a condensing agent such as carbonyldlimidazole, 1,3-dicyclohexylcarbodiimide, 1-ethyl-3-(3-(dimethylamino)propyl)carbodiimide, diphenylphosphorylazide, dipyridyldisulfide-triphenylphosphine and the like, in particular, 1-ethyl-3-(3-(dimethylamino)propyl)-carbodiimide.

Where a carboxylic acid of the general formula [VII] is used in the amidation reaction, the use rates of the carboxylic acid and amine are: 0.5–2 moles, preferably 0.6–1.0 mole, of the amine of the general formula [VI] is used per mole of the carboxylic acid of the general formula [VII].

While the use rate of said condensing agent is not strictly limited, it is normally used in a range of 1–3 moles, preferably 1.0–1.5 moles, per mole of the carboxylic acid of the general formula [VII].

The reaction is normally conducted in an inert solvent, such as diethyl ether, tetrahydrofuran, N,N-dimethylformamide, dioxane, benzene, toluene, chlorobenzene, methylene chloride, chloroform, carbon tetrachloride, 1,2-dichloroethane, trichloroethylene and the like and mixtures of these solvents. Of these, tetrahydrofuran, N,N-dimethylformamide, 1,4-dioxane, chloroform and methylene chloride are preferred.

The reaction temperature can normally be within a range of 0–150° C., preferably 10–60° C., and the reaction normally terminates in 5 minutes–two days.

The above reaction can be performed in the presence of a base, to smoothly advance the reaction. As the base, those preferred are, for example, inorganic base such as calcium hydroxide, sodium carbonate, potassium carbonate and sodium hydrogencarbonate; or organic base such as triethylamine, ethyldiisopropylamine, pyridine, 4-(dimethylamino) pyridine and N,N-dimethylaniline. When a base is used, its use rate is, for example, within a range of 0.05–10 moles, preferably 0.05–5 moles, per mole of the carboxylic acid of the general formula [VII] or activated derivative thereof.

Whereas, when an activated derivative of the carboxylic acid is used in the amidation reaction, the use rates of the activated derivative of the carboxylic acid and an amine of the general formula [VI] are: 0.5–2 moles, preferably 1.0–1.2 moles, of the activated derivative per mole of the amine of the general formula [VI].

The reaction is normally conducted in an inert solvent such as, for example, halogenated hydrocarbons such as methylene chloride, chloroform, carbon tetrachloride, 1,2-dichloroethane and trichloroethylene; ethers such as ethyl ether, tetrahydrofuran and 1,4-dioxane; esters such as ethyl acetate; aromatic hydrocarbons such as benzene, toluene, chlorobenzene and xylene; aprotic polar solvents such as N,N-dimethylformamide, acetonitrile, acetone and hexamethylphosphoric triamide; or mixed solvents of the foregoing.

As the reaction temperature, −70–150° C., preferably −20–100° C., can be used for example, and the reaction terminates normally within 5 minutes–2 days. Again, the reaction can be conducted in the presence of a base for smooth progress.

As the kind and use rate of the base, the earlier specified can be applied.

When a lower alkyl ester of carboxylic acid or an S-alkyl ester of thiocarboxylic acid is used as the carboxylic acid derivative, the reaction temperature can be made 20–180° C., and the reaction pressure, 1–200 atmospheres.

Amidation of Sulfonic Acid or its Activated Derivative

Where sulfonic acid is used in the reaction, it is desirable to activate it in advance by the means known per se, using an activating agent such as phosphorus pentachloride, phosphoryl chloride, chlorosulfuric acid, thionyl chloride and the like.

Where an activated derivative of sulfonic acid is used in the reaction, use rates of the derivative and the amine of the general formula [VI] are: 0.5–2 moles, preferably 1.0–1.2 moles, of the activated derivative of the sulfonic acid of the general formula [VII] per mole of the amine of the general formula [VI].

The reaction is normally conducted in an inert solvent. As the inert solvent, those customarily used in the occasions of amidating carboxylic acid can similarly be used. The reaction temperatures can be in the range of, for example, −70–150° C., preferably −20–100° C., and normally the reaction terminates within 5 minutes—a day. The reaction can be performed in the presence of a base, to smooth its progress.

The kind and use rate of the base are similar to those as described as to the amidation of the carboxylic acid.

Where a lower alkyl ester of the sulfonic acid is used as the sulfonic acid derivative, a benzimidazolone derivative of the general formula [I] can be obtained by conducting the reaction at temperatures ranging 20–180° C. and pressures of 1–200 atmospheres.

Those compounds represented by the general formula [X] can be prepared, for example, by the following methods besides the one via the above steps 2a) and 2b).

Methods of Producing the Compounds which are Represented by the General Formula [X]

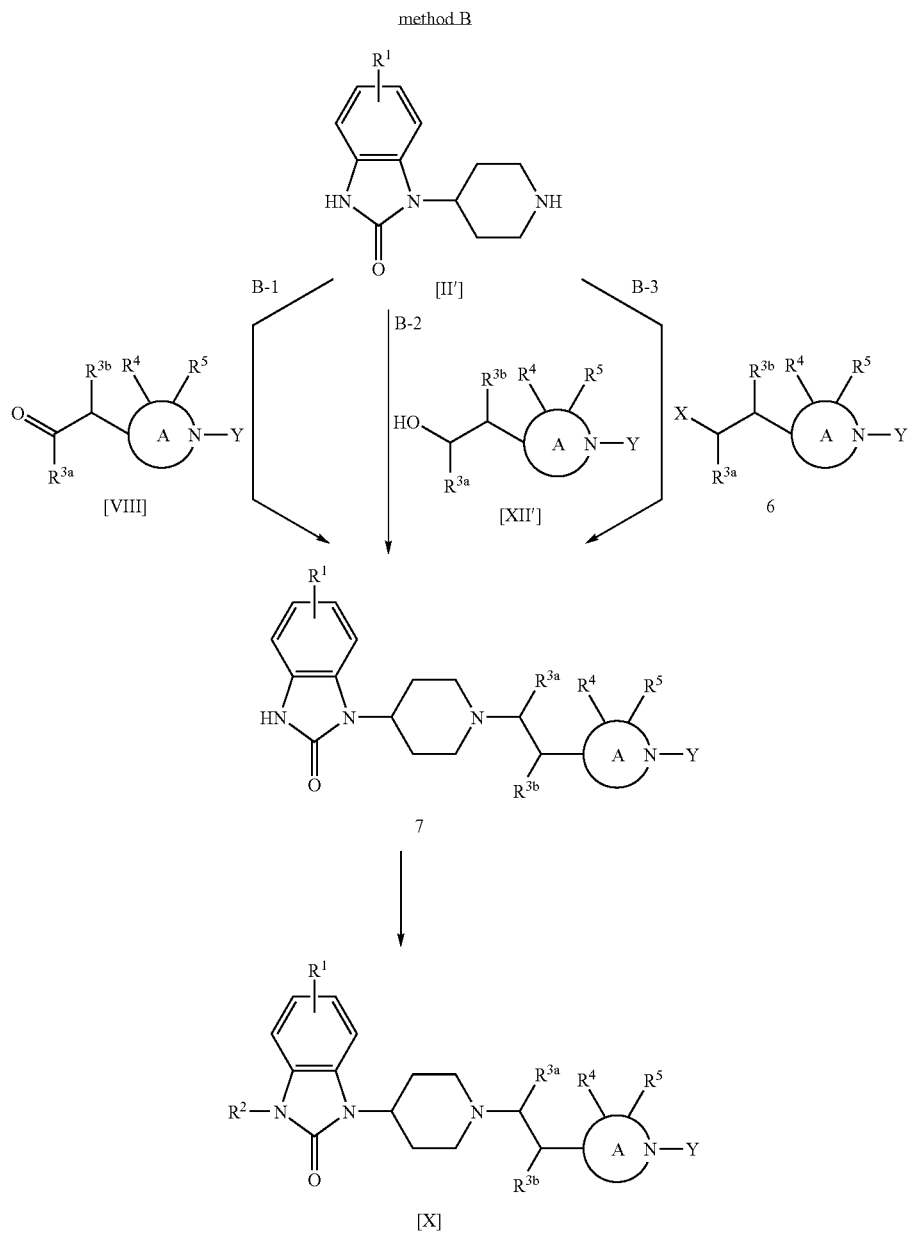

B-1

This reaction uses as the starting material compounds [VIII] instead of those represented by the general formula [III] used in the production method 1, and the reaction conditions same as described as to the production method 1 can be used. Said compounds [VIII] are obtained by protecting the amine in the compound 2 with an amino-protective group Y.

B-2

This reaction uses as the starting material compounds represented by a later described general formula [XII'] instead of the compounds of the general formula [XII] used in the later described production method 4, and the reaction conditions same as described as to the production method 4 can be used. Said compounds of the general formula [XII'] are obtained by protecting the amine in the compound 1 with a protective group Y.

B-3

This reaction uses as the starting material the compound 6 instead of the compounds represented by the general formula [XI] used in the later described production method 3, and the reaction conditions same as described as to the production method 3 can be used. Moreover, the compound 6 can be prepared following the preparation process of the compounds of the general formula [XI] as described in the production method 3.

The compound 7 obtained through the methods B-1 to B-3 can be converted to, where necessary, the corresponding compound of the general formula [X], as alkylated by a means known per se, using lower alkyl halide optionally having phenyl substituent, or alkyl methanesulfonate optionally having phenyl substituent on its alkyl group.

Production Method 3

Production method 3 is one for reacting a compound of the general formula [II] with a compound of the general formula [XI] by a scheme as in the following.

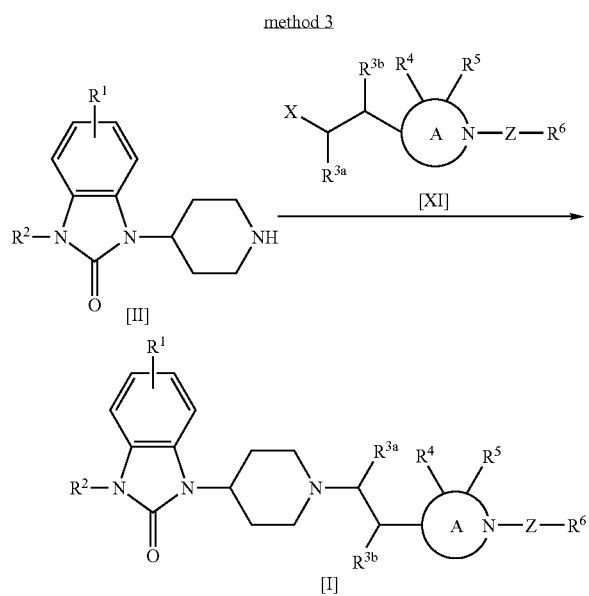

In the formula, X stands for a leaving group. $R^1$, $R^2$, $R^{3a}$, $R^{3b}$, $R^4$, $R^5$, $R^6$, Z and A ring have the earlier given significations.

This reaction is characterized by subjecting a compound of the general formula [II] and a compound of the general formula [XI] to N-alkylation reaction in the optional but preferred presence of base.

Specific examples of the leaving group X in the above formula include halogen such as chlorine, bromine and iodine; organosulfonyloxy such as methylsulfonyloxy, trifluoromethylsulfonyloxy, phenylsulfonyloxy and p-tolylsulfonyloxy; and 1-imidazolyl and the like. Of those, methylsulfonyloxy, phenylsulfonyloxy or p-tolylsulfonyloxy are preferred as the X.

The use rates of the compound of the general formula [II] and that of the general formula [XI] are 0.8–1.5 moles, preferably 0.95–1.2 moles, of the compound of the general formula [XI] per mole of the compound of the general formula [II]. The reaction is carried out in an inert solvent having no detrimental effect on the reaction.

As such an inert solvent, ether such as tetrahydrofuran or 1,4-dioxane; halogenated hydrocarbon such as methylene chloride or chloroform; and aprotic polar solvent such as N,N-dimethylformamide, N,N-dimethylacetamide or acetonitrile can be named for example.

The reaction is preferably conducted in the presence of a base. Examples of the base include organic bases such as triethylamine, diisopropylethylamine, pyridine, 4-dimethylaminopyridine and lithium diisopropylamide; and inorganic bases such as sodium hydride, sodium hydroxide, sodium carbonate, potassium carbonate and sodium hydrogencarbonate.

The use rate of the base is, for example, 1–5 moles, preferably 1.0–3.0 moles, of the base per mole of the compound of the general formula [II].

The reaction temperature normally is within a range of −78–150° C., preferably 0–80° C., and the reaction normally terminates in 5 minutes–7days, preferably 30 minutes–24 hours.

Compounds of the general formula [XI] can be easily prepared by reacting a compound of the general formula [XII] with a halogenating agent such as thionyl chloride, phosphorus trichloride, phosphorus pentachloride, phosphorus oxychloride, oxalyl chloride, phosgene, thionyl bromide, phosphorus tribromide or phosphorus pentabromide, carbon tetrabromide-triphenylphosphine and the like; or by reacting a compound of the general formula [XII] with methanesulfonyl chloride, trifluoromethanesulfonic anhydride, benzenesulfonyl chloride or p-tolenesulfonyl chloride, in the presence of a base by the method known per se.

Production Method 4

Production method 4 is for producing a benzimidazolone derivative of the general formula [I], through a condensation reaction of a compound of the general formula [II] with a compound of the general formula [XII], in the presence of dialkylazodicarboxylate and an organic phosphorus compound such as triarylphosphine or trialkylphosphine.

This method is particularly advantageous where $R^{3a}$ is lower alkyl or lower alkenyl, or $R^{3a}$ and $R^4$ together form a 3- to 6-membered carbocyclic ring. The reaction scheme is as follows.

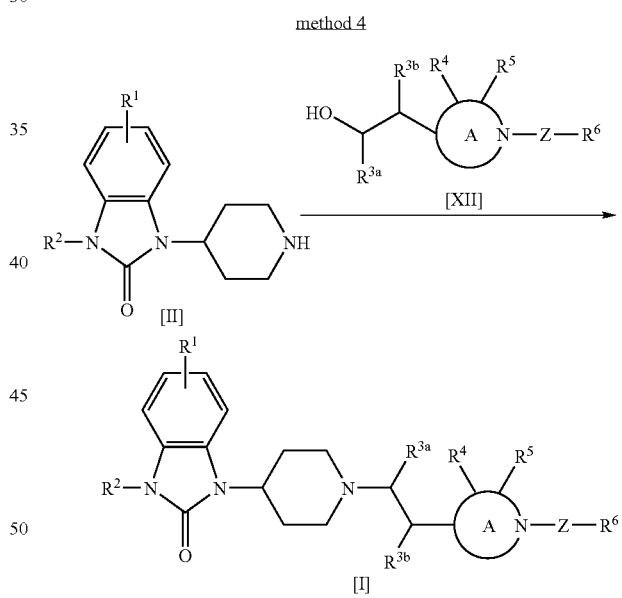

in the above formulae, $R^1$, $R^2$, $R^{3a}$, $R^{3b}$, $R^4$, $R^5$, $R^6$, Z and A ring are same as earlier defined.

Examples of dialkylazodicarboxylate useful in the production method 4 include diethylazodicarboxylate, diisopropylazodicarboxyate, diisobutylazodicarboxylate, di-tert-butylazodicarboxylate and the like.

As examples of triarylphosphine, triphenyphophine, tri(o-tolyl)phosphine and the like can be named, and as trialkylphosphine, triethylphosphine, tributylphosphine, trioctylphosphine and the like can be named. In particular, combinations of diisopropylazodicarboxylate or diisobutylazodicarboxylate with tributylphosphine are recommended.

As the use rate of the compound of the general formula [II] and that of the general formula [XII], for example, 1–3 moles, preferably 1.0–1.5 moles, of the compound of the general formula [XII] is used per mole of the compound of the general formula [II].

As the use rates of dialkylazodicarboxylate and the organophosphorus compound such as triarylphosphine or trialkylphosphine, 1–3 moles, preferably 1–1.5 moles of dialkylazodicarboxylate and 1–3 moles, preferably 1.0–1.5 moles of the organophosphorus compound can be used per mole of the compound of the general formula [II].

As the reaction solvent, halogenated hydrocarbons such as methylene chloride, chloroform and 1,2-dichloroethane; aliphatic hydrocarbons such as heptane and hexane; ethers such as diethyl ether, tetrahydrofuran and 1,4-dioxane; esters such as ethyl acetate and methyl acetate; and aprotic polar solvents such as N,N-dimethylformamide and dimethyl sulfoxide can be named for example.

The reaction temperatures can range, for example, 0–150° C., preferably 0–80° C., and the reaction normally terminates in 2–24 hours.

A compound of the general formula [XII] can be obtained, as shown in the production method 1, by reacting a compound 1 with that of a general formula [VII], in the manner following the production method 2d).

Furthermore, the compound of the general formula [XII] in the production method 4 can be replaced by that of a general formula [XII']

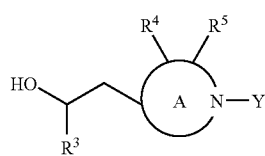

[XII']

which is reacted in the similar manner to produce a corresponding compound of the general formula [XI. This compound can be reacted in the manner following the production method 3, to be converted to the corresponding compound of the general formula [I].

Production Method 5

Production method 5 comprises reacting a compound of the general formula [XIII] with a compound selected from the group consisting of carbonyldiimidazole, triphosgene [i.e., bis(trichloromethyd)carbonate], diphosgene [i.e., trichloromethyl chloroformate], methyl chloroformate, ethyl chloroformate, phenyl chloroformate, methyl chlorothioformate, dimethyl carbonate, diethyl carbonate, S,S'-dimethyl dithiocarbonate, S,S'-diethyl dithiocarbonate and urea, preferably in the presence of a base, to form benzimidazolone skeleton. Its scheme is shown by the following formula.

method 5

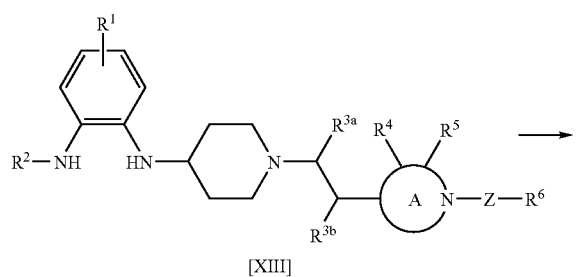

[XIII]

-continued

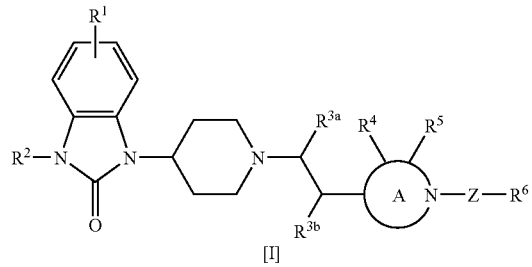

[I]

in the formulae, $R^1$, $R^2$, $R^{3a}$, $R^{3b}$, $R^4$, $R^5$, $R^6$, Z and A ring have the earlier defined significations.

In this reaction, normally 0.95–10 moles, preferably 1.1–2 moles of a compound such as carbonyldiimidazole, triphosgene, diphosgene, methyl chloroformate, ethyl chloroformate, phenyl chloroformate, methyl chlorothioformate, dimethyl carbonate, diethyl carbonate, S,S'-dimethyl dithiocarbonate, S,S'-diethyl dithiocarbonate or urea is used per mole of a compound of the general formula [XIII].

This reaction can be performed in the presence of a base where necessary, and as the base an organic base such as triethylamine, diisopropylethylamine or 4-(dimethylamino) pyridine; an inorganic base such as sodium hydride, sodium carbonate, potassium carbonate or sodium hydrogencarbonate can be named for example. The use rate of the base is 0.9–5 moles, preferably 1.0–4.0 moles, per mole of the compound of the general formula [XIII].

The reaction is normally carried out in an inert solvent, examples of which include ethers such as ethyl ether, tetrahydrofuran, dioxane and the like; halogenated hydrocarbons such as methylene chloride, chloroform, 1,2-dichloroethane and the like; aromatic hydrocarbons such as benzene, toluene, chlorobenzene, xylene and the like; aprotic polar solvents such as N,N-dimethylformamide, hexamethylphosphoric triamide and the like; or mixed solvents of the foregoing.

Reaction temperature may be, for example, in the range of 0–150° C., preferably 10–100° C., and the reaction normally terminates in 5 minutes–48 hours, preferably in 10 minutes–24 hours.

After termination of the reaction, excessive reagent is removed by the means known per se, to provide a crude product of benzimidazolone derivative of the general formula [I].

Where amino, hydroxyl or like groups which do not participate in the reaction are present, the reaction is preferably carried out after they are suitably protected by amino-protective group or hydroxyl-protective group, such protective groups being removed after the reaction.

The compounds represented by the general formula [XIII] can be prepared following the methods which are described, for example, in International Publication WO97/16192 or Patent Application No. Hei 11 (1999)-291232.

Of the production methods 1–5, Production methods 1–3 or 5 are preferred, inter alia, Production method 2.

In the Production methods 1–5, the reaction liquids after the reactions in occasions contain excessive reagent, sideproducts or the like. By isolating and purifying the reaction liquids by the means known per se after optional condensation step, the benzimidazolone derivatives of the general formula [I] can be recovered.

The isolation and purification can be accomplished by carrying out such separation means as column chromatography using an adsorptive resin such as silica gel, alumina or the like, or ion-exchange resin; thin-layer chromatography, high performance liquid chromatography, solvent-extraction or recrystallization/represipitation either singly or in combination.

Furthermore, where a compound of the general formula [I] is a mixture of stereoisomers, optical isomer(s) therein may be isolated by the means known per se.

The benzimidazolone derivatives represented by the general formula [I] can be converted to pharmaceutically acceptable salts thereof by the means known per se. Conversely, conversion from salts to free compounds can also be performed by the means known per se.

As preferred salts of the benzimidazolone derivatives represented by the general formula [I], for example, hydrochloride, hydrobromide, hydroiodide, sulfate, nitrate, phosphate, perchlorate, maleate, fumarate, tartarate, citrate, ascorbate, benzoate, methanesulfonate, isethionate, benzenesulfonate, 4-toluenesulfonate and the like can be named, among which hydrochloride, hydrobromide, phosphate, tartarate, citrate and methanesulfonate are preferred.

Pharmacological Activities of the Benzimidazolone Derivatives Represented by the General Formula [I]

Utility of the compounds of the present invention has been verified by the following test on inhibition of binding to muscarinic receptors.

Test on Inhibition of Binding to Muscarinic Receptors

The test was performed according to a modification of the method of Hargreaves, et al. (*Br. J. Pharmacol.* 107: 494–501, 1992). Namely, muscarinic acetylcholine receptors of human $m_1$, $m_2$, $m_3$, $m_4$ and $m_5$ expressed in CHO cells (Receptor Biology, Inc.) were incubated with 0.2 nM [$^3$H]-N-methylscopolamine (82Ci/mmol, New England Nuclear, Inc.) and a test compound, either in 0.5 ml of 50 mM Tris-HCl, 10 mM $MgCl_2$, 1 mM EDTA solution (pH 7.4) (human $m_1$, m3 and $m_5$ samples) or in 0.5 ml of 50 mM tris-HCl, 10 mM $MgCl_2$, 1 mM EDTA, 5000 nM GTPγS solution (pH 7.4) (human $m_2$ and $m_4$ samples) for 120 minutes at room temperature (about 20–25° C.), followed by suction filtration over a glass filter (UniFilter plate-GF/C; Packard). Then the filter was washed four times with 1 ml of ice-cooled Tris-HCl buffer and dried at 50° C. for an hour. After adding a scintillator (Microscinti 0; Packard), the radioactivity of [$^3$H]-N-methylscopolamine binding to the filter was counted with a microplate scintillation counter (TopCount; Packard). Non-specific receptor binding of [$^3$H]-N-methylscopolamine was measured by adding 1 μM N-methylscopolamine. According to the method of Cheng and Prusoff (*Biochem. Pharmacol.* 22: 3099–3108, 1973), the binding affinity of each sample compound of the present invention for muscarinic receptors is expressed by inhibition constant (Ki) which is calculated from the concentration ($IC_{50}$) of the sample compound which achieves 50% inhibition of binding of [$^3$H]-N-methylscopolamine, the labeled ligand. Smaller inhibition constant (Ki) represents stronger tendency to bind to muscarinic receptors, i.e., a higher binding inhibitory effect.

TABLE 1

Inhibitory Action against Binding to Muscarinic Receptors

| | Ki (nM) | | | | | Selectivity (times) | | | |
|---|---|---|---|---|---|---|---|---|---|
| Compound | $m_1$ | $m_2$ | $m_3$ | $m_4$ | $m_5$ | $m_1/m_4$ | $m_2/m_4$ | $m_3/m_4$ | $m_5/m_4$ |
| Example 4 | 28 | 73 | 7400 | 4.5 | 260 | 6.1 | 16 | 1600 | 57 |
| Example 9 | 25 | 31 | 1700 | 1.7 | 450 | 15 | 19 | 1000 | 270 |
| Example 12 | 22 | 24 | 4500 | 2.3 | 220 | 9.7 | 11 | 2000 | 99 |

As is clear from the results indicated in above Table 1, those compounds of the present invention exhibited selective inhibitory action against binding to muscarinic $m_1$ and $m_4$ receptors rather than to $m_2$, $m_3$ and $m_5$ receptors. In particular, they exhibited strong activity against binding to $m_4$ receptor.

Pharmaceutical Compositions Containing Benzimidazolone Derivatives of the General Formula [I] or Salts thereof Compounds represented by the structural formula [I] of the present invention are useful as drug for treating or preventing Parkinson's disease, drug-induced parkinsonism, dystonia, akinesia, pancreatitis, bilestone/cholecystitis, biliary dyskinesia, achalasia, pain, itch, cholinergic urticaria, irritable bowel syndrome, vomiting, nausea, dizziness, Meniere's disease, motion sickness such as space sickness, sea sickness and car sickness, and urinary disturbance. Pharmaceutical compositions can be formulated using these compounds as the active ingredient and further adding pharmaceutically acceptable adjuvants.

As the dosage form of these pharmaceutical compositions, various forms can be selected, for example, solid preparations such as tablets, capsules, powders, granules and triturates; and liquid preparations such as solutions suspension syrups and injections. Depending on their forms, the preparations can be used a peroral or parenteral drugs. These preparations may be formulated by known means such as mixing, kneading, granulating, compression molding, punching, coating, sterilizing, emulsifying and the like, according to their dosage forms.

While those solid preparations can be prepared from the compounds of the present invention only, into tablets, capsules, granules or powders, they may be prepared using pharmaceutically acceptable, suitable adjuvants. Examples of such adjuvants include saccharides such as lactose and glucose; starch such as corn starch, wheat and rice; fatty acid such as steraric acid; inorganic salts such as magnesium aluminate, magnesium metasilicic aluminate, (heavy) magnesium oxide, (precipitated) calcium carbonate, anhydrous calcium phosphate, light silicic anhydride and titanium oxide; synthetic polymers such as polyvinyl alcohol, polyvinylpyrrolidone and polyalkylene glycol; fatty acid salts such as calcium stearate and magnesium stearate; alcohols such as cetyl alcohol, stearyl alcohol and benzyl alcohol; synthetic cellulose derivatives such as methyl cellulose, carboxymethyl cellulose, ethyl cellulose, hydroxypropyl cellulose and hydroxypropylmethyl cellulose; crystalline cellulose; carboxylic acid such as citric acid and sodium citrate; glycols such as propylene glycol and polyalkylene glycol; surfactants such as sorbitan fatty acid ester, polysorbate and sucrose fatty acid ester; and those conventionally used adjuvants such as water, sorbitol, polyoxyethylene, gelatine, talc, microcrystalline wax, white petrolatum, vegetable oil, hardened custor oil, gum Arabic, cyclodextrin, hydroxypropyl cyclodextrin and the like.

These solid preparations such as tablets, capsules, granules and powders generally contain 0.1–100% by weight, preferably 0.1–20% by weight, of the active ingredient.

In liquid preparations, pharmaceutically acceptable, suitable adjuvants that are customarily used for liquid preparations, such as water, alcohols, vegetable oils, e.g., soy bean oil, peanut oil and sesame oil, and the like can be used, to prepare such dosage forms as suspension, syrup or injection. Where necessary, non-ionic surfactant may also be used.

In particular, as suitable solvent for intramuscular injection, intravenous injection or hypodermic injection used for parenteral administration, distilled water for injection, aqueous lidocaine hydrochloride solution (for intramuscular injection), physiological saline, aqueous glucose solution, ethanol, liquid for intravenous injection (e.g., aqueous solutions of citric acid, sodium citrate or the like) or electrolytic solution (for intravenous drip or intravenous injection), and mixed solutions of the foregoing can be named. These injections can take such forms as, besides solution form, powder form without or with suitable adjuvant(s), to be dissolved prior to actual use. These injections normally contain 0.1–10% by weight, preferably 1–5% by weight, of the active ingredient. Also the liquid preparations for oral administration such as suspension and syrup contain 0.5–10% by weight of the active ingredient.

Where the compounds of the present invention are used for treatment or prophylaxis of, for example, Parkinson's disease, drug-induced parkinsonism, dystonia, akinesia, pancreatitis, bilestone/cholecystitis, biliary dyskinesia, achalasia, pain, itch, cholinergic urticaria, irritable bowel syndrome, vomiting, nausea, dizziness, Meniere's disease, motion sickness such as space sickness, sea sickness and car sickness and urinary disturbance, their dosage level and dosage schedule vary according to the sex, age, body weight, severity of symptoms of individual patient, type and range of the desired therapeutic effect. Generally for oral administration, they are preferably administered in a daily dose of 0.01 to 10 mg/kg for adults and this daily dose may be given at a time or in several divided doses. For parenteral administration, they are preferably administered in a daily dose of 0.003 to 3 mg/kg, at a time or in several divided doses. Depending on patient' s symptoms, these preparations can also be administered for prophylactic treatment.

Optimum Embodiments for Working the Invention

Hereinafter the present invention is explained more specifically, referring to working examples which however do not incur any limitations on the present invention. In the examples, $^1$H-NMR was measured, using tetramethylsilane as the standard substance.

PRODUCTION EXAMPLE 1

1-[1-[2-(Piperidin-4-yl)ethyl]pineridin-4-yl]-1,3-dihydro-2H-benzimidazol-2-one dihydrochloride To a solution of 240 mg of piperidine-4-ethanol in 3 ml of chloroform, 446 mg of DIBOC (di-tert-butyldicarbonate) was added and stirred for 3 hours at room temperature. The reaction liquid was diluted with chloroform, and the chloroform layer was washed successively with saturated aqueous sodium hydrogencarbonate solution and saturated brine, dried over anhydrous sodium sulfate and concentrated. The residue so obtained was purified on silica gel chromatography (chloroform/methanol=30/1) to provide 456 mg of 1-(tert-butoxycarbonyl)piperidine-4-ethanol, which was then dissolved in 2 ml of chloroform. To the solution 205 μl of methanesulfonyl chloride and 1 ml of triethylamine, followed by 10 hours' stirring at room temperature. Saturated sodium hydrogencarbonate was added to the reaction liquid, which was then extracted with chloroform three times. This solution was dried over anhydrous sodium sulfate and concentrated. To the residue, 20 ml of dimetylformamide, 499 mg of 1-(piperldin-4-yl)-1,3-dihydro-2H-benzimidazol-2-one, 477 mg of potassium carbonate and 38 mg of potassium iodide were added, followed by 10 hours' stirring at 80° C. After cooling the reaction liquid, chloroform and saturated aqueous sodium hydrogencarbonate solution were added thereto, and the resulting mixture was shaken to separate the organic layer. The organic layer was dried over anhydrous sodium sulfate and removed of the solvent. The resulting residue was purified on silica gel chromatography, to provide 275 mg of 1-[1-[2-[1-tert-butoxycarbonylpiperidin-4-yl]ethyl]piperidin-4-yl-]-1,3-dihydro-2H-benzimidazol-2-one. To this compound, 10 ml of 10% hydrogen chloride/methanol was added, followed by 6 hours' stirring at room temperature. The reaction liquid was concentrated, to which methanol was added and distilled under reduced pressure to remove excess of hydrogen chloride and to provide the title compound.

EXAMPLE 1

1-[1-[2-(1-Benzoylpiperidin-4-yl)ethyl]piperidin-4-yl]-1 3-dihydro-2H-benzimidazol-2-one To 20 mg of 1-[1-[2-(piperidin-4-yl)ethyl]piperidin-4-yl]-1,3-dihydro-2H-benzimidazol-2-one dihydrochloride which was synthesized in Production Example 1, 10 mg of benzoyl chloride, 27 mg of diisopropylethylamine and 2 ml of chloroform were added, and sonicated for 30 minutes. Then 20 mg of piperidine was added to the system followed by 10 minutes' standing. The resulting reaction mixture was concentrated, and the residue was purified on silica gel chromatography (chloroform/methanol=15/1) to provide 14 mg of the title compound as a colorless oil.
$^1$H-NMR(CDCl$_3$)δ:1.04–2.08(10H,m),2.08–2.32(2H,m), 2.32–2.68(4H,m),2.68–3.22(3H,m),3.60–3.88(1H,m), 4.30–4.80(2H,m),7.00–7.60(8H,m),7.80–7.87(1H,m),9.31 (1H,brs) ESI-MS(M+H)$^+$:433

EXAMPLE 2

1-[1-[2-[1-(4-Chlorophenylsulfonyl)piperidin-4-yl]ethyl]piperidin-4-yl]-1,3-dihydro-2H-benzimidazol-2-one Conducting the operations according to Example 1 except that the benzoyl choride was replaced with 4-chlorobenzenesulfonyl chloride, the title compound was obtained as a colorless, amorphous substance.
$^1$H-NMR(CDCl$_3$)δ:0.75–2.60(17H,m),2.90–3.15(2H,m), 3.65–3.90(2H,m),4.20–4.45(1H,m),6.95–7.15(3H,m), 7.15–7.35(1H,m),7.52(2H,d,J=8.4 Hz),7.71(2H,d,J=8.4 Hz), 8.87(1H,s) ESI-MS(M+H)$^+$:503/505

EXAMPLE 3

1-[1-[2-[1-[4-(trifluoromethoxy)phenylsulfonyl]piperidin-4-yl]ethyl]-piperidin-4-yl]-1,3-dihydro-2H-benzimidazol-2-one Conducting the operations according to Example 1 except that the benzoyl choride was replaced with 4-(trifluoromethoxy)-benzenesulfonyl chloride, the title compound was obtained as a colorless, amorphous substance.
$^1$H-NMR(CDCl$_3$)δ:1.10–2.60(17H,m),2.95–3.15(2H,m), 3.70–3.90(2H,m),4.25–4.45(1H,m),6.90–7.15(3H,m), 7.15–7.30(1H,m),7.36(2H,d,J=9.0 Hz),7.83(2H,d,J=9.0 Hz), 9.47(1H,s) ESI-MS(M+H)$^+$:553

EXAMPLE 4

1-[1-[2-[1-(Pyrazinylcarbonyl)piperidin-4-yl]ethyl]piperidin-4-yl]-1,3-dihydro-2H-benzimidazol-2-one To 73 mg of 1-[1-[2-(piperidin-4-yl)ethyl]piperidin-4-yl]-1,3-dihydro-2H-benzimidazol-2-one dihydrochloride which was synthesized in Production Example 1, 28 mg of pyrazinecarboxylic acid, 101 µl of triethylamine and 14 mg of 1-hydroxybenzotriazole were added, and the mixture was suspended in 5 ml of chloroform. Then 52 mg of 1-ethyl-3-[3-(dimethylamino)propyl]carbodiimide hydrochloride was added to the suspension, and the resulting reaction mixture was stirred for 3 hours at room temperature. To the reaction liquid, ethyl acetate and saturated aqueous sodium hydrogencarbonate solution were added and mixed by shaking, to recover the separated organic layer. The organic layer was successively washed with saturated aqueous sodium hydrogencarbonate solution and saturated brine, dried over anhydrous sodium sulfate, and the solvent was distilled off. The resulting residue was purified on silica gel chromatography (chloroform/methanol=10/1) to provide 40 mg of the title compound as a colorless oil.

$^1$H-NMR(CDCl$_3$)δ:1.20–1.98(10H,m),2.05–2.20(2H,m), 2.30–2.60(3H,m),2.75–2.95(1H,m),3.00–3.20(3H,m), 3.80–3.98(1H,m),4.25–4.50(1H,m),4.65–4.85(1H,m), 6.95–7.17(3H,m),7.20–7.40(1H,m),8.56(1H,dd,J=1.5 Hz,2.7 Hz), 8.63(1H,d,J=2.7 Hz),8.90(1H,d,J=1.5 Hz),9.57 (1H,brs) ESI-MS(M+H)$^+$:435

PRODUCTION EXAMPLE 2

1-[1-[2-(1,2,5.6-Tetrahydro-4-pyridyl)ethyl]piperidin-4-yl]-1,3-dihydro-2H-benzimidazol-2-one dihydrochloride A solution of 300 mg of (1-tert-butoxycarbonylpiperidin-4-ylidene)acetic acid ethyl ester (which had been prepared by Horner-Wittig reaction of commercially available 1-tert-butoxycarbonyl-4-piperidone and triethyl phosphonoacetate by the method known per se) in 30 ml of tetrahydrofuran was cooled to −78° C., to which 1.3 ml of a tetrahydrofuran solution (1.5 M) of lithium diisopropylamide was added and stirred for 15 minutes. Thereafter 150 µl of acetic acid was added, and the system was warmed up to room temperature, over an hour. The reaction liquid, to which saturated aqueous sodium hydrogencarbonate solution was added, was extracted with chloroform. The chloroform layer was dried over sodium sulfate and the solvent was distilled off therefrom to provide 329 mg of (1-tert-butoxycarbonyl-1,2,5,6-tetrahydropyridin-4-yl)acetic acid ethyl ester. This ester was dissolved in 10 ml of tetrahydrofuran, cooled to 0° C., and to which 80 mg of lithium aluminium hydride was added. The reaction liquid was stirred for 15 minutes and to which an excessive amount of sodium sulfate decahydrate was added, followed by 2 hours' stirring at room temperature. The insoluble matter was filtered off, and the filtrate was concentrated to provide 228 mg of 2-(1-tert-butoxycarbonyl-1,2,5,6-tetrahydropyridin-4-yl)ethanol.

Of the above product, 25 mg was dissolved in 3 ml of ethyl acetate, to which 16 mg of methanesulfonyl chloride and 35 mg of triethylamine were added, followed by 30 minutes' stirring at room temperature. The reaction liquid, to which saturated aqueous sodium hydrogencarbonate solution was then added, was extracted with ethyl acetate. The ethyl acetate layer was washed with saturated brine, dried over anhydrous magnesium sulfate and removed of the solvent by distillation. The resulting residue was dissolved in 3 ml of acetonitrile, and to the acetonitrile solution 30 mg of 1-(piperidin-4-yl)-1,3-dihydro-2H-benzimidazol-2-one, 35 mg of potassium carbonate and 5 mg of potassium iodide were added, followed by heating to 70° C. and 7 hours' stirring. The reaction liquid was cooled and water was added thereto, followed by extraction with ethyl acetate. The ethyl acetate layer was successively washed with water and saturated brine, dried over anhydrous sodium sulfate and the solvent was distilled off. The resulting residue was purified on silica gel chromatography (chloroform/methanol=10/1) to provide 35.8 mg of the title compound as a colorless oil.

EXAMPLE 5

1-[1-[2-[1,2,5,6-Tetrahydro-1-(pyrazinylcarbonyl)-4-pyridyl]ethyl]-piperidin-4-yl]-1 3-dihydro-2H-benzimidazol-2-one Conducting the operations similarly to those in Example 4 except that 1-[1-[2-(1,2,5,6-tetrahydro-4-pyridyl)ethyl]piperidin-4-yl]-1,3-dihydro-2H-benzimidazol-2-one dihydrochloride which was synthesized by the method of Production Example 2 was used in place of 1-[1-[2-(piperidin-4-yl) ethyl]piperidin-4-yl]-1,3-dihydro-2H-benzimidazol-2-one dihydrochloride, the title compound was obtained.

$^1$H-NMR(CDCl$_3$)δ:0.80–2.70(12H,m),3.02–3.26(2H,m), 3,59–4.50(5H,m),5.32–5.60(1H,m),7.00–7.33(4H,m), 8.13–8.22(1H,m),8.50–8.60(1H,m),8.60–8.69(1H,m), 8.92–8.99(1H,m) ESI-MS(M+H)$^+$:433

PROUCTION EXAMPLE 3

1-[1-[2-(3-Methylene-4-piperidyl)ethyl]piperidin-4-yl]-1,3-dihydro-2H-benzimidazol-2-one dihydrochloride In 30 ml of xylene, 1.10 g of 1-tert-butoxycarbonyl-1,2,5,6-tetrahydropyridine-3-methanol (which had been prepared by the method described in *Tetrahedron*, Vol. 54, No. 25, p. 7045, 1998), 914 mg of ethyl orthoformate and 130 mg of 2,4-dinitrophenol were dissolved, and the formed solution was heated to 140° C. and stirred for 7 hours while removing the ethanol as formed. The reaction liquid was cooled, then ethyl acetate was added thereto and the organic layer was successively washed with 1N hydrochloric acid, saturated aqueous sodium hydrogencarbonate solution and saturated brine, dried over anhydrous sodium sulfate and removed of the solvent by distillation. The resulting residue was purified on silica gel column chromatography (hexane/ethyl acetate=10/1) to provide 692 mg of 1-tert-butoxycarbonyl-3-methylenepiperidine-4-acetic acid ethyl ester. The product was dissolved in 20 ml of tetrahydrofuran, cooled to 0° C., 111 mg of lithium aluminium hydride was added thereto, and stirred for an hour. Then an excessive amount of sodium sulfate decahydrate was added to the reaction liquid and stirred for 15 minutes. The resulting mixture was filtered, and the filtrate was concentrated to provide 558 mg of crude 1-tert-butoxycarbonyl-3-methylenepiperidine-4-ethanol.

Of the above product, 100 mg was dissolved in 3 ml of chloroform, and to the solution 35 µl of methanesulfonyl chloride and 173 µl of triethylamine were added, followed by 2 hours' stirring at room temperature. The reaction liquid was partitioned between chloroform and saturated aqueous sodium hydrogencarbonate solution, and the organic layer was washed with saturated brine, dried over anhydrous magnesium sulfate, and the solvent was distilled off. The residue was dissolved in 2 ml of dimethylformamide and to the solution 99 mg of 1,3-dihydro-1-(4-piperidyl)-2H-benzimidazol-2-one and 86 mg of potassium carbonate were added, followed by heating to 80° C. and 5 hours' stirring. The reaction liquid was cooled and partitioned between ethyl acetate and saturated aqueous sodium hydrogencarbonate solution. The organic layer was washed with saturated brine, dried over anhydrous sodium sulfate and the solvent was distilled off. The resulting residue was purified on silica gel chromatography (chloroform/methanol=10/1) to provide 32 mg of 1-[1-[2-(1-tert-butoxycarbonyl-3-methylene-4-piperidyl)ethyl]-piperidin-4-yl]-1,3-dihydro-2H-benzimidazol-2-one, of which 30 mg was dissolved in 2 ml of 10% hydrogen chloride/methanol and stirred for 8 hours at room temperature. The reaction liquid was concentrated, to which further methanol was added and from which the excess of hydrogen chloride was distilled off under reduced pressure to provide 29 mg of the title compound as a colorless solid.

EXAMPLE 6

1-[1-[2-[1-(Pyrazinylcarbonyl)-3-methylene-4-piperidyl]ethyl]piperidin-4-yl]-1,3-dihydro-2H-benzimidazol-2-one Conducting the operations similarly to those in Example 4 except that [1-[2-(piperidin-4-yl)ethyl]piperidin-4-yl]-1,3-dihydro-2H-benzimidazol-2-one dihydrochloride was replaced with 1-[1-[2-(3-methylene-4-piperidyl)ethyl]-piperidin-4-yl]-1,3-dihydro-2H-benzimidazol-2-one dihydrochloride which was synthesized in Production Example 3, the title compound was obtained.
$^1$H-NMR(CDCl$_3$)δ:1.20–2.65(13H,m),3.00–3.20(2H,m), 3.40–3.70(1H,m),3.70–4.65(3H,m),4.30–4.45(1H,m), 4.70–5.18(2H,m),6.99–7.15(3H,m),7.20–7.35(1H,m), 8.50–8.70(2H,m),8.92(1H,s),9.10–9.35(1H,brs) ESI-MS (M+H)$^+$:447

PRODUCTION EXAMPLE 4

(S*)-1-[1-[2-(perhydroazepin-4-yl)ethyl]piperidin-4-yl]-1,3-dihydro-2H-benzimidazol-2-one dihydrochloride and (R*)-1-[1-[2-(perhydroazepin-4-yl)ethyl]piperidin-4-yl]-1,3-dihydro-2H-benzimidazol-2-one dihydrochloride (S* and R* are provisional configurations allotted to distinguish the stereoisomers, standing for the configuration at 4-position of perhydroazepine)

Into a suspension of 50 mg of sodium hydride in 5 ml of tetrahydrofuran, which was cooled to 0° C., 210 μl of ethyl diethylphosphonoacetate was added. After its temperature was restored to room temperature, the system was stirred for an hour. Cooling the reaction liquid to 0° C. once again, a tetrahydrofuran (5 ml) solution containing 205 mg of 1-tert-butoxy-carbonylperhydroazepin-4-one (this compound is described in International Publication WO 00/00203) was added, followed by 40 minutes' stirring at room temperature. Saturated aqueous ammonium chloride solution was added to the reaction liquid, the tetrahydrofuran was distilled off, further water was added, and the system was extracted with ethyl acetate. The extract was washed with saturated brine, dried over anhydrous sodium sulfate, and from which the solvent was distilled off. The residue was purified on silica gel chromatography (eluted first with hexane/ethyl acetate=10/1, and then=7/1) to provide 173 mg of (1-tert-butoxycarbonylperhydroazepin-4-ylidene)acetic acid ethyl ester as a colorless oil.

Thus obtained compound was dissolved in a liquid mixture of 5 ml of methanol and 1 ml of tetrahydrofuran. To the solution 39 mg of 10% palladium-on-carbon was added, and stirred for 2 hours at room temperature and in hydrogen exerting 1 atmospheric pressure. The reaction liquid was filtered, the filtrate was concentrated, and the resulting residue was dissolved in 6 ml of diethyl ether. The ether solution was cooled to 0° C., and to which 23 mg of lithium aluminium hydride was added, followed by 3 hours' stirring in nitrogen atmosphere. Then an excessive amount of sodium sulfate decahydrate was added to the ether solution, its temperature was restored to room temperature, and the solution was stirred for 90 minutes. The insoluble matter was distilled off and the filtrate was concentrated to provide 150 mg of 2-(1-tert-butoxycarbonylperhydro-azepin-4-yl) ethanol as a colorless oil. The oil was dissolved in 10 ml of ethyl acetate, and to the solution 170 μl of triethylamine and 52 μl of methanesulfonyl chloride were added, followed by 15 minutes' stirring at room temperature. Saturated aqueous sodium hydrogencarbonate solution was added to the reaction liquid and extracted with ethyl acetate. The extract was washed with saturated brine, dried over anhydrous sodium sulfate and removed of the solvent by distillation.

Thus obtained residue was dissolved in 6 ml of dimethylformamide, to which 132 mg of 1-(piperidin-4-yl)-1,3-dihydro-2H-benzimidazol-2-one, 168 mg of potassium carbonate and 10 mg of potassium iodide were added, followed by heating to 80° C. and 16 hours' stirring. The reaction liquid was restored to room temperature, diluted with ethyl acetate, and the ethyl acetate layer was washed three times with water and once with saturated brine, dried over magnesium sulfate, and the solvent was distilled off. The resulting residue was purified on silica gel chromatography (chloroform/methanol=10/1), to provide 153 mg of 1-[1-[2-(1-tert-butoxycarbonylperhydroazepin-4-yl)ethyl]piperidin-4-yl]-1,3-dihydro-2H-benzimidazol-2-one as a colorless oil. The oil was optically resolved using an optically active column [Chiral Cell OD (Daicel Chemicals) hexane/isopropyl alcohol/diethylamine=90/10/0.1], to provide 27 mg of earlier eluted isomer, 39 mg of later eluted isomer and 33 mg of their mixture. For distinguishing the two isomers, the earlier eluted isomer was expediently referred to as (R*)-1-[-[2-(1-tert-butoxycarbonylperhydroazepin-4-yl)ethyl]-piperidin-4-yl]-1,3-dihydro-2H-benzimidazol-2-one and the later eluted, as (S*)-1-[1-[2-(1-tert-butoxycarbonylperhydroazepin-4-yl)ethyl]piperidin-4-yl]-1,3-dihydro-2H-benzimidazol-2-one. The two isomers were led to the title compounds, respectively, by treating them with each 1 ml of 10% hydrogen chloride/methanol.

EXAMPLE 7

(S*)-1-[1-[2-[1-(Pyrazinylcarbonyl)perhydroazepin-4-yl] ethyl]piperidin-4-yl]-1,3-dihydro-2H-benzimidazol-2-one (S* is a provisional configuration allotted to distinguish the stereoisomer, showing the configuration at 4-position of the perhydroazepine.)

Conducting the operations same to those in Example 4 except that 1-[1-[2-(piperidin-4-yl)ethyl]piperidin-4-yl]-1, 3-dihydro-2H-benzimidazol-2-one dihydrochloride was replaced with (S*)-1-[1-[2-(perhydroazepin-4-yl)ethyl]piperidin-4-yl]-1,3-dihydro-2H-benzimidazol-2-one dihydrochloride, which was produced in Production Example 4, the title compound was obtained.
$^1$H-NMR(CDCl$_3$)δ:1.21–2.21(12H,m),2.35–2.55(4H,m), 3.05–3.15(2H,m),3.34–3.74(4H,m),3.80–4.00(1H,m), 4.26–4.50(1H,m),7.00–7.10(3H,m),7.29–7.38(1H,m), 8.50–8.95(3H,m),9.73(1H,brs) ESI-MS(M+H)$^+$:449

EXAMPLE 8

(R*)-1-[1-[2-[1-(pyrazinylcarbonyl)perhydroazepin-4-yl]
ethyl]piperidin-4-yl]-1,3-dihydro-2H-benzimidazol-2-one
(R* is a provisional configuration, showing the configuration at 4-position of the perhydroazepine)

Conducting the operations same to those in Example 7 except that (S*)-1-[1-[2-(perhydroazapin-4-yl)ethyl]piperidin-4-yl]-1,3-dihydro-2H-benzimidazol-2-one was replaced with (R*)-1-[1-[2-(perhydroazapin-4-yl)ethyl]-piperidin-4-yl]-1,3- dihydro-2H-benzimidazol-2-one dihydrochloride, which was produced in Production Example 4, the title compound was obtained.

$^1$H-NMR(CDCl$_3$)δ:1.21–2.21(12H,m),2.35–2.55(4H,m), 3.05–3.15(2H,m),3.34–3.74(4H,m),3.80–4.00(1H,m), 4.26–4.50(1H,m),7.00–7.10(3H,m),7.29–7.38(1H,m), 7.94 (1H,brs),8.50–8.95(3H,m) ESI-MS(M+H)$^+$:449

EXAMPLE 9

(S*)-1-[1-[2-[1-(3-pyridylcarbonyl)perhydroazepin-4-yl]
ethyl]piperidin-4-yl]-1,3-dihydro-2H-benzimidazol-2-one
(S* is a provisional configuration allotted to distinguish the stereoisomers, showing the configuration at 4-position of the perhydroazepine)

Conducting the operations same to those in Example 7 except that nicotinic acid was used in place of pyrazinecarboxylic acid, the title compound was obtained.

$^1$H-NMR(CDCl$_3$)δ:1.21–2.21(13H,m),2.30–2.60(4H,m), 3.00–3.15(2H,m),3.25–3.65(3H,m),3.81–4.02(1H,m), 4.25–4.45(1H,m),7.00–7.10(3H,m),7.20–7.39(2H,m), 7.74 (1H,d,J=7.7Hz),8.27(1H,brs),8.60–8.70(2H,m) ESI-MS(M+H)$^+$:448

EXAMPLE 10

(R*)-1-[1-[2-[1-(3-pyridylcarbonyl)perhydroazenin-4*-yl]
ethyl]piperidin-4-yl]-1,3-dihydro-2H-benzimidazol-2-one
(R* is a provisional configuration, indicating an isomer in respect of the 4* substituent.)

Operations same to those in Example 8 were performed except that nicotinic acid was used in place of pyrazinecarboxylic acid, to obtain the title compound.

$^1$H-NMR(CDCl$_3$)δ:1.21–2.21(13H,m),2.30–2.60(4H,m), 3.00–3.15(2H,m),3.25–3.65(3H,m),3.81–4.02(1H,m), 4.25–4.45(1H,m),7.01–7.11(3H,m),7.20–7.39(2H,m), 7.74 (1H,d,J=7.7Hz),8.60–8.70(2H,m),9.13(1H,brs) ESI-MS(M+H)$^+$:448

PRODUCTION EXAMPLE 5

1-[1-[2-(Piperidin-4-yl)propyl]piperidin-4-yl]-1,3-dihydro-2H-benzimidazol-2-one To a solution of 765 mg of 2-(1-tert-butoxycarbonylpiperidin-4-ylidene)propionic acid ethyl ester (prepared following the method of synthesis as described in International Publication WO 99/40070) in 4 ml of methanol, 100 mg of 10% palladium-on-carbon was added, and stirred for 4 hours at room temperature, in hydrogen atmosphere. Then the reaction liquid was filtered and the filtrate was concentrated to provide 743 mg of 2-(1-tert-butoxycarbonylpiperidin-4-yl)propionic acid ethyl ester as a slightly yellowish oil. Of said product, 306 mg was dissolved in 9 ml of tetrahydrofuran and cooled to 0° C. To said tetrahydrofuran solution 150 mg of lithium aluminium hydride was added portionwise. The reaction liquid was stirred at 0° C. for an hour, sodium sulfate decahydrate was added thereto and the temperature was restored to room temperature, followed by an overnight's stirring. The reaction liquid was filtered, and the filtrate was concentrated to provide 313 mg of 2-(1-tert-butoxycarbonylpiperidin-4-yl)propanol as a yellowish oil. Of said oil, 210 mg was dissolved in 2 ml of dichloromethane and the solution was added to another −78° C. solution of 188 µl of oxaryl chloride and 359 µl of dimethylsulfoxide in dichloromethane (4 ml) over a period of 5 minutes. After 30 minutes' stirring, a solution of 993 µl of triethylamine in 0.5 ml of dichloromethane was added to the reaction liquid and the temperature of the system was restored to room temperature, followed by 25 minutes' stirring. After addition of water, the reaction liquid was extracted with ethyl acetate and the ethyl acetate layer was washed twice with water, dried over anhydrous sodium sulfate and concentrated to provide 163 mg of a pale yellow oil.

To said compound 147 mg of 1-(piperidin-4-yl)-1,3-dihydro-2H-benzimidazol-2-one and 2.7 ml of a methanolic solution of sodium cyanoborohydride and zinc chloride (each 0.3 mole/liter) were added, followed by 20 hours' stirring at room temperature. To the resulting reaction liquid saturated aqueous sodium hydrogencarbonate solution and saturated brine were added, and extracted with ethyl acetate. The ethyl acetate layer was successively washed with saturated aqueous sodium hydrogencarbonate solution and saturated brine, dried over anhydrous sodium sulfate and the solvent was distilled off. The residue was purified on silica gel chromatography (ethyl acetate/hexane=1/1, 1/2) to provide 97 mg of 1-[1-[2-(1-tert-butoxycarbonyl-piperidin-4-yl)propyl]piperidin-4-yl]-1,3-dihydro-2H-benzimidazol-2-one as a colorless, amorphous substance.

Of the product, 65 mg was dissolved in 1 ml of 10% hydrogen chloride/methanol, and the formed methanol solution was stirred for 2 hours at room temperature. The reaction liquid was concentrated, to which 1N aqueous sodium hydroxide solution was added until pH reached 10, and the solution was extracted with chloroform three times. Chloroform layers were combined, dried over anhydrous sodium sulfate, and the solvent was distilled off to provide 50 mg of the title compound as a colorless, amorphous substance.

EXAMPLE 11

1-[1-[2-[1-(Pyrazinylcarbonyl)piperidin-4-yl]propyl])piperidin-4-yl]-1,3-dihydro-2H-benzimidazol-2-one To 6.4 mg of 1-[1-[2-(piperidin-4-yl)propyl]piperidin-4-yl]-1,3-dihydro-2H-benzimidazol-2-one which was synthesized by the method of Production Example 5, 3.6 mg of pyrazinecarboxylic acid, 5.5 mg of N-ethyl-N'-[3-(dimethylamino)propyl]carbodiimide, 4.4 mg of 1-hydroxybenzotriazole, 10 µl of triethylamine and 1 ml of chloroform were added, followed by 3 hours' stirring at room temperature. To the reaction liquid, 1N aqueous sodium hydroxide solution was added until the latter's pH reached 10, followed by extraction with chloroform. The chloroform solution was washed with saturated brine, dried over anhydrous sodium sulfate and concentrated. Thus obtained residue was purified on silica gel chromatography (chloroform/methanol=10/1) to provide 6.0 mg of the title compound as a colorless solid.

$^1$H-NMR(CDCl$_3$)δ:0.92(3H,d,J=4.8Hz), 1.23–1.88(8H,m), 2.00–2.20(3H,m),2.26–2.56(3H,m), 2.72–2.88(1H,m), 2.92–3.18(3H,m),3.90–4.00(1H,m), 4.28–4.40(1H,m), 4.78–4.88(1H,m), 7.00–7.16(3H,m), 7.20–7.31(1H,m), 8.52–8.59(1H,m),8.60–8.66(1H,m),8.91 (1H,s), 8.95–9.12(1H,m) ESI-MS(M+H)$^+$:449

EXAMPLE 12

1-[1-[2-[1-(3-Pyridylcarbonyl)piperidin-4-yl]propyl] piperidin-4-yl]-1,3-dihydro-2H-benzimidazol-2-one Operations same as in Example 11 were conducted except that nicotinic acid was used in place of pyrazinecarboxylic acid, to provide the title compound as a colorless solid.

$^1$H-NMR(CDCl$_3$)δ:0.93(3H,d,J=6.3 Hz), 1.20–1.95(8H, m), 2.02–2.20(3H,m),2.29–2.56(3H,m),2.70–2.92(1H,m), 2.95–3.16(3H,m),3.70–3.85(1H,m),4.28–4.40(1H,m), 4.70–4.88(1H,m),7.01–7.13(3H,m),7.20–7.30(1H,m), 7.33–7.41(1H,m),7.76–7.82(1H,m),8.62–8.70(2H,m), 8.93–9.06(1H,m) ESI-MS(M+H)$^+$:448

EXAMPLE 13

1-[1-[2-[1-(3-Chlorobenzoyl)piperidin-4-yl]propyl] piperidin-4-yl]-1,3-dihydro-2H-benzimidazol-2-one Operations same as in Example 11 were conducted except that 3-chlorobenzoic acid was used in place of pyrazinecarboxylic acid, to provide the title compound as a colorless, amorphous substance.

$^1$H-NMR(CDCl$_3$)δ:0.92(3H,d,J=6.6 Hz), 1.18–1.90(8H, m), 2.00–2.22(3H,m),2.28–2.55(3H,m),2.66–2.75(1H,m), 2.93–3.10(3H,m),3.69–3.72(1H,m),4.28–4.40(1H,m), 4.70–4.83(1H,m),7.00–7.15(3H,m),7.20–7.57(5H,m), 8.98–9.08(1H,m) ESI-MS(M+H)$^+$:481

PRODUCTION EXAMPLE 6

1-[1-[2-(Piperidin-4-yl)-1-methylethyl]piperidin-4-yl]-1,3-dihydro-2H-benzimidazol-2-one To a solution of 1.01 g of 1-tert-butoxycarbonylpiperidin-4-acetic acid ethyl ester in 4 ml of methanol, 2 ml of 4N aqueous sodium hydroxide solution was added and stirred for 3 hours. Then 1N hydrochloric acid was added to make the reaction liquid acidic, which reaction liquid was extracted with chloroform. The organic layer was dried over anhydrous sodium sulfate and the solvent was distilled off to provide 840 mg of crude 1-tert-butoxycarbonylpiperidine-4-acetic acid. To this crude product, 5 ml of chloroform, 318 mg of N,O-dimethylhydroxylamine hydrochloride, 500 mg of 1-hydroxybenzotriazole, 623 mg of 1-ethyl-3-[3-(dimethylamino)-propyl]carbodiimide hydrochloride and 1.13 ml of triethylamine were successively added, followed by an overnight' s stirring. Saturated aqueous sodium hydrogencarbonate solution was added, and the reaction liquid was extracted with chloroform. The chloroform layer was successively washed with water and saturated aqueous ammonium chloride solution, dried over anhydrous sodium sulfate, and the solvent was distilled off, to provide 796 mg of N-methyl-N-methoxy-(1-tert-butoxycarbonylpiperidine-4-acetamide). Of the product, 353 mg was dissolved in 5 ml of tetrahydrofuran, and 0.62 ml of 3M methyl magnesium bromide/ether solution was added thereto at −78° C., followed by 10 minutes' stirring and further by 40 minutes' stirring at 0° C. Additional 0.20 ml of 3M methyl magnesium bromide/ether solution was added and stirring was continued for another hour. To the reaction liquid saturated aqueous ammonium chloride solution was added, and extracted with ethyl acetate. The extract was successively washed with water and saturated brine, dried over anhydrous sodium sulfate and the solvent was distilled off, to provide 300 mg of crude 1-tert-butoxycarbonyl-4-(2-oxopropyl)-piperidine. To 142 mg of this product, 2.5 ml of 1,2-dichloroethane, 128 mg of 1-(piperidin-4-yl)-1,3-dihydro-2H-benzimidazol-2-one, 174 mg of sodium triacetoxyborohydride and 0.04 ml of acetic acid were added and stirred for an overnight. Then 0.04 ml of acetic acid, 5 ml of 1,2-dichloroethane and 174 mg of sodium triacetoxyborohydride were further added to the system, and the mixture was stirred for 5 days. The pH of the reaction liquid was adjusted to 8 by addition of aqueous sodium hydrogencarbonate solution and aqueous sodium hydroxide solution, ethyl acetate was added and the reaction liquid was separated. The organic layer was washed with saturated brine, dried over anhydrous sodium sulfate and the solvent was distilled off. The residue was purified on silica gel column chromatography (hexane/ethyl acetate=3:1, 1:2; chloroform/methanol=100:1, 40:1) to provide 31 mg of 1-[1-[2-(1-tert-butoxycarbonylpiperidin-4-yl)-1-methylethyl]piperidin-4-yl]-1,3-dihydro-2H-benzimidazol-2-one. Twenty-eight (28) mg of said product was dissolved in 2 ml of 10% hydrogen chloride/methanol, stirred for 4 hours at room temperature and the solvent was distilled off. The pH of the residue was adjusted to 10 by addition of 1N aqueous sodium hydroxide solution, and the residue was extracted with chloroform. The extract was dried over anhydrous sodium sulfate and the solvent was distilled off to provide 21 mg of the title compound as a colorless solid.

EXAMPLE 14

1-[1-[2-[1-(3-Pyridylcarbonyl)piperidin-4-yl]-1-methylethyl]-piperidin-4-yl]-1,3-dihydro-2H-benzimidazol-2-one To 9.7 mg of 1-[1-[2-(piperidin-4-yl)-1-methylethyl]-piperidin-4-yl]-1,3-dihydro-2H-benzimidazol-2-one which was synthesized by the method of Production Example 6, 1 ml of chloroform, 4.4 mg of nicotinic acid, 8 mg of 1-ethyl-3-[3-(dimethylamino)propyl]-carbodiimide hydrochloride, 6.4 mg of 1-hydroxybenzotriazole and 0.01 ml of triethylamine were added and stirred for an overnight. To the reaction liquid 1N aqueous sodium hydroxide solution and chloroform were added to separate the reaction liquid. The organic layer was dried over anhydrous sodium sulfate, the solvent was distilled off, and the residue was purified on silica gel chromatography (chloroform/methanol=11:1) to provide 10.1 mg of the title compound as a colorless solid.

$^1$H-NMR(CDCl$_3$)δ:0.98(3H,d,J=6.3Hz), 1.10–2.00(9H,m), 2.27–2.62(4H,m),2.70–2.98(4H,m), 3.00–3.18(1H,m), 3.65–3.83(1H,m),4.23–4.38(1H,m), 4.60–4.82(1H,m), 6.98–7.12(3H,m),7.18–7.30(1H,m), 7.32–7.45(1H,m), 7.70–7.80(1H,m),8.60–8.75(2H,m), 9.07–9.18(1H,m) ESI-MS(M+H)$^+$:448

PRODUCTION EXAMPLE 7

1-(1-[2-[1-(3-Pyridylcarbonyl)piperidin-4-ylidene] ethyl]piperidin-4-yl]-1,3-dihydro-2H-benzimidazol-2-one Ninety (90) mg of 2-(1-tert-butoxycarbonylpiperidin-4-ylidine)ethanol was dissolved in 4 ml of ethyl acetate, and to which 70 μl of triethylamine and 33 gl of methanesulfonyl chloride were added, followed by 15 minutes' stirring at room temperature. The reaction liquid was diluted with ethyl acetate, washed successively with water and saturated brine, dried over anhydrous sodium sulfate and the solvent was distilled off. The residue was dissolved in 3 ml of dimethylformamide, to which 90 mg of 1-(piperidin-4-yl)-1,3-dihydro-2H-benzimidazol-2-one and 150 mg of potassium carbonate were added, stirred for 3 hours at room temperature, heated to 80° C., and further stirred for 3 hours. The reaction liquid was cooled, water was added thereto and the liquid was extracted with ethyl acetate. The extract was dried over anhydrous sodium sulfate, and the solvent was distilled off. The residue was purified on silica gel chromatography (chloroform/methanol=10:1), to provide 15.3 mg of 1-[1-[2-[1-(tert-butoxycarbonyl)piperidin-4-ylidene]ethyl]piperidin-4-yl]-1,3-dihydro-2H-benzimidazol-2-one, which was dissolved in 2 ml of 10% hydrogen chloride/methanol and stirred for 5 hours at room temperature. The reaction liquid was concentrated, and to the residue 2 ml of dimethylformamide, 50 mg of 1-hydroxybenzotriazole, 20 µl of triethylamine and 15 mg of 1-ethyl-3-[3-(dimethylamino)-propyl]carbondiimide hydrochloride were added, followed by an overnight's stirring at room temperature. Water and chloroform were added to the reaction liquid to separate the latter. The organic layer was washed with saturated aqueous sodium hydrogencarbonate solution and saturated brine, dried over anhydrous sodium sulfate and the solvent was distilled off. Purifying the residue on silica gel chromatography (chloroform/methanol=10:1), 2.7 mg of the title compound was obtained as a colorless oil.

EXAMPLE 15

1-[1-[2-Hydroxy-2-[4-hydroxy-1-(3-pyridylcarbonyl)piperidin-4-yl]-ethyl]piperidin-4-yl]-1,3-dihydro-2H-benzimidazol-2-one To 1-[1-[2-[1-(3-pyridylcarbonyl)piperidin-4-ylidene]ethyl]-piperidin-4-yl]-1,3-dihydro-2H-benzimidazol-2-one which was obtained in Production Example 7, 0.1 ml of 2% aqueous osmium tetroxide solution, 10 mg of N-methylmorpholine-N-oxide, 2 ml of acetonitrile and 1 ml of water were added at 0° C. and stirred for 15 minutes. The temperature was restored to room temperature and the system was further stirred for a day. To the reaction liquid ethyl acetate and aqueous sodium sulfite solution were added to separate the liquid, and the organic layer was dried over anhydrous sodium sulfate, removed of the solvent by distillation and purified on silica gel chromatography (chloroform/methanol=10:1) to provide 1.8 mg of the title compound as a colorless oil.
$^1$H-NMR(CDCl$_3$)δ:0.81–2.80(12H,m),3.00–3.77(6H,m), 4.20–4.75(2H,m),7.00–7.57(5H,m),7.72–7.80(1H,m), 8.05–8.16(1H,m),8.62–8.70(2H,m) ESI-MS(M+H)$^+$:448

EXAMPLE 16

1-[1-[2-[1-(2-Chlorobenzoyl)piperidin-4-yl]ethyl]-piperidin-4-yl]-1,3-dihydro-2H-benzimidazol-2-one Example 4 was repeated except that 2-chlorobenzoic acid was used in place of pyrazinecarboxylic acid, to provide the title compound as a colorless oil.
[M+H]$^+$=467

EXAMPLE 17

1-[1-[2-[1-(3-Chlorobenzoyl)piperidin-4-yl]ethyl]-piperidin-4-yl]-1,3-dihydro-2H-bezimidazol-2-one Example 4 was repeated except that 3-chlorobenzoic acid was used in place of pyrazinecarboxylic acid, to provide the title compound as a colorless, amorphous substance.
$^1$H-NMR(CDCl$_3$)δ:1.10–2.00(9H,m),2.05–2.20(2H,m), 2.35–2.60(4H,m),2.70–3.15(4H,m),3.60–3.80(1H,m), 4.25–4.45(1H,m),4.60–4.75(1H,m),7.00–7.12(3H,m), 7.26–7.41(5H,m),9.36(1H,brs) [M+H]$^+$=467

EXAMPLE 18

1-[1-[2-[1-(3-Bromobenzoyl)piperidin-4-yl]ethyl]piperidin-4-yl]-1,3-dihydro-2H-benzimidazol-2-one Example 4 was repeated except that pyrazinecarboxylic acid was replaced with 3-bromobenzoic acid, to provide the title compound as a colorless, amorphous substance.
[M+H]$^+$=511, 513

EXAMPLE 19

1-[1-[2-[1-(3-Iodobenzoyl)piperidin-4-yl]ethyl]-piperidin-4-yl]-1,3-dihydro-2H-benzimidazol-2-one Example 4 was repeated except that pyrazinecarboxylic acid was replaced with 3-iodobenzoic acid, to provide the title compound as a pale yellow, amorphous substance.
[M+H]$^+$=559

EXAMPLE 20

1-[1-[2-[1-(3,5-Dichlorobenzoyl)piperidin-4-yl]ethyl]piperidin-4-yl]-1,3-dihydro-2H-benzimidazol-2-one Example 4 was repeated except that pyrazinecarboxylic acid was replaced with 3,5-dichlorobenzoic acid, to provide the title compound as a colorless, amorphous substance.
[M+H]$^+$=501, 503

EXAMPLE 21

1-[1-[2-[1-(3,4-Dichlorobenzoyl)piperidin-4-yl]ethyl]-piperidin-4-yl]-1,3-dihydro-2H-benzimidazol-2-one Example 4 was repeated except that pyrazinecarboxylic acid was replaced with 3,4-dichlorobenzoic acid, to provide the title compound as a colorless solid.
[M+H]$^+$=501, 503

EXAMPLE 22

1-[1-[2-[1-(3-Pyridylcarbonyl)piperidin-4-yl]ethyl]-piperidin-4-yl]-1,3-dihydro-2H-benzimidazol-2-one Example 4 was repeated except that pyrazinecarboxylic acid was replaced with nicotinic acid, to provide the title compound as a colorless solid.
$^1$H-NMR(CDCl$_3$)δ:1.10–2.00(9H,m),2.05–2.20(2H,m), 2.35–2.55(4H,m),2.70–3.15(4H,m),3.60–3.80(1H,m), 4.25–4.45(1H,m),4.60–4.78(1H,m),7.00–7.10(3H,m), 7.25–7.40(2H,m),7.68–7.80(1H,m),8.55–8.70(3H,m) [M+H]$^+$=434

EXAMPLE 23

1-[1-[2-[1-[(4,5-Dichloro-3-pyridyl)carbonyl]piperidin-4-yl]ethyl]-piperidin-4-yl]-1,3-dihydro-2H-benzimidazol-2-one Example 4 was repeated except that pyrazinecarboxylic acid was replaced with 4,5-dichloronicotinic acid, to provide the title compound as a colorless solid.
$^1$H-NMR(CDCl$_3$)δ:1.05–2.60(15H,m),2.70–2.95(1H,m), 3.00–3.25(3H,m),3,55–3.80(1H,m),4.25–4.45(1H,m), 4.55–4.80(1H,m),6.95–7.15(3H,m),7.15–7.35(1H,m), 7.86 (1H,d,J=2.1Hz),8.34(1H,s),9.60(1H,s) [M+H]$^+$=502,504

EXAMPLE 24

1-[1-[2-[1-[(5-Bromo-3-pyridyl)carbonyl]piperidin-4-yl]ethyl]-piperidin-4-yl]-1,3-dihydro-2H-benzimidazol-2-one Example 4 was repeated except that pyrazinecarboxylic acid was replaced with 5-bromonicotinic acid, to provide the title compound as a pale yellow, amorphous substance.

[M+H]$^+$=512, 514

EXAMPLE 25

1-[1-[2-[1-(2-Thenoyl)piperidin-4-yl]ethyl]-pipendin-4-yl]-1,3-dihydro-2H-benzimidazol-2-one Example 4 was repeated except that pyrazinecarboxylic acid was replaced with thiophene-2-carboxylic acid, to provide the title compound as a pale yellow, amorphous substance.

[M+H]$^+$=439

EXAMPLE 26

1-[1-[2-[1-[(2-Propylthio-3-pyridyl)carbonyl]piperidin-4-yl]ethyl]-piperidin-4-yl]-1,3-dihydro-2H-benzimidazol-2-one Example 4 was repeated except that pyrazinecarboxylic acid was replaced with 2-(propylthio)nicotinic acid, to provide the title compound as a colorless solid.
$^1$H-NMR(CDCl$_3$)δ:1.03(3H,t,J=7.5Hz),0.80–2.60(18H, m), 2.70–2.90(1H,m),2.90–3.30(4H,m),3.30–3,50(1H,m), 4.25–4.50(1H,m),4.65–4.85(1H,m),6.90–7.50(6H,m), 8.43 (1H,d,J=4.8Hz),9.02(1H,s) [M+H]$^+$=508

PRODUCTION EXAMPLE 8

1-[1-[(1α,5α,7β)-3-Azabicyclo[3.3.0]octan-7-yl] piperidin-4-yl]-1,3-dihydro-2H-benzimidazol-2-one With 215 mg of (1α, 5α)-3-(tert-butoxycarbonyl)-3-azabicyclo-[3.3.0]octan-7-one, 200 mg of 1-(piperidin-4-yl)-1,3-dihydro-2H-benzimidazol-2-one and 15 ml of 0.3 M methanolic zinc cyanoborohydride were mixed and stirred for an overnight. Saturated aqueous sodium hydrogencarbonate solution was added to the reaction liquid, followed by extraction with chloroform. The extract was washed with saturated brine, dried over anhydrous magnesium sulfate, removed of the solvent by distillation, and purified on silica gel chromatography (chloroform/methanol=19:1) to provide 240 mg of 1-[1-[(1α,5α,7β)-3-(tert-butoxycarbonyl)-3-azabicyclo[3.3.0]octan-7-yl]piperidin-4-yl]-1,3-dihydro-2H-benzimidazol-2-one. This product was dissolved in 10 ml of chloroform and 3 ml of trifluoroacetic acid was added to the resulting solution, followed by an hour' s stirring at room temperature. The solvent was distilled off, and to the residue saturated aqueous sodium hydrogencarbonate solution was added and extracted with chloroform. The chloroform layer was dried over anhydrous magnesium sulfate. Distilling the solvent off, 110 mg of the title compound was obtained as a colorless, amorphous substance.

EXAMPLE 27

1-[1-[(1α,5α,7β)-3-(Pyrazinylcarbonyl)-3-azabicyclo[3.3.0] octan-7-yl]-piperidin-4-yl]-1,3-dihydro-2H-benzimidazol-2-one To 26 mg of 1-[1-[(1α,5α,7β)-3-azabicyclo[3.3.0]octan-7-yl]-piperidin-4-yl]-1,3-dihydro-2H-benzimidazol-2-one which was obtained in Production Example 8, 1 ml of chloroform, 10 mg of pyrazinecarboxylic acid, 30 μof triethylamine, 16 mg of 1-hydroxybenzotriazole and 23 mg of 1-ethyl-3-[3-(dimethylamino)-propyl]carbodiimide hydrochloride were added, and stirred for an overnight at room temperature. Saturated aqueous sodium hydrogencarbonate solution was added to the reaction liquid, followed by distribution. The organic layer was dried over anhydrous sodium sulfate and the solvent was distilled off. The resulting residue was purified on silica gel chromatography (chloroform/methanol=10: 1), to provide 11 mg of the title compound as a colorless, amorphous substance.
$^1$H-NMR(CDCl$_3$)δ:1.35–1.60(2H,m), 1.68–1.95(4H,m), 2.06–2.35(4H,m),2.35–2.60(1H,m),2.60–2.82(3H,m), 3.05–3.25(2H,m), 3.70–4.00(3H,m),4.27–4.47(1H,m), 6.95–7.14(3H,m),7.22–7.38(1H,m),8.55(1H,dd,J=1.4,2.5 Hz), 8.64(1H,d,J=2.5 Hz),9.12(1H,d,J=1.4 Hz),9.32(1H,s) [M+H]$^+$=433

PRODUCTION EXAMPLE 9

1-[1-[(1α,5α,7α)-3-Azabicyclo[3.3.0]octan-7-yl] piperidin-4-yl]-1,3-dihydro-2H-benzimidazol-2-one dihydrochloride In 20 ml of methanol, 710 mg of (1α,5α)-3-(tert-butoxycarbonyl)-3-azabicyclo[3.3.0]octan-7-one was dissolved, and 120 mg of sodium borohydride was added to the formed solution under cooling with ice, followed by an hour's stirring. Saturated aqueous ammonium chloride solution and successively ethyl acetate were added to the reaction liquid which then was separated. The organic layer was dried over anhydrous magnesium sulfate, the solvent was distilled off, and the residue was purified on silica gel chromatography (hexane/ethyl acetate=1:1,3:7) to provide 540 mg of (1α, 5α,7β)-3-(tert-butoxycarbonyl)-3-azabicyclo[3.3.0]octan-7-ol. Of the product, 517 mg was dissolved in 20 ml of chloroform, and 1.6 ml of triethylamine and 0.26 ml of methanesulfonyl chloride were added to the solution, followed by 40 minutes' stirring at room temperature. Saturated aqueous sodium hydrogencarbonate solution was added to the reaction liquid which then was extracted with ethyl acetate. The extract was washed with saturated brine, dried over anhydrous magnesium sulfate, and the solvent was distilled off. The residue was purified on silica gel chromatography (hexane/ethyl acetate=1:1, 3:7) to provide 662 mg of (1α,5α,7β)-3-(tert-butoxycarbonyl)-7-(methylsulfonyloxy)-3-azabicyclo[3.3.0]octane. Of the product, 205 mg was dissolved in 5 ml of dimethylformamide, and to the solution 205 mg of 1-(piperidin-4-yl)-1,3-dihydro-2H-benzimidazol-2-one and 185 mg of potassium carbonate were added, followed by heating to 80° C. and stirring for an overnight. Cooling the system off by standing, saturated brine was added to the reaction liquid and extracted with chloroform. The extract was washed with water and dried over anhydrous magnesium sulfate. Distilling the solvent off, the residue was purified on silica gel chromatography (chloroform/methanol=97:3, 10:1) to provide 32 mg of 1-[1-[(1α,5α,7α)-3-(tert-butoxycarbonyl)-3-azabicyclo[3.3.0]octan-7-yl]piperidin-4-yl]-1,3-dihydro-2H-benzimidazol-2-one. Thirty (30) mg of the product was dissolved in 10 ml of 10% hydrogen chloride/methanol, stirred for an overnight, and the solvent was distilled off to provide 28 mg of the title compound.

EXAMPLE 28

1-[1-[(1α,5α,7α)-3-(Pyrazinylcarbonyl)-3-azabicyclo[3.3.0]octan-7-yl]-piperidin-4-yl -1,3-dihydro-2H-benzimidazol-2-one To 14 mg of 1-[1-[(1α,5α,7α)-3-azabicyclo[3.3.0]octan-7-yl]-piperidin-4-yl]-1,3-dihydro-2H-benzimidazol-2-one dihydrochloride, 0.1 ml of triethylamine, 1 ml of chloroform, 9 mg of pyrazinecarboxylic acid, 14 mg of 1-ethyl-3-[3-(dimethylamino)propyl]carbodiimide hydrochloride and 10 mg of 1-hydroxybenzotriazole were added and stirred for an overnight at room temperature. Saturated aqueous sodium hydrogencarbonate solution was added to the reaction liquid, which then was extracted with chloroform. The extract was dried on magnesium sulfate, concentrated and purified on silica gel chromatography (chloroform/methanol=10:1) to provide 4 mg of the title compound as a colorless, amorphous substance.

$^1$H-NMR(CDCl$_3$)δ:1.51–1.70(2H,m),1.72–1.99(4H,m), 2.04–2.23(2H,m),2.32–2.62(3H,m),2.80–3.00(2H,m), 3.02–3.22(2H,m),3,50–3.72(2H,m),3.87–4.10(2H,m), 4.23–4.50(1H,m),6.95–7.12(3H,m),7.19–7.40(1H,m), 8.44(1H,s),8.55(1H,dd,J=1.5,2.6 Hz),8.65(1H,d,J=2.6 Hz), 9.13(1H,d,J=1.5 Hz) [M+H]$^+$=433

EXAMPLE 29

1-[1-[(1α,7α,9β)-4-(Pyrazinylcarbonyl)-4-azabicyclo[5.3.0]nonan-9-yl]-piperidin-4-yl]-1,3-dihydro-2H-benzimidazol-2-one Example 27 was repeated except that 1-[1-[(1α,7α,9β)-4-azabicyclo[5.3.0]nonan-9-yl]piperidin-4-yl]-1,3-dihydro-2H-benzimidazol-2-one was used in place of 1-[1-[(1α,5α,7β)-3-azabicyclo[3.3.0]octan-7-yl]piperidin-4-yl]-1,3-dihydro-2H-benzimidazol-2-one, to provide the title compound as a colorless, amorphous substance.

$^1$H-NMR(CDCl$_3$)δ:1.14–2.40(2H,m),1.55–2.61(15H,m), 3.05–3.29(4H,m),3.62–3.82(1H,m),4.22–4.48(2H,m), 6.96–7.15(3H,m),7.25–7.40(1H,m),8.55(1H,dd,J=1.6,2.6 Hz), 8.62(1H,d,J=2.6 Hz),8.88(1H,d,J=1.6 Hz),9.68(1H,s) [M+H]$^+$=461

INDUSTRIAL UTILIZABILITY

Benzimidazolone derivatives of the present invention exhibit antagonism to muscarinic acetylcholine receptors, and are useful as treating agent and/or prophylactic of, for example, Parkinson's disease, drug-induced parkinsonism, dystonia, akinesia, pancreatitis, bilestone/cholecystitis, biliary dyskinesia, achalasia, pain, itch, cholinergic urticaria, irritable bowel syndrome, vomiting, nausea, dizziness, Meniere's disease, motion sickness such as space sickness, sea sickness and car sickness and urinary disturbance.

The invention claimed is:
1. Benzimidazolone compounds represented by formula (I)

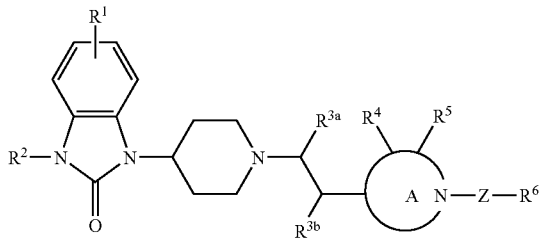

in which A ring

stands for a 5- to 8-membered aliphatic heterocyclic ring containing one nitrogen atom; $R^1$ binds to the benzene ring, standing for hydrogen, halogen, lower alkyl or lower alkoxy; $R^2$ stands for hydrogen or optionally phenyl-substituted lower alkyl; $R^{3a}$ and $R^{3b}$ stand for hydrogen or $R^3$, $R^{3a}$ standing for hydrogen when $R^{3b}$ stands for $R^3$ and $R^{3a}$ standing for $R^3$ when $R^{3b}$ stands for hydrogen; $R^3$ stands for hydrogen, halogen, hydroxyl, lower alkyl or lower alkenyl, or $R^3$ and $R^4$ together form a 3- to 6-membered carbocyclic ring with the carbon atoms to which they bind; $R^4$ and $R^5$ which are the same or different and bind to optional carbon atoms constituting said heterocyclic ring, stand for hydrogen, halogen, hydroxyl, lower alkyl or lower alkenyl, or $R^4$ and $R^5$ together form methylene group with the carbon atoms to which they bind, or $R^3$ and $R^4$ together form a 3- to 6-membered carbocyclic ring with the carbon atoms to which they bind, or $R^4$ and $R^5$ together form a 3- to 6-membered carbocyclic ring together with the carbon atoms to which they bind; $R^6$ stands for aryl or heteroaryl which may have one, two or more substituents selected from the group consisting of halogen, cyano, nitro, lower alkyl, lower alkenyl, lower alkynyl, lower cycloalkyl, halogenated lower alkyl, lower alkylamino, di-lower alkylamino, lower alkylthio, lower alkylsulfonyl, optionally fluorine-substituted lower alkoxy, lower acyl, lower acylamino, lower alkoxycarbonyl, carbamoyl, lower alkylcarbamoyl, di-lower alkylcarbamoyl, sulfamoyl, lower alkylsulfamoyl, di-lower alkylsulfamoyl, carbamoyloxy, lower alkylcarbamoyloxy, di-lower alkylcarbamoyloxy, lower alkoxycarbonylamino, sulfamoylamino, (lower alkylsulfamoyl)amino, (di-lower alkylsulfamoyl)amino, (lower alkylsulfamoyl)(lower alkyl)amino, (di-lower alkylsulfamoyl)(lower alkyl)amino, (lower alkylsulfonyl)amino, carbamoylamino, (lower alkylcarbamoyl)amino, (di-lower alkylcarbamoyl)

amino and phenoxy; and Z stands for carbonyl (—CO—) or sulfonyl (—SO$_2$—) or salts thereof.

2. Benzimidazolone compounds or salts thereof as described in claim 1, in which the benzimidazolone compounds represented by formula (I) are those of formula (I-a)

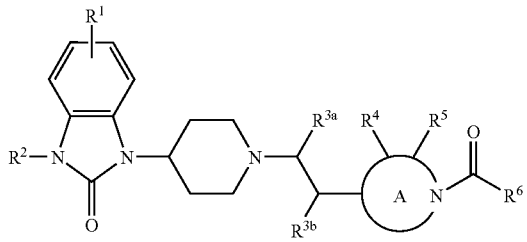

[I-a]

in which R$^1$, R$^2$, R$^{3a}$, R$^{3b}$, R$^4$, R$^5$, R$^6$ and A ring

are same as to those in claim 1.

3. Benzimidazolone compounds or salts thereof as described in claim 1, in which the benzimidazolone compounds represented by formula (I) are those of formula (I-b)

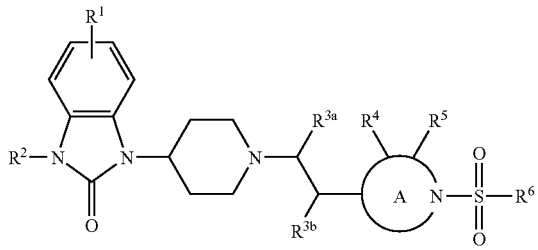

[I-b]

in which R$^1$, R$^2$, R$^{3a}$, R$^{3b}$, R$^4$, R$^5$, R$^6$ and A ring

are same as those in claim 1.

4. Benzimidazolone compounds or salts thereof as described in claim 1, in which the 5- to 8-membered aliphatic heterocyclic ring represented by A ring

is one selected from the group consisting of pyrrolidine ring, piperidine ring, perhydroazepine ring, heptamethylenimine ring and 1,2,5,6-tetrahydropyridine ring.

5. Benzimidazolone compounds or salts thereof as described in claim 1, in which R$^6$ is a group selected from the group consisting of phenyl, 1-naphthyl, 2-naphthyl, 2-tolyl, 3-tolyl, 4-tolyl, 2-chlorophenyl, 3-chlorophenyl, 4-chlorophenyl, 3,4-dichlorophenyl, 3,5-dichlorophenyl, 3-bromophenyl, 2-fluoro-4-chlorophenyl, 3-iodophenyl, 4-iodophenyl, 2-(trifluoromethyl)phenyl, 3-(trifluoromethyl)phenyl, 2-(dimethylamino)phenyl, 3-(dimethylamino)phenyl, 2-cyanophenyl, 3-cyanophenyl, 2-(acetamido)phenyl, 3-(acetamido)phenyl, 3-(chloromethyl)phenyl, 2-methoxyphenyl, 3-methoxyphenyl, 2-(phenoxy)phenyl, 3-(phenoxy)phenyl, pyrazinyl, 2-pyridyl, 3-pyridyl, 4-pyridyl, 5-chloro-3-pyridyl, 5-bromo-3-pyridyl, 5-cyano-3-pyridyl, 2-chloro-3-pyridyl, 6-chloro-3-pyridyl, 2,3-dichloropyridin-5-yl, 5-methyl-3-pyridyl, 2-methoxypyridyl, 2-phenoxypyridyl, 2-(methylthio)pyridyl, 2- methylpyridin-5-yl, 3-bromopyridin-5-yl, 2,6-dimethoxypyridyl, 2-(propylthio)pyridyl, 2-thienyl, 3-thienyl, 2-quinolyl and 3-quinolyl.

6. Benzimidazolone compounds or salts thereof as described in claim 1, in which the benzimidazolone compound represented by formula (I) is 1-[1-[2-(1-benzoylpiperidin-4-yl)ethyl]piperidin-4-yl]-1,3-dihydro-2H-benzimidazol-2-one, 1-[1-[2-[1-(4-chlorophenylsulfonyl)piperidin-4-yl]ethyl]piperidin-4-yl]-1,3-dihydro-2H-benzimidazol-2-one, 1-[1-[2-[1-[4-(trifluoromethoxy)phenylsulfonyl]piperidin-4-yl]ethyl]-piperidin-4-yl]-1,3-dihydro-2H-benzimidazol-2-one, 1-[1-[2-[1-(pyrazinylcarbonyl)piperidin-4-yl]ethyl]piperidin-4-yl]-1,3-dihydro-2H-benzimidazol-2-one,

[1-[2-[1,2,5,6-tetrahydro-1-(pyrazinylcarbonyl)-4-pyridyl]ethyl]-piperidin-4-yl]-1,3-dihydro-2H-benzimidazol-2-one, 1-[1-[2-[1-(pyrazinylcarbonyl)-3-methylene-piperidin-4-yl]ethyl]-piperidin-4-yl]-1,3-dihydro-2H-benzimidazol-2-one, (S*)-1-[1-[2-[1-(pyrazinylcarbonyl)perhydroazepin-4-yl]ethyl]-piperidin-4-yl]-1,3-dihydro-2H-benzimidazol-2-one, (R*)-1-[1-[2-[1-(pyrazinylcarbonyl)perhydroazepin-4-yl]ethyl]-piperidin-4-yl]-1,3-dihydro-2H-benzimidazol-2-one, (S*)-1-[1-[2-[1-(3-pyridylcarbonyl)perhydroazepin-4-yl]ethyl]-piperidin-4-yl]-1,3-dihydro-2H-benzimidazol-2-one, (R*)-1-[1-[2-[1-(3-pyridylcarbonyl)perhydroazepin-4-yl]ethyl]-piperidin-4-yl]-1,3-dihydro-2H-benzimidazol-2-one, 1-[1-[2-[1-(pyrazinylcarbonyl)piperidin-4-yl]propyl]piperidin-4-yl]-1,3-dihydro-2H-benzimidazol-2-one, 1-[1-[2-[1-(3-pyridylcarbonyl)piperidin-4-yl]propyl]piperidin-4-yl]-1,3-dihydro-2H-benzimidazol-2-one, 1-[1-[2-[1-(3-chlorobenzoyl)piperidin-4-yl]propyl]piperidin-4-yl]-1,3-dihydro-2H-benzimidazol-2-one, 1-[1-[2-[1-(3-pyridylcarbonyl)piperidin-4-yl]-1-methylethyl]piperidin-4-yl]-1,3-dihydro-2H-benzimidazol-2-one, 1-[1-[2-hydroxy-2-[4-hydroxy-1-(3-pyridylcarbonyl)piperidin-4-yl]-ethyl]piperidin-4-yl]-1,3-dihydro-2H-benzimidazol-2-one, 1-[1-[2-[1-(2-chlorobenzoyl)piperidin-4-yl]ethyl]-piperidin-4-yl]-1,3-dihydro-2H-benzimidazol-2-one, 1-[1-[2-[1-(3-chlorobenzoyl)piperidin-4-yl]ethyl]-piperidin-4-yl]-1,3-dihydro-2H-benzimidazol-2-one, 1-[1-[2-[1-(3-bromobenzoyl)piperidin-4-yl]ethyl]-piperidin-4-yl]-1,3-dihydro-2H-benzimidazol-2-one, 1-[1-[2-[1-(3-iodobenzoyl)piperidin-4-yl]ethyl]-piperidin-4-yl]-1,3-dihydro-2H-benzimidazol-2-one, 1-[1-[2-[1-(3,5-dichlorobenzoyl)piperidin-4-yl]ethyl]-piperidin-4-yl]-1,3-dihydro-2H-benzimidazol-2-one, 1-[1-[2-[1-(3,4-dichlorobenzoyl)piperidin-4-yl]ethyl]-piperidin-4-yl]-1,3-dihydro-2H-benzimidazol-2-one, 1-[1-[2-[1-(3-pyridylcarbonyl)piperidin-4-yl]ethyl]-piperidin-4-yl]-1,3-dihydro-2H-benzimidazol-2-one, 1-[1-[2-[1-[(5-chloro-3-pyridyl)carbonyl]piperidin-4-yl]
ethyl]-piperidin-4-yl]-1,3-dihydro-2H-benzimidazol-
2-one, 1-[1-[2-[1-[(4,5-dichloro-3-pyridyl)carbonyl]piperidin-4-
yl]ethyl]-piperidin-4-yl]-1,3-dihydro-2H-benzimida-
zol-2-one, 1-[1-[2-[1-[(5-bromo-3-pyridyl)carbonyl]piperidin-4-yl]
ethyl]-piperidin-4-yl]-1,3-dihydro-2H-benzimidazol-
2-one, 1-[1-[2-[1-(2-thenoyl)piperidin-4-yl]ethyl]-piperidin-4-
yl]-1,3-dihydro-2H-benzimidazol-2-one, 1-[1-[2-[1-(3-pyridylcarbonyl)piperidin-4-yl]ethyl]-pip-
eridin-4-yl]-5-fluoro-1,3-dihydro-2H-benzimidazol-2-
one, 1-[1-[2-(1-pyrazinylcarbonylpiperidin-4-yl)ethyl]-piperi-
din-4-yl]-5-fluoro-1,3-dihydro-2H-benzimidazol-2-
one, 1-[1-[2-[1-[(5,6-dichloro-3-pyridyl)carbonyl]-piperidin-
4-yl]ethyl]-piperidin-4-yl]-1,3-dihydro-2H-benzimida-
zol-2-one, 1-[1-[2-[1-[(2-propylthio-3-pyridyl)carbonyl]piperidin-4-
yl]ethyl]-piperidin-4-yl]-1,3-dihydro-2H-benzimida-
zol-2-one, 1-[1-[2-[4-fluoro-1-(pyrazinylcarbonyl)piperidin-4-yl]
propyl]piperidin-4-yl]-1,3-dihydro-2H-benzimidazol-
2-one, 1-[1-[2-[4-fluoro-1-(3-pyridylcarbonyl)piperidin-4-yl]
propyl]piperidin-4-yl]-1,3-dihydro-2H-benzimidazol-
2-one, 1-[1-[(1α,5α,7β)-3-(pyrazinylcarbonyl)-3-azabicyclo
[3.3.0]octan-7-yl]-piperidin-4-yl]-1,3-dihydro-2H-
benzimidazol-2-one, 1-[1-[(1α,5α,7α)-3-(pyrazinylcarbonyl)-3-azabicyclo
[3.3.0]octan-7-yl]-piperidin-4-yl]-1,3-dihydro-2H-
benzimidazol-2-one, 1-[1-[(1α,5α,7β)-3-(3-pyridylcarbonyl)-3-azabicyclo
[3.3.0]octan-7-yl]-piperidin-4-yl]-1,3-dihydro-2H-
benzimidazol-2-one, 1-[1-[(1α,5α,7α)-3-(3-pyridylcarbonyl)-3-azabicyclo
[3.3.0]octan-7-yl]-piperidin-4-yl]-1,3-dihydro-2H-
benzimidazol-2-one, 1-[1-[(1α,7α,9β)-4-(pyrazinylcarbonyl)-4-azabicyclo
[5.3.0]nonan-9-yl]-piperidin-4-yl]-1,3-dihydro-2H-
benzimidazol-2-one, 1-[2-[7-(3-pyridylcarbonyl)-7-azaspiro[3.5]nonan-2-yl]
ethyl]-piperidin-4-yl]-1,3-dihydro-2H-benzimidazol-
2-one, 1-[1-[2-[7-(pyrazinylcarbonyl)-7-azaspiro[3.5]nonan-2-
yl]ethyl]-piperidin-4-yl]-1,3-dihydro-2H-benzimida-
zol-2-one, or 1-[1-[[6-(3-pyridylcarbonyl)-6-azaspiro[2.5]octan-1-yl]
methyl]-piperidin-4-yl]-1,3-dihydro-2H-benzimidazol-
2-one.

7. A method for producing benzimidazolone compounds represented by formula (I)

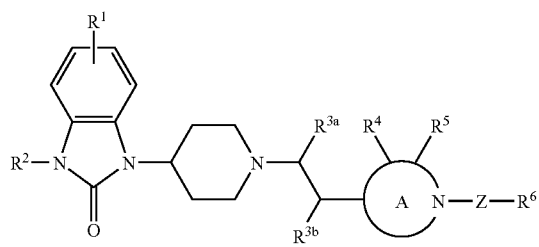

[I]

in which $R^1$, $R^2$, $R^{3a}$, $R^{3b}$, $R^4$, $R^5$, $R^6$, Z and A ring

are same as described in claim 1 or salts thereof, which comprises a) reacting a compound represented by formula (II)

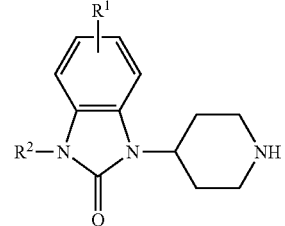

[II]

in which $R^1$ and $R^2$ are same as earlier defined with a compound represented by formula (III)

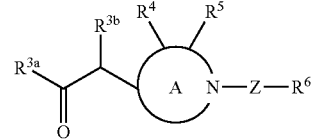

[III]

in which $R^{3a}$, $R^{3b}$, $R^4$, $R^5$, $R^6$, Z and A ring

are same as earlier defined to form a compound represented by formula (IV)

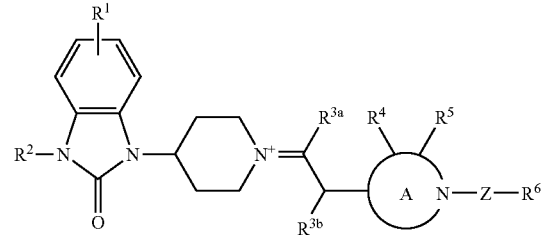

[IV]

in which $R^1$, $R^2$, $R^{3a}$, $R^{3b}$, $R^4$, $R^5$, $R^6$, Z and A ring

are same as earlier defined and b) reducing the compound of formula (IV) which is obtained in a).

8. A method for producing benzimidazolone compounds represented by formula (I)

[I]

in which $R^1$, $R^2$, $R^{3a}$, $R^{3b}$, $R^4$, $R^5$, $R^6$, Z and A ring are same as described in claim 1 or salts thereof, which comprises reacting a compound represented by formula (II)

[II]

in which $R^1$ and $R^2$ are same as earlier defined with a compound represented by formula (III)

[III]

in which $R^{3a}$, $R^{3b}$, $R^4$, $R^5$, $R^6$, Z and A ring are same as earlier defined in the presence of a reagent which is selected from a group consisting of sodium borohydride, sodium cyanoborohydride, zinc cyanoborohydride and sodium triacetoxyborohydride.

9. A method for producing benzimidazolone compounds represented by formula (I)

[I]

in which $R^1$, $R^2$, $R^{3a}$, $R^{3b}$, $R^4$, $R^5$, $R^6$, Z and A ring are same as described in claim 1 or salts thereof, which comprises reacting a compound represented by the general formula (II)

[II]

in which $R^1$ and $R^2$ are same as earlier defined with a compound represented by formula (V)

[V]

in which $R^{3a}$, $R^{3b}$, $R^4$, $R^5$, $R^6$, Z and A ring are same as earlier defined; $R^7$ stands for methylsulfonyl, phenylsulfonyl or p-tolylsulfonyl.

10. A method for producing benzimidazolone compounds represented by formula (I-a)

[I-a]

in which $R^1$, $R^2$, $R^{3a}$, $R^{3b}$, $R^4$, $R^5$, $R^6$ and A ring are same as defined in claim 2 or salts thereof which comprises reacting a compound of a formula (VI)

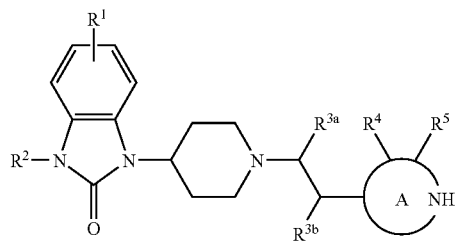

in which R¹, R² R³ᵃ, R³ᵇ, R⁴, R⁵ and A ring

are same as earlier defined with a carboxylic acid represented by formula (VII-a)

R⁶—COOH  [VII-a]

in which R⁶ is same as earlier defined or an activated compound thereof.

11. A method for producing benzimidazolone compounds represented by formula (I-b)

[I-b]

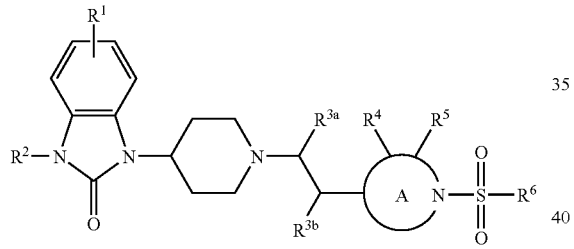

in which R¹, R², R³ᵃ, R³ᵇ, R⁴, R⁵, R⁶ and A ring

are same as defined in claim 3 or salts thereof, which comprises reacting a compound represented by formula (VI)

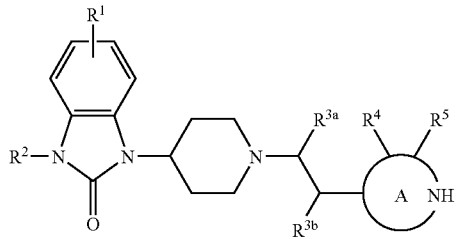

in which R¹, R², R³ᵃ, R³ᵇ, R⁴, R⁵ and A ring

are same as earlier defined with a sulfonic acid of formula (VII-b)

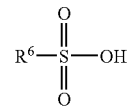
[VII-b]

in which R⁶ is same as earlier defined or an activated compound thereof, in the presence or absence of a base.

12. Pharmaceutical compositions containing benzimidazolone compounds represented by formula (I)

[I]

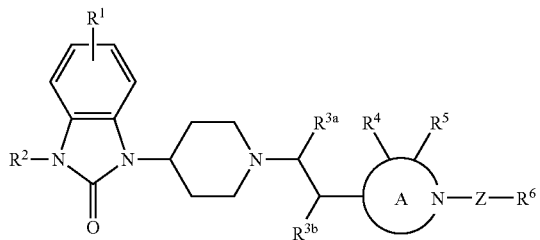

in which R¹, R², R³ᵃ, R³ᵇ, R⁴, R⁵, R⁶, Z and A ring

are same as defined in claim 1 or salts thereof, and pharmaceutically acceptable adjuvants.

* * * * *